(12) United States Patent
Willey et al.

(10) Patent No.: US 11,312,987 B2
(45) Date of Patent: *Apr. 26, 2022

(54) METHODS FOR STANDARDIZED SEQUENCING OF NUCLEIC ACIDS AND USES THEREOF

(71) Applicant: The University of Toledo, Toledo, OH (US)

(72) Inventors: James C. Willey, Toledo, OH (US); Thomas Blomquist, Waterville, OH (US); Erin Crawford, Rossford, OH (US)

(73) Assignee: The University of Toledo, Toledo, OH (US)

( * ) Notice: Subject to any disclaimer, the term of this patent is extended or adjusted under 35 U.S.C. 154(b) by 703 days.

This patent is subject to a terminal disclaimer.

(21) Appl. No.: 15/909,525

(22) Filed: Mar. 1, 2018

(65) Prior Publication Data

US 2018/0216163 A1 Aug. 2, 2018

Related U.S. Application Data

(63) Continuation of application No. 14/646,585, filed as application No. PCT/US2013/071656 on Nov. 25, 2013, now Pat. No. 9,944,973.

(60) Provisional application No. 61/784,394, filed on Mar. 14, 2013, provisional application No. 61/730,463, filed on Nov. 27, 2012, provisional application No. 61/729,853, filed on Nov. 26, 2012.

(51) Int. Cl.
| | | |
|---|---|---|
| *C12Q 1/6806* | (2018.01) | |
| *C12Q 1/6869* | (2018.01) | |
| *C12Q 1/6851* | (2018.01) | |
| *C40B 20/04* | (2006.01) | |

(52) U.S. Cl.
CPC ......... *C12Q 1/6806* (2013.01); *C12Q 1/6851* (2013.01); *C12Q 1/6869* (2013.01); *C40B 20/04* (2013.01)

(58) Field of Classification Search
None
See application file for complete search history.

(56) References Cited

U.S. PATENT DOCUMENTS

2006/0188908 A1* 8/2006 Willey ............... C12P 19/34
435/6.1

OTHER PUBLICATIONS

Blomquist et al., "Amplicon library preparation with internal standard mixtures improves analytical performance and reduces cost of RNA-sequencing", Pace Environmental Law Review, http://www.accugenomics.com/wp-content/uploads/2014/11/Ampliconlibrary-preparation.pdf, accessed May 12, 2016.
Blomquist et al., "Targeted RNA-Sequencing with Competitive Multiplex-PCR Amplicon Libraries", PLOS ONE, 2013, vol. 8, Issue 11, pp. 1-14.
Kircher et al., "Double indexing overcomes inaccuracies in multiplex sequenceing on the Illumina platform", Nucleic Acids Research, 2012, vol. 40, No. 1, pp. 1-8.
Krueger et al., "Large Scale Loss of Data in Low-Diversity Illumina Sequencing Libraries Can Be Recovered by Deferred Cluster Calling", PLOS ONE 2011, vol. 6, No. 1, pp. 1-7.
Sanchez-Seco et al., "Generic RT-nested-PCR for detection of flaviviruses using degenerated primers and internal control followed by sequencing for specific identification", Journal of Virological Methods, 2005, vol. 126, pp. 101-109.
Tian et al., "Sequencing bias: comparison of different protocols of MicroRNA library construction", BMC Biotechnology, 2010, vol. 10, pp. 1-9.
European Search Report, Application No. 18159851.7, dated May 28, 2018.

* cited by examiner

*Primary Examiner* — Samuel C Woolwine
(74) *Attorney, Agent, or Firm* — MacMillan, Sobanski & Todd, LLC

(57) ABSTRACT

Methods for controlling for non-systematic error in an amplification-based next generation sequencing (NGS) library preparation are described, which method includes using an internal amplification control (IAC) sharing identical priming sites to a native nucleic acid target template of interest in a NGS library preparation.

11 Claims, 46 Drawing Sheets

| Detect Fold Change | Accuracy | 95% CI |
|---|---|---|
| > 10 | 0.99 | (0.99- 1.00) |
| 5 to 10 | 0.99 | (0.99- 1.00) |
| 3 to 5 | 0.97 | (0.95-0.99) |
| 2 to 3 | 0.91 | (0.87-0.94) |
| 1.5 to 3 | 0.80 | (0.74-0.86) |

| Detect Fold Change | Accuracy | 95% CI |
|---|---|---|
| > 10 | 0.99 | (0.99- 1.00) |
| 5 to 10 | 0.99 | (0.99- 1.00) |
| 3 to 5 | 0.97 | (0.95-0.99) |
| 2 to 3 | 0.91 | (0.87-0.94) |
| 1.5 to 2 | 0.80 | (0.74-0.86) |

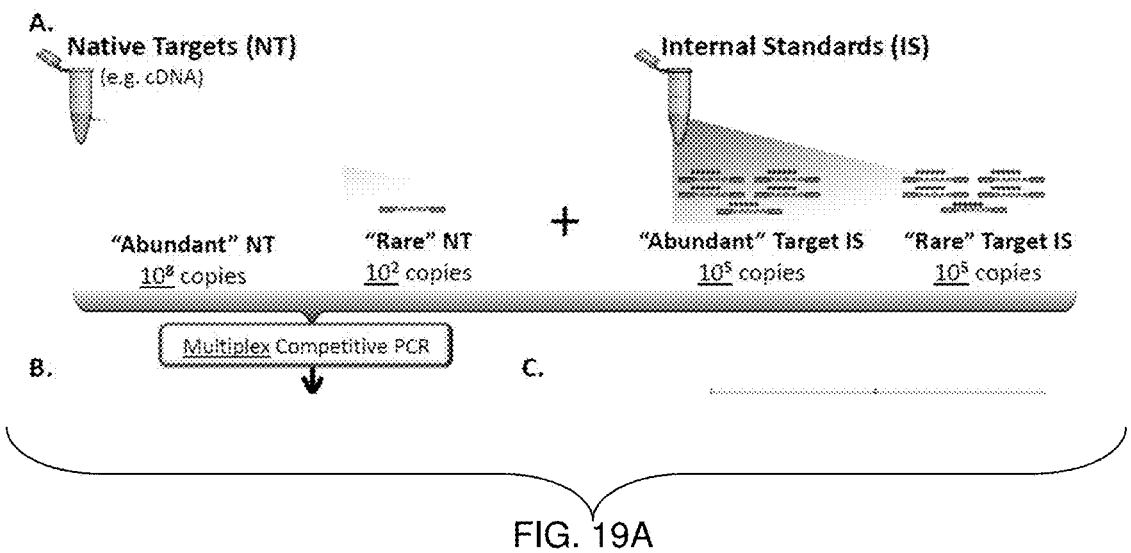
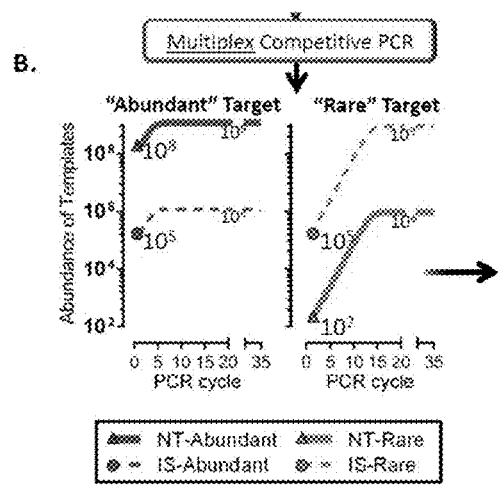
FIG. 19A
FIG. 19B
FIG. 19C

| ERCC Target Measurements | A | B | C | D |
|---|---|---|---|---|
| Valid | 26 | 26 | 26 | 26 |
| True negative | 0 | 0 | 0 | 0 |
| Failed | 1 | 1 | 1 | 1 |

| Endogenous Target Measurements | A | B | C | D | gDNA |
|---|---|---|---|---|---|
| Valid | 99 | 99 | 96 | 107 | 123 |
| True Negative | 4 | 12 | 6 | 4 | 0 |
| Failed | 20 | 12 | 21 | 12 | 0 |

FIG. 26

| HUGO and Sample ID | STARSEQ | Taqman | RNA-Seq |
|---|---|---|---|
| RPL3L Sample-D | < -2.4879 | -3.24 | -2.90 |
| ANXA13 Sample-C | < -2.127 | -3.20 | -2.25 |
| MMP7 Sample-C | < -1.7003 | -3.27 | -2.23 |
| KRT24 Sample-D | < -1.6589 | -3.00 | -2.31 |
| KIAA0101 Sample-B | < -1.3856 | -2.24 | -1.64 |
| KRT24 Sample-B | < -1.2609 | -2.83 | -1.88 |
| STMN2 Sample-A | < -1.0849 | -1.47 | -1.92 |
| IL18R1 Sample-B | < -0.938 | -2.28 | -0.81 |
| DPP4 Sample-B | < -0.733 | -1.64 | -0.61 |
| IL18R1 Sample-D | < -0.7132 | -2.37 | -1.10 |
| KIT Sample-C | < -0.0946 | -0.80 | -0.18 |
| KIT Sample-A | < 0.1187 | -1.21 | -0.53 |
| IL1F6 Sample-B | < -1.9726 | ND | ND |
| POU1F1 Sample-C | < -1.9169 | ND | -3.95 |
| POU1F1 Sample-B | < -1.8552 | ND | -2.62 |
| RPL3L Sample-B | < -1.8183 | ND | -3.15 |
| KRT24 Sample-C | < -1.6485 | ND | -2.72 |
| POU1F1 Sample-A | < -1.5431 | ND | -4.18 |
| CYP2C9 Sample-D | < -1.1907 | ND | -3.41 |
| ABCB11 Sample-B | < -1.1123 | ND | -2.38 |
| SERPINB7 Sample-B | < -1.0772 | ND | -3.15 |
| DLG7 Sample-B | < -0.8081 | ND | -2.31 |
| FOXA1 Sample-B | < -0.4969 | ND | -2.42 |
| CYP2C9 Sample-C | < 0.37 | ND | -3.20 |
| CYP2C9 Sample-B | < 0.6952 | ND | -2.92 |
| CYP2C9 Sample-A | < 0.7906 | ND | -3.16 |

FIG. 27

| Intra-assay; Intra-sample SD | 0.08 |
| Intra-assay; Inter-sample SD | 0.18 |
| Inter-assay; Inter-sample SD | 0.40 |

FIG. 28

METHODS FOR STANDARDIZED SEQUENCING OF NUCLEIC ACIDS AND USES THEREOF

CROSS-REFERENCE TO RELATED APPLICATIONS

This application is a continuation application of U.S. Ser. No. 14/646,585, filed May 21, 2015, now allowed, which claims priority to PCT/US2013/071656 filed Nov. 25, 2013, which claims the benefit of US provisional applications having Ser. No. 61/729,853 filed Nov. 26, 2012; Ser. No. 61/730,463 filed Nov. 27, 2012; and Ser. No. 61/784,394 filed Mar. 14, 2013, the entire disclosures of which are expressly incorporated herein by reference.

STATEMENT REGARDING FEDERALLY SPONSORED RESEARCH

The invention was made with U.S. Government support under Grant Numbers CA138397, CA148572 and HL108016 awarded by the National Institutes of Health. The United States Government has certain rights in the invention.

FIELD OF THE INVENTION

The present invention relates methods for standardized sequencing of nucleic acids and uses thereof.

BACKGROUND

The identification of genetic information is becoming a key piece of information for the diagnosis and treatment of many diseases. In order to make such diagnostic tool readily available, it is desired that this identification be as efficient and as inexpensive as possible. For diagnostic, medical, regulatory and ethical aspects, this identification should be as accurate as possible in order to rule out false measurements.

In addition to the desire to acquire human genetic material information, there is great interest in acquiring genetic information on, for example, mitochondria, pathogens and organisms that cause diseases.

One method for acquiring information is the Sanger sequencing method of genome analysis. Other methods are becoming available which provide an improved performance when compared with the Sanger sequencing method. These methods include a short high density parallel sequencing technology, next generation sequencing (i.e., NextGen or "NGS"), which are attempting to provide a more comprehensive and accurate view of RNA in biological samples than the Sanger sequence method.

Next-generation sequencing (NGS) is useful in a multitude of clinical applications by virtue of its automated and highly parallelized analysis of nucleic acid templates. However, the limit of clinical questions that NGS can address is largely determined by: i) the upstream source of nucleic acid template (e.g., human tissue, microbial sample, etc.), and ii) whether the clinically relevant biological variation in the nucleic acid template is greater than the technical variation (which is often introduced by such variants as workflow for sample preparation, sequencing and/or data analysis).

The workflow for NGS library preparation varies widely, but can broadly be grouped into one of two approaches: 1) digestion or fragmentation of the nucleic acid sample with subsequent ligation to a universal adaptor sequence, or 2) PCR with target specific primers that incorporate a universal adaptor sequence at their 5' ends. In both approaches, if a nucleic acid template is RNA, a reverse transcription step is used to create the requisite DNA template for sequencing.

One concern with NGS is that these quantitative sequencing methods have high intra-lab and inter-lab variation. This problem thus reduces the value of any results, and has prevented the use of these sequencing methods in molecular diagnostics.

For example, non-systematic (i.e., non-reproducible) biases (i.e., errors), are often inadvertently introduced during preparation of the sequencing library. These non-systemic biases are a major roadblock to implementing NGS as a reliable and efficient routine measurement of nucleic acid abundance (quantification) in the clinical setting.

The most likely source of non-systematic bias (thus preventing inter-laboratory comparison, and hence routine clinical use, of quantitative NGS data) stems from issues arising from nucleic acid fragmentation, adaptor ligation and PCR.

Also, although not explicitly required, the FDA has issued guidance and industry recommendations that PCR-based in vitro diagnostic (IVD) devices should contain internal amplification controls (IAC) to control for interfering substances and verify that a negative result for a sample is not caused by inhibitors.

In addition, in order to avoid stochastic sampling error and ensure reliable measurements, it is necessary to sequence (i.e., read) a sufficient number of copies of the analyte being measured. One problem is that the range of transcript representation following library preparation often remains very high, typically one million-fold or greater, imposing high cost. This is because the transcripts from each gene must be sequenced at least 10 times (ensure 10 "reads"). To ensure 10 reads for the least represented genes, it is necessary to read a gene represented at one million fold higher level at least 10 million times.

Thus, a NGS method that reduces inter-experimental and inter-laboratory variation in measurement of nucleic acid copy number in samples will be of great use to both research and clinical applications.

SUMMARY OF THE INVENTION

Described herein is a method for providing reproducibility in measurement of nucleic acid copy number in samples, comprising measuring a proportional relationship of at least one native target sequencing event of at least one nucleic acid in a sample to the respective competitive internal amplification control (IAC) for that nucleic acid.

Also described herein is a method where the at least one event comprises: an observation, a count and/or a read between the native target and its respective IAC.

Also described herein is a method for controlling for non-systematic error in PCR-based NGS library preparation, comprising sharing identical priming sites to a native nucleic acid template of interest so as to mimic the kinetics of the native target in the PCR reaction, and thus control for target-specific variation in PCR efficiency.

Also described herein is the use of a competitive IAC method to provide for the convergence of target analyte representation in a sample, while retaining quantitative information of the original representation of both low- and high-abundance target, enabling quantitative measurement of original representation with a low number of sequencing reads.

In a particular embodiment, described herein is a method for determining an amount of a first nucleic acid, comprising:

providing a series of serially-diluted standardized mixtures comprising a competitive template for said first nucleic acid and a competitive template for a second nucleic acid present in a number of samples comprising said first nucleic acid, wherein said competitive templates are at known concentrations relative to each other; combining one of said samples comprising said first nucleic acid with a first one of said serially-diluted standardized mixtures;

co-amplifying said first nucleic acid and said competitive template for said first nucleic acid to produce amplified product thereof; obtaining a first relationship, said first relationship comparing said amplified product of said first nucleic acid to said amplified product of said competitive template for said first nucleic acid; determining whether said first relationship is within about 1:10 to about 10:1;

if not, repeating said combining, co-amplifying, obtaining and determining steps with a second one of said serially-diluted standardized mixtures;

co-amplifying said second nucleic acid and said competitive template for said second nucleic acid to produce amplified product thereof;

obtaining a second relationship, said second relationship comparing said amplified product of said second nucleic acid to said amplified product of said competitive template for said second nucleic acid; and comparing said first and said second relationships.

In one embodiment, the method includes comparing said amplified project of said first nucleic acid to said amplified project of said competitive template for said first nucleic, determining whether said first relationship is within about 1:100 to about 100:1, or 1:1000 to about 1000:1, or 1:10,000 to about 10,000 to 1, if not, repeating said combining, co-amplifying, obtaining and determining steps with a second one of said serially-diluted standardized mixtures;

co-amplifying said second nucleic acid and said competitive template for said second nucleic acid to produce amplified product thereof; obtaining a second relationship;

said second relationship comparing said amplified product of said second nucleic acid to said amplified project of said competitive template for said second nucleic acid; and comparing said first and said second relationships.

Further, in certain embodiments, the products from the series of co-amplification reactions in claim 2 are combined and amplified in a second round using primer pairs that recognize each NT and CT product from first round of amplification and that also have gene specific barcode primer and universal primer at 5' end to facilitate sequencing.

Other systems, methods, features, and advantages of the present invention will be or will become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

FIGS. 2A-2F: Graphs showing titration of a mixture of approximated equimolar competitive internal amplification controls (IAC) relative to: FIG. 2A) a fixed input amount of 100,000 copies genomic DNA (gDNA) into Multiplex-PCR, or 11 ng of Reverse Transcribed RNA cDNA material from SEQC Samples: FIG. 2B) A-RT1, FIG. 2C) A-RT2, FIG. 2D) B, FIG. 2E) C and FIG. 2F) D), input into each Multiplex-PCR. Plotted on the X-axis is the initially estimated amount of each IAC in the equimolar mixture. The Y-axis represents the frequency of observed sequencing events (reads) divided by the sum of read frequencies for the native template and its respective competitive IAC.

FIGS. 19A-19C: STARSEQ reduces oversampling without signal compression.

FIG. 26: Assay Performance.

FIG. 27: STARSEQ "true negative" versus Taqman and RNA-sequencing.

FIG. 28: Standard Deviation of ERCC measurements.

DETAILED DESCRIPTION

Figure 1:
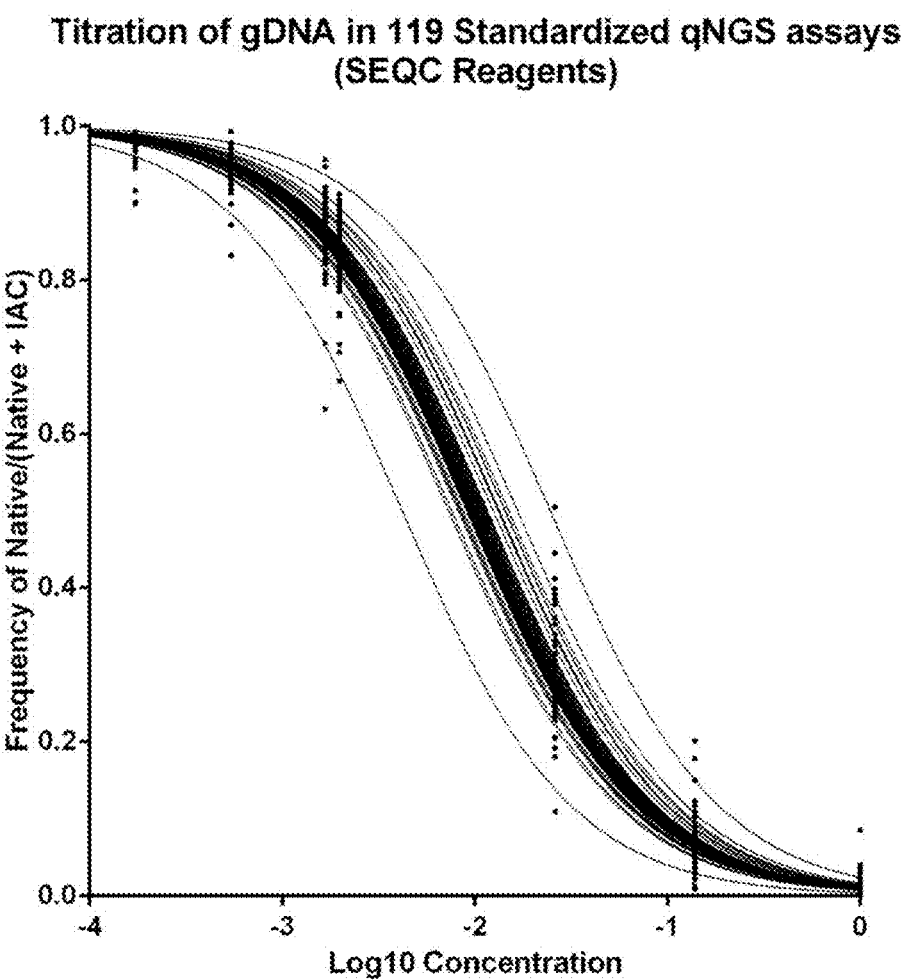
FIG. 1: A549 gDNA titrated relative to ICA mixture. Graph showing titration of a mixture of approximately equimolar competitive internal amplification controls (IAC) relative to a fixed amount of genomic DNA (gDNA) input of 100,000 copies into each Multiplex-PCR. Plotted on the X-axis is the initially estimated amount of each IAC in equimolar mixture. The Y-axis represents the frequency of observed sequencing events (reads) for each native template divided by the sum of read frequencies for the native template and its respective competitive IAC.
Figure 2A:
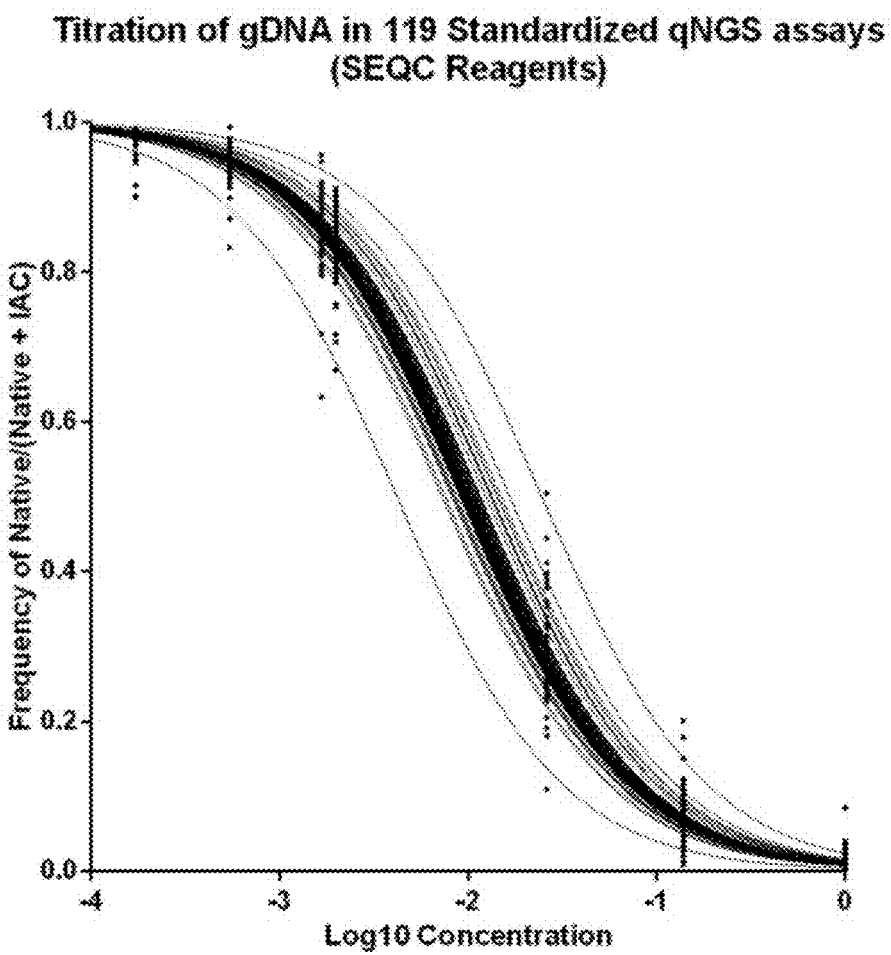
Figure 2B:
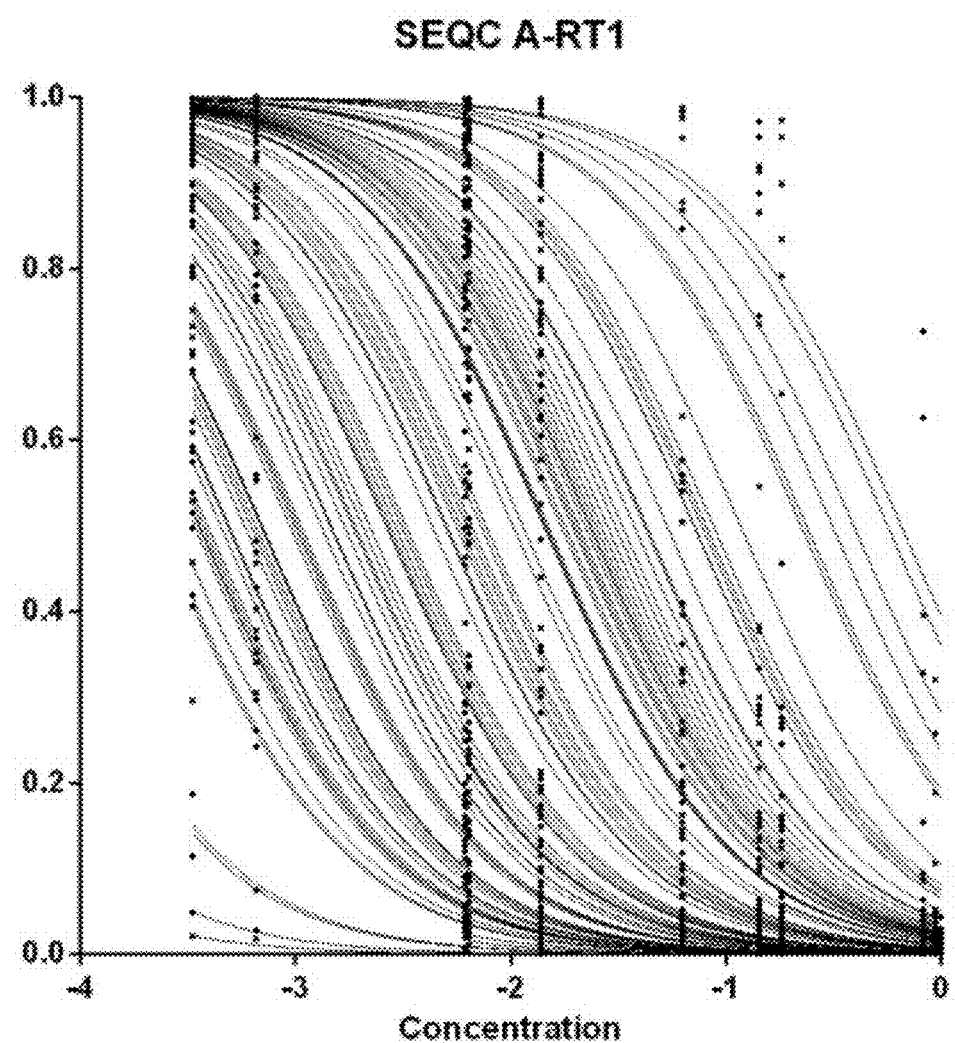
Figure 2C:
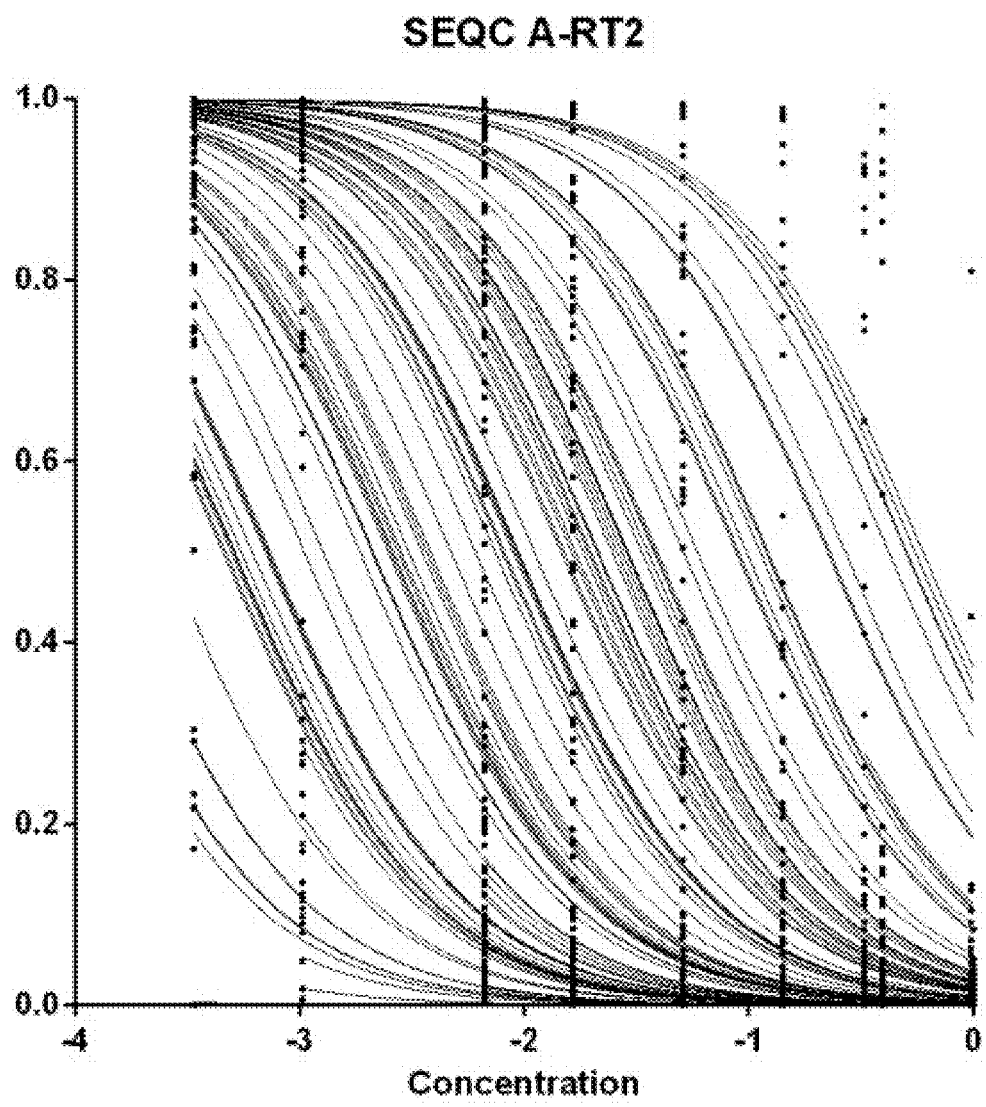
Figure 2D:
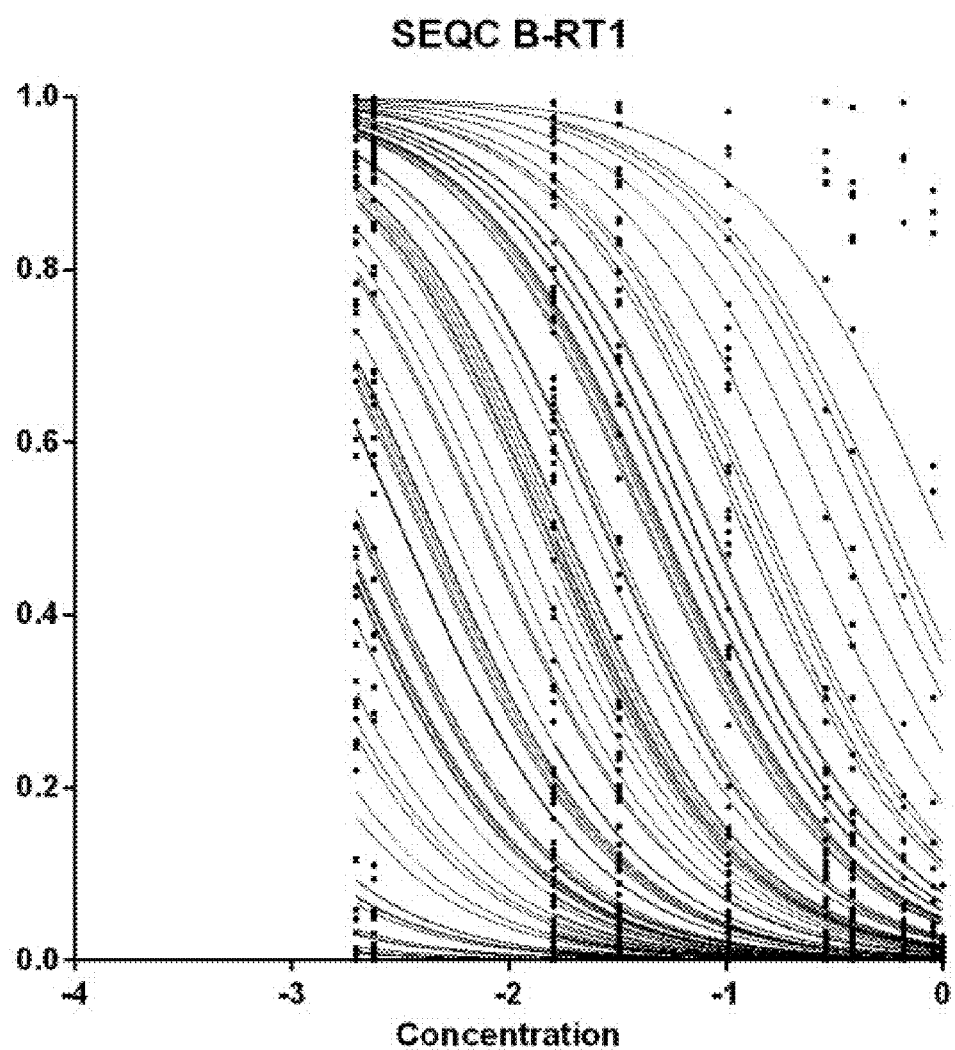
Figure 2E:
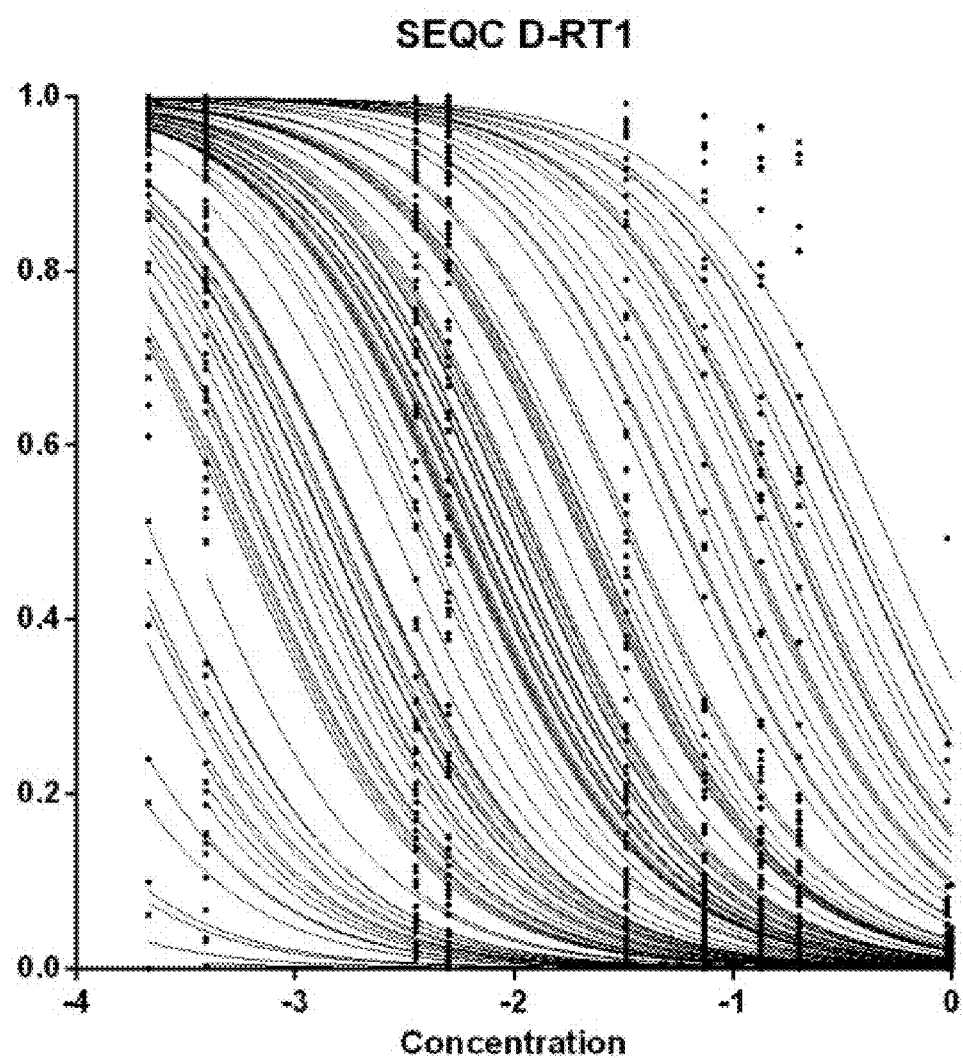
Figure 2F:
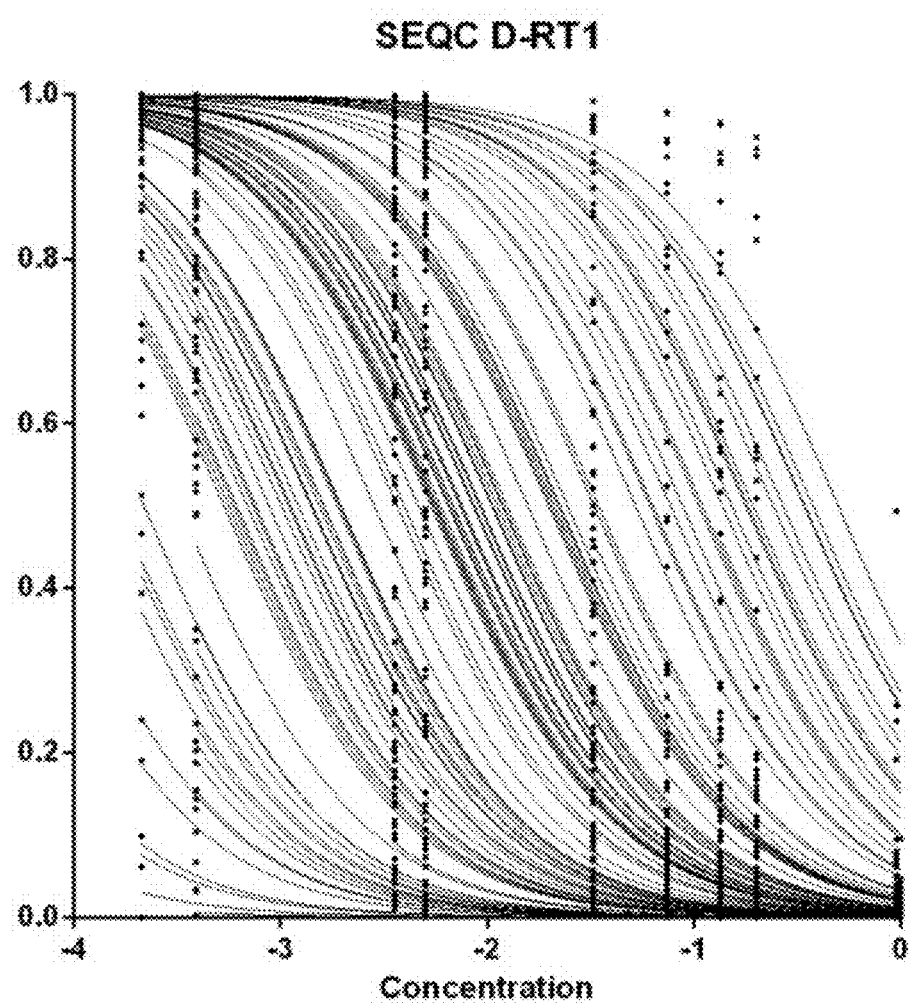

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

Described herein are methods for evaluating nucleic acids, and applications and business methods employing such compositions and methods. Some aspects of the present disclosure relate to improvements upon the Willey and Willey et al. U.S. Pat. Nos. 5,043,390; 5,639,606; 5,876,978 and 7,527,930, which are expressly incorporated herein by reference.

Methods for Assessing a Nucleic Acid

Described herein are methods for assessing amounts of a nucleic acid in a sample. In some embodiments, the method allows measurement of small amounts of a nucleic acid, for example, where the nucleic acid is expressed in low amounts in a specimen, where small amounts of the nucleic acid remain intact and/or where small amounts of a specimen are provided.

"Specimen" as used herein can refer to material collected for analysis, e.g., a swab of culture, a pinch of tissue, a biopsy extraction, a vial of a bodily fluid e.g., saliva, blood and/or urine, etc. that is taken for research, diagnostic or other purposes from any biological entity.

Specimen can also refer to amounts typically collected in biopsies, e.g., endoscopic biopsies (using brush and/or forceps), needle aspirate biopsies (including fine needle aspirate biopsies), as well as amounts provided in sorted cell populations (e.g., flow-sorted cell populations) and/or micro-dissected materials (e.g., laser captured micro-dissected tissues). For example, biopsies of suspected cancerous lesions in the lung, breast, prostate, thyroid, and pancreas, commonly are done by fine needle aspirate (FNA) biopsy, bone marrow is also obtained by biopsy, and tissues of the brain, developing embryo, and animal models may be obtained by laser captured micro-dissected samples.

"Biological entity" as used herein can refer to any entity capable of harboring a nucleic acid, including any species, e.g., a virus, a cell, a tissue, an in vitro culture, a plant, an animal, a subject participating in a clinical trial, and/or a subject being diagnosed or treated for a disease or condition.

"Sample" as used herein can refer to specimen material used for a given assay, reaction, run, trial and/or experiment. For example, a sample may comprise an aliquot of the specimen material collected, up to and including all of the specimen. As used herein the terms assay, reaction, run, trial and/or experiment can be used interchangeably In some embodiments, the specimen collected may comprise less than about 100,000 cells, less than about 10,000 cells, less than about 5,000 cells, less than about 1,000 cells, less than about 500 cells, less than about 100 cells, less than about 50 cells, or less than about 10 cells.

In some embodiments, assessing, evaluating and/or measuring a nucleic acid can refer to providing a measure of the amount of a nucleic acid in a specimen and/or sample, e.g., to determine the level of expression of a gene. In some embodiments, providing a measure of an amount refers to detecting a presence or absence of the nucleic acid of interest. In some embodiments, providing a measure of an amount can refer to quantifying an amount of a nucleic acid can, e.g., providing a measure of concentration or degree of the amount of the nucleic acid present. In some embodiments, providing a measure of the amount of nucleic acid refer to enumerating the amount of the nucleic acid, e.g., indicating a number of molecules of the nucleic acid present in a sample. The "nucleic acid of interest" may be referred to as a "target" nucleic acid, and/or a "gene of interest," e.g., a gene being evaluated, may be referred to as a target gene. The number of molecules of a nucleic acid can also be referred to as the number of copies of the nucleic acid found in a sample and/or specimen.

As used herein, "nucleic acid" can refer to a polymeric form of nucleotides and/or nucleotide-like molecules of any length. In certain embodiments, the nucleic acid can serve as a template for synthesis of a complementary nucleic acid, e.g., by base-complementary incorporation of nucleotide units. For example, a nucleic acid can comprise naturally occurring DNA, e.g., genomic DNA; RNA, e.g., mRNA, and/or can comprise a synthetic molecule, including but not limited to cDNA and recombinant molecules generated in any manner. For example the nucleic acid can be generated from chemical synthesis, reverse transcription, DNA replication or a combination of these generating methods. The linkage between the subunits can be provided by phosphates, phosphonates, phosphoramidates, phosphorothioates, or the like, or by nonphosphate groups, such as, but not limited to peptide-type linkages utilized in peptide nucleic acids (PNAs). The linking groups can be chiral or achiral. The polynucleotides can have any three-dimensional structure, encompassing single-stranded, double-stranded, and triple helical molecules that can be, e.g., DNA, RNA, or hybrid DNA/RNA molecules.

A nucleotide-like molecule can refer to a structural moiety that can act substantially like a nucleotide, for example exhibiting base complementarity with one or more of the bases that occur in DNA or RNA and/or being capable of base-complementary incorporation. The terms "polynucleotide," "polynucleotide molecule," "nucleic acid molecule," "polynucleotide sequence" and "nucleic acid sequence," can be used interchangeably with "nucleic acid" herein. In some specific embodiments, the nucleic acid to be measured may comprise a sequence corresponding to a specific gene.

In some embodiments the specimen collected comprises RNA to be measured, e.g., mRNA expressed in a tissue culture. In some embodiments the specimen collected comprises DNA to be measured, e.g., cDNA reverse transcribed from transcripts. In some embodiments, the nucleic acid to be measured is provided in a heterogeneous mixture of other nucleic acid molecules.

The term "native template" as used herein can refer to nucleic acid obtained directly or indirectly from a specimen that can serve as a template for amplification. For example, it may refer to cDNA molecules, corresponding to a gene whose expression is to be measured, where the cDNA is amplified and quantified.

The term "primer" generally refers to a nucleic acid capable of acting as a point of initiation of synthesis along a complementary strand when conditions are suitable for synthesis of a primer extension product.

General Description of Method

The preparation of a sequencing library involves some combination, or all, of the following steps: 1) nucleic acid fragmentation; 2) in vivo cloning, which serves to attach flanking nucleic acid adaptor sequences; 3) in vitro adaptor ligation; 4) PCR based adaptor addition; and, 5) unimolecular inversion probe type technology with, or without, polymerase fill-in, and ligation of probe to capture the sequence by circularization, with adaptor contained within the probe sequence.

The definition of "nucleic acid adaptor" is that the "nucleic acid adaptor" can serve as any or all of the following: a) sequencing primer recognition site, b) barcode sequence of nucleotides to deconvolute the sample that was prepared for sequencing during analysis, and c) universal nucleic acid site which allows for multi-template amplification, or further addition of fusion-tail sequences through amplification.

The prepared sequencing library from one or more of steps 1-5 above is then analyzed on a sequencing instrument, and a representative sampling of the library is sequenced. The number of times that each unique nucleic acid target is observed then is counted, and the relative proportion between each unique nucleic acid targets' counts is assessed. This relative proportion, however, does not represent the true proportionality of abundance between each unique nucleic acid target in the original sample.

This loss of original representation is a technical artifact (e.g., error, bias) of steps 1-5. Further, this error is non-systematic, i.e., not the same amount of bias, between at least the following errors: i) library preparation steps (1-5 above); ii) preparation sequencing library replicates; iii) different time of replicates; iv) different technicians preparing the library; and/or, v) preparing the library in a different laboratory.

As this non-systematic error in proportion of nucleic acid, in effect, targets the errors (i-v), any comparison of results between library preparations for the same sample are prone to error, thus limiting the application of sequencing as a tool for cost-effectively as well as reliably measuring nucleic acid copies.

One embodiment described herein is a method which utilizes a mixture of a known number (i.e., abundance, concentration and/or amount) of internal standard nucleic acid molecules corresponding to unique nucleic acid targets (also defined as 'native target" or NT) which are to be mixed in a nucleic acid sample prior to preparation of library for sequencing, or prior to sequencing (if library preparation is not required).

Each nucleic acid target is similar to its respective internal standard, with the exception of one or more changes to the nucleic acid sequence. These differences between native target and internal standard are identifiable with sequencing, and can include deletions, additions, or alteration to the ordering or composition of nucleotides used.

By introducing internal standards in a sample of nucleic acid targets prior to library preparation, the non-systematic error introduced by steps 1-5 (as well as sequencer instrument specific bias) is experienced by both the native target and the internal standard target similarly.

At the end of the sequencing, the proportion of sequencing events, (i.e., observations, counts, reads) between the native target and its respective internal standard is assessed, along with the original number of internal standard nucleic acid molecules input into the sample prior to library preparation, in order to quantifiably determine the original amount of each native target in the original sample prior to library preparation and sequencing.

As the inclusion of internal standard thus controls for error and relative changes in proportion between native targets during steps 1-5 and subsequent sequencing, the method described herein also enables low-abundance native targets to be preferentially amplified (i.e., enriched) relative to higher-abundance native targets during library preparation. This preferential amplification or enrichment can be harnessed so that at the end of sequencing library preparation, the relative proportion between each unique native target will converge towards an equimolar (i.e., uniform) abundance in the library. This results in more equal coverage of sequencing depth between native targets. And, since the internal standard experiences the preferential amplification or enrichment as well, this method allows the original amount of each native target in the original sample to be quantifiably determined prior to library preparation.

In one non-limiting example, for every 10-fold reduction in depth of proportion between native targets, an approximate 10-fold reduction in direct sequencing cost is achieved, because 10-fold fewer sequencing reads are required.

The addition of a mixture of nucleic acid standards prior to sequencing library preparation (or prior to sequencing if library preparation is not required) thus provides an accurate quantification of native targets at end point with sequencing.

The use of a standardized mixture of nucleic acid internal standards enables a direct comparison of results between laboratories for nucleic acid molecular diagnostics and other quantitative sequencing results.

Also, in certain embodiment, the further addition of internal standards enables the convergence of native target abundance, thus reducing the direct sequencing costs by the fold-proportion native target abundances are normalized towards each other.

The inclusion of a mixture of internal standard nucleic acid of known amount (i.e., abundance, concentration and/or number) during library preparation provides certain advantages. Since it might not be known which of the steps 1-5 or sequencing might introduce error, the present method reduces this bias, thus enabling inter-library and inter-laboratory comparison of results, and at the same time, provides the ability to reduce direct-sequencing cost through nucleic acid target convergence of concentration.

In certain embodiments, the method described herein includes a known number of internal standard molecules for each gene to be measured in nucleic acid sample prior to sequencing, or prior to preparation of library for sequencing.

Also, in certain embodiments, the preparation of a standardized mixture of internal standards can be used by multiple laboratories, thereby increasing reliability of measurement of each targeted gene and increasing inter-experimental and inter-laboratory reproducibility of measurement. The measurement of copy number for each nucleic acid relative to a known number of copies of its respective internal standard molecules within a standardized mixture of internal standards, and use of the same SMIS across experiments and laboratories, thus increases the reliability and quality control by controlling for variation introduced by preparation of sequencing library.

In certain embodiments, the method described herein uses a gene specific reverse transcription and/or a PCR for library preparation for quantification by sequencing. In certain embodiments, the optimization of PCR enables the multiplexing of up 100, 300, 500, 1000, or more genes to yield sufficient PCR product of each targeted gene for quantification by sequencing. The optimization of PCR can bring about a convergence of initial inter-gene transcript representation by 10-fold, 100-fold, 1000-fold, 10,000-fold, or greater while maintaining ability to quantify initial relative transcript representation through measurement of each gene relative to its respective internal standard. Thus, the inclusion of known number of copies of internal standards in sample prior to library preparation (or prior to sequencing if library preparation is not required) controls for subsequent changes in transcript representation. It is now possible to optimize inter-gene convergence without losing the information regarding initial representation. For example, in certain embodiments, there can be a convergence of more than 1000-fold, resulting in a reduction of "read" requirement from 10,000,000 to 10,000.

Also, in certain embodiments where each chip for a typical next generation sequencer enables 10 million reads, this result enables increasing the number of samples analyzed/chip from 1 to 1,000. Currently, since a chip for a typical sequencer costs $1,000, the chip cost/sample is thereby reduced from about $1,000 to about $1.00.

In addition, rare transcripts can be measured with statistical significance. For example, the number of copies of a nucleic acid corresponding to a gene transcript can be determined, e.g., the number of copies/cell, where the gene is expressed in low copy number. Enumerating less than about 1,000 molecules can allow measurement of less than about 10 copies/cell of at least 100 different gene transcripts in a small biological specimen. The methods are capable of measuring and/or enumerating less than about 10 copies/cell of at least 100 different gene transcripts in a small biological specimen.

In still some embodiments, more measurements can be obtained from a given specimen and/or sample, e.g., of the size typically used to measure that few copies of a nucleic acid corresponding to one gene. For example, practice of some embodiments can measure and/or enumerate less than about 100, less than about 50, less than about 20, less than about 10, less than about 8, or less than about 5 copies/cell of at least about 20, at least about 50, at least about 80, at least about 100, at least about 120, at least about 150, or at least about 200 different nucleic acids in a sample, e.g., corresponding to different gene transcripts.

The expressed material may be endogenous to the biological entity, e.g., transcripts of a gene naturally expressed in a given cell type, or the expressed material to be measured may be of an exogenous nature. For example, the methods can be used to quantify transfected genes following gene therapy and/or a reporter gene in transient transfection assays, e.g., to determine the efficiency of transfection.

EXAMPLES

The methods and embodiments described herein are further defined in the following Examples, in which all parts and percentages are by weight and degrees are Celsius, unless otherwise stated. Certain embodiments of the present invention are defined in the Examples herein. It should be understood that these Examples, while indicating preferred embodiments of the invention, are given by way of illustration only. From the discussion herein and these Examples, one skilled in the art can ascertain the essential characteristics of this invention and without departing from the spirit and scope thereof, can make various changes and modifications of the invention to adapt it to various usages and conditions.

The PCR-based NGS library preparation method incorporates competitive internal amplification controls (IAC). This method both controls for the majority of non-systematic errors introduced during NGS library preparation, and enables inter-laboratory comparison of quantitative NGS data.

The competitive IAC thus controls for non-systematic error in PCR-based NGS library preparation by sharing identical priming sites to a native nucleic acid template of interest so as to mimic the kinetics of the native target in the PCR reaction, and thus control for target-specific variation in PCR efficiency.

In methods described herein, since the competitive IAC experiences the same kinetics as a native nucleic acid template, the proportional relationship of native target sequencing reads to its respective competitive IAC does not change during NGS library preparation.

Moreover, when the concentration of the competitive IAC placed into the sample preparation is known, it is now possible to accurately calculate the original abundance of native nucleic acid molecules that was present at the start of NGS library preparation.

As one example, when multiple laboratories used the same mixture of competitive IAC in multiple different studies, each of the multiple laboratories has shown that its results are concordant.

Thus, use of competitive IAC in PCR-based NGS library preparation enables cost-effective highly multiplexed analyses of multiple nucleic acid targets across multiple samples with a high degree of accuracy and reproducibility.

An additional benefit of incorporating competitive IAC is that protocols which result in normalization (i.e., convergence) of each native target toward equimolar (i.e., uniform) concentration, such as Multiplex PCR, can be implemented using such method.

It is to be understood that with normalization of template concentrations, it is now possible that abundance between native nucleic acid templates may vary greater than one million fold. In the past, the most highly represented native nucleic acid template would be unnecessarily oversampled and sequenced ten million times in order to sequence the least represented nucleic acid template (e.g., at least ten times to accurately detect a 2-fold change (Power=80%; Type 1 error rate=0.05)). However, use of the competitive IAC method described herein provides for the normalization in representation of the target analytes, yet still retains quantitative information of the original representation of both low- and high-abundance targets with a low number of sequencing reads. The reduction in oversampling of over-represented nucleic acid targets thus results in reduced cost and stochastic sampling error associated with deep sequencing.

Example 1

Multiplex-PCR with Competitive IAC for NGS Library Preparation and Subsequent Measurement of Nucleic Acid Abundance Reference material RNA titration pools used in the FDA-sponsored Sequencing Quality Control (SEQC) project (which already have nucleic acid abundance measured by multiple qPCR, Microarray and NGS platforms under a variety of conditions) were obtained.

NGS libraries were prepared from the reverse transcribed reference material using Multiplex-PCR in the presence of primers and competitive IAC for 150-gene targets.

The NGS library preparation was evaluated using Multiplex-PCR with competitive IAC for reproducibility of nucleic acid abundance measurement within individual test sites, between laboratories, and across different nucleic acid measurement platforms.

The costs and advantages of Multiplex-PCR with competitive IAC for NGS library preparation were compared to a commonly employed Illumina-based NGS library preparation protocol and Taqman qPCR for accurately measuring nucleic acid abundance in a clinical setting.

Methods and Results

Forward and reverse primers were designed that correspond to 101 basepair regions (i.e., amplicon) for each of 150 uniquely transcribed genes in the human genome. Each primer was designed with a uniform 68° C. melting temperature. Each primer also contained a universal tail sequence that can be used for multi-template PCR, such as used in the addition of barcode and sequencing adaptor sequences after initial Multiplex-PCR. These primers were synthesized by Integrated DNA Technologies (IDT) and combined in equimolar ratio, and diluted to a final working concentration of 50 nMolar of each primer. A corresponding mixture of 150 competitive internal amplification controls (IAC) each 101 bases in length was synthesized by Integrated DNA Technologies (IDT). Each of the competitive IAC contained identical target-specific priming sites to their respective native nucleic acid template targets. Internal to these identical forward and reverse priming sites were six nucleotide changes in the internal portion of the sequence, so as to be able to differentiate a competitive IAC from its corresponding native target during post-sequencing data analysis.

Each competitive IAC was combined into a mixture at approximately equimolar concentration relative to each other by IDT. Because the mixing of competitive IAC may not have been in an exact 1:1 ratio, the absolute abundance of copies of each of the competitive IAC and their proportion in relation to each other for each of the 150 competitive IAC were determined by titration relative to a known amount of genomic DNA (gDNA) reference material. Genomic DNA reference material can serve as a normalizing reagent, because between each of the unique genomic sequences exist a one-to-one proportion to each other throughout the genome. Thus, perceived differences in competitive IAC concentration when titrated against gDNA, actually indicates a systematic difference in proportion that exists between competitive IAC in the mixture. This systematic difference is determined by the titration against a fixed amount of gDNA and is always applied to future calculations and measurements obtained using that particular lot or mixture of IAC (FIG. 1).

FIG. 1 shows the titration of a mixture of internal amplification controls (IAC) relative to a fixed amount of gDNA input of 100,000 copies into each Multiplex-PCR. Plotted on the Y-axis is the frequency or proportion of observed native reads divided by the sum of both native reads and its respective competitive IAC reads. On the X-axis is the initially estimated amount of each target in an approximately equimolar mixture of competitive IAC. 10 dilutions ranging from 10,000,000 copies of each IAC (Log 10 Concentration=0) to 1,000 (Log 10 Concentration=−2) copies were input into each of 10 reactions to generate the curve shown. Of the 150 designed primer sets, competitive IAC, and respective native targets, 119 titrated with a goodness of fit ($R^2$>0.95). Greater than 95% of the competitive IAC were within 10-fold of the expected equivalence point, (Native)/(Native+IAC)=0.5, when diluted to 100,000 copies (10,000,000 starting IAC copies diluted to 100,000, or Log 10 Concentration −2; i.e., 100-fold from 10,000,000). The new concentration served as the actual concentration for each of the 119 assays in the mixture of the competitive IAC and served as a reference of absolute accuracy (i.e., true accuracy) μg.

Thus, after testing the 150 assays against titrated mixture of IAC with fixed amount of gDNA, it was determined that 119 of the 150 assays had sufficient performance characteristics (Hill Plot $R^2$>0.95). These corrections were subsequently applied to all future measurements made with this mixture of IAC.

Phase III of the MAQC project, also known as the Sequencing Quality Control (SEQC) project, generated four pools from two RNA sample types: Universal Human Reference RNA (UHRR) from Stratagene and a Human Brain Reference RNA (HBRR) from Ambion. The four pools included the two reference RNA samples as well as two mixtures of the original samples: Sample A, 100% UHRR; Sample B, 100% HBRR; Sample C, 75% UHRR: 25% HBRR; and Sample D, 25% UHRR: 75% HBRR. This combination of biologically different RNA sources and known titration differences provided a method for assessing the accuracy of a platform based on the differentially expressed genes detected. Ten (10)$_k$g aliquots of these RNA pools were used for Samples A, B, C and D.

Each of the RNA titration pool reference materials (Samples A, B, C, D) were reverse transcribed, as described in Canales et al., 2006, with the exception that Superscript III reverse transcriptase from Invitrogen was used in place of MMLV reverse transcriptase and 1 μg of RNA was placed in each reverse transcription reaction. In addition, Sample A was reverse transcribed twice from two separate preparations of reverse transcription master mix, so as to determine variance introduced by reverse transcription on sequencing library preparation.

One (1) µL from each of these 5 reverse transcribed RNA Titration Pools of cDNA (Samples A-RT1, A-RT2, B, C and D), was spiked into 1 of 12 Multiplex-PCR reactions containing serially diluted mixture of competitive internal amplification control (IAC) mixture representing 150 targets. These 12 serial dilutions of mixtures of competitive IAC range from 107 copies loaded, all the way to 103. A total of 12 µL of each sample was consumed during Multiplex PCR, corresponding to ~133 ng of RNA in total for each sample.

The concentration where native material was in equal concentration to competitive IAC (i.e., the equivalence point) for each gene target was determined in each reverse transcribed reference material (Samples SEQC A-RT1, A-RT2, B, C and D), and was determined using the Hill equation (FIG. 2).

The graph in FIG. 2 shows the titration of a mixture of internal amplification controls (IAC) relative to a fixed amount of 100,000 copies gDNA, or 11 ng of Reverse Transcribed RNA cDNA material (Samples SEQC A-RT1, A-RT2, B, C and D), input into each Multiplex-PCR. Plotted on the Y-axis is the frequency or proportion of observed native reads divided by the sum of both native reads and its respective competitive IAC reads. On the X-axis is the initially estimated amount of each target in an approximately equimolar mixture of competitive IAC. Dilutions ranging from 10,000,000 copies of each IAC (Log 10 Concentration=0) to 1,000 (Log 10 Concentration=−2) copies were input into each of 10 reactions to generate the curve above.

Figure 3:
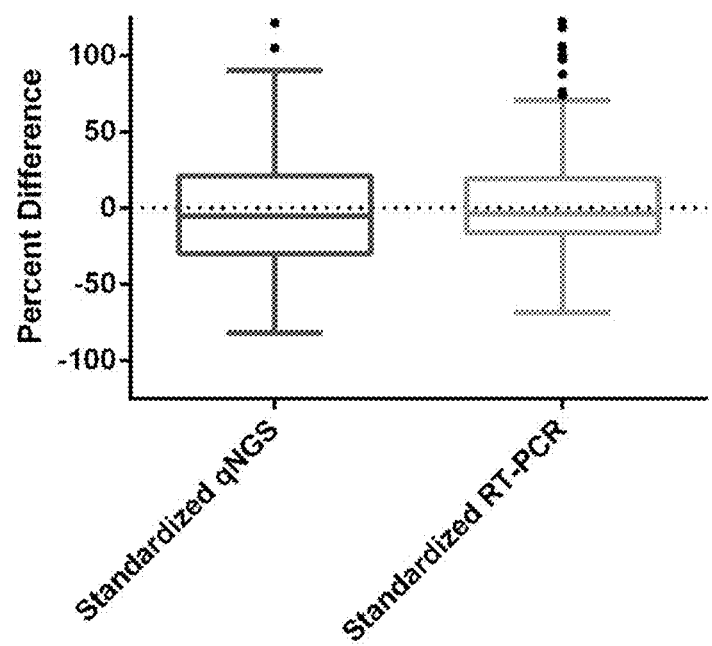
FIG. 3: Graphs showing analysis of assay accuracy. The values measured for SEQC Sample C-RT1 were compared to the values expected (% difference) based on measured SEQC Sample A and B values. The percent difference between the predicted signal C' and the actual assay signal C was used as an indication of relative assay accuracy (RA). An RA score $\Delta C$ for a target gene was defined as $(C-C'/C')$, respectively. The mean RA value (line), median quartiles (box), standard deviation (whiskers), and outliers are presented. The mean RA value was very close to the estimated value. Only certain assays has RA greater than 25% difference from the mean.

Since Samples C and D represent a known cross titration between Samples A and B, the accuracy of the platform differentially expressed genes was assessed (FIG. 3). The values measured for SEQC Sample C-RT1 were compared to the values expected (% difference) based on measured SEQC Sample A and B values. The percent difference between the predicted signal C' and the actual assay signal C was used as an indication of relative assay accuracy (RA). An RA score ΔC for a target gene was defined as (C−C'/C'), respectively. The distribution of percent difference from expected RA score for each gene is presented in a box plot for Standardized qNGS (n=88) and Standardized RT-PCR (n=201). Box plot components are: horizontal line, median; box, interquartile range; whiskers, 1.5× interquartile range; black squares, outliers.

Figures 4A, 4B:
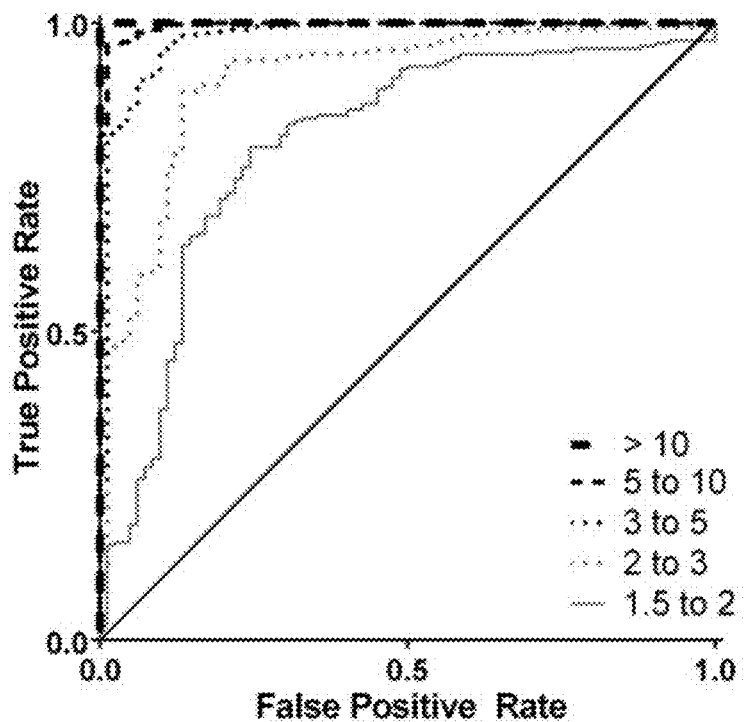
FIG. 4A: Graph showing gene targets (n=88) measured between Samples SEQC A-RT1, B, C evaluated for inter-gene differential expression (DE); i.e., whether their DE was between 1.5 to 3.0, 2 to 3, 3 to 5, 5 to 10, or greater than 10-fold in change. Control for false positive or negative change was assessed by comparing SEQC A-RT1 versus SEQC A-RT2.
FIG. 4B: Table 1 presenting the summary statistics for differential expression in Sample C compared to expected based on Samples A and B.

Gene targets (n=88) measured between Samples SEQC A-RT1, B, C, were evaluated for inter-gene differential expression (DE) (FIG. 4A); DE was between 1.5 to 3.0, 2 to 3, 3 to 5, 5 to 10, or greater than 10-fold in change. Control for false positive or negative change was assessed by comparing SEQC A-RT1 versus SEQC A-RT2. The summary statistics showing differential expression in Sample C compared to expected based on Samples A and B is shown in FIG. 4B—Table 1.

Figure 5:
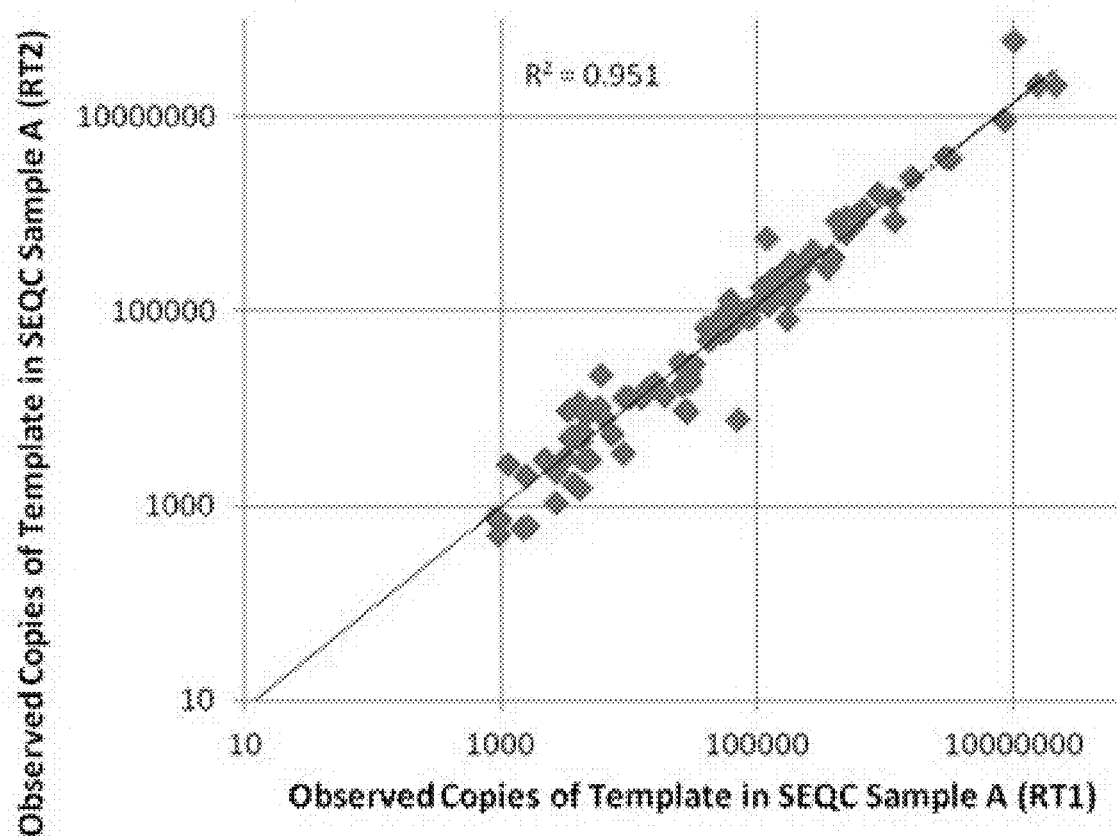
FIG. 5: Graphs showing assay reproducibility between Reverse Transcriptions. Two reverse transcriptions of SEQC Sample A (RT1 versus RT2) were measured for expression of 119 gene targets that successfully passed performance criteria in FIG. 1.

The assay reproducibility between reverse transcriptions is shown in FIG. 5. Two reverse transcriptions of SEQC Sample A (RT1 versus RT2) were measured for expression of 119 gene targets that successfully passed performance criteria in FIG. 1. Of the 119 gene targets, 97 had $R^2>0.95$ for curve fit of the Hill equation to determine equivalence point and concentration of each target (FIG. 2).

Figure 6:
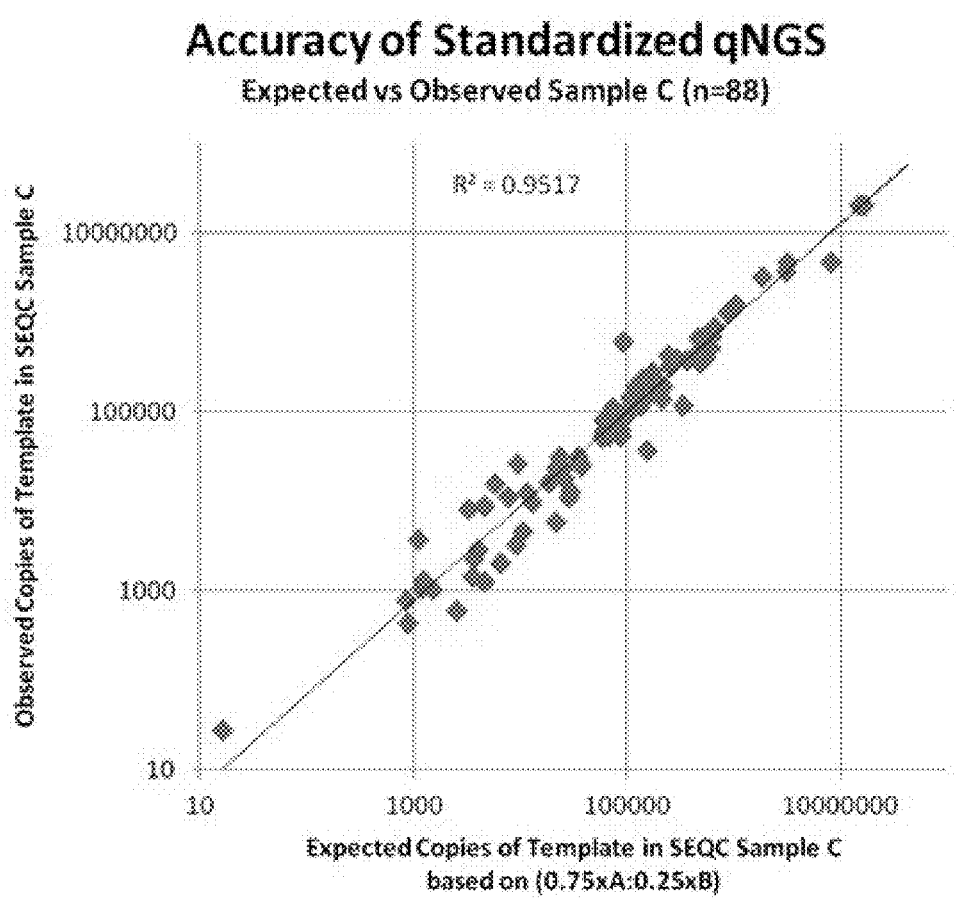
FIG. 6: Graph showing same data as in FIG. 3 and FIG. 4. Expected measurements in Sample C (x-axis) versus observed measurements (y-axis). Reverse transcription of SEQC Sample C were measured for expression of 119 gene targets that successfully passed performance criteria in FIG. 1. Of the 119 gene targets, 88 had $R^2 > 0.95$ for curve fit of the hill equation to determine equivalence point and concentration of each target (y-axis) (FIG. 2).

The same data as in FIG. 3 and FIG. 4 are depicted in FIG. 6. Expected measurements in Sample C (x-axis) versus observed measurements (y-axis). Reverse transcription of SEQC Sample C was measured for expression of 119 gene targets that successfully passed performance criteria in FIG. 1. Of the 119 gene targets, 88 had $R^2>0.95$ for curve fit of the hill equation to determine equivalence point and concentration of each target (y-axis) (FIG. 2).

Figure 7:
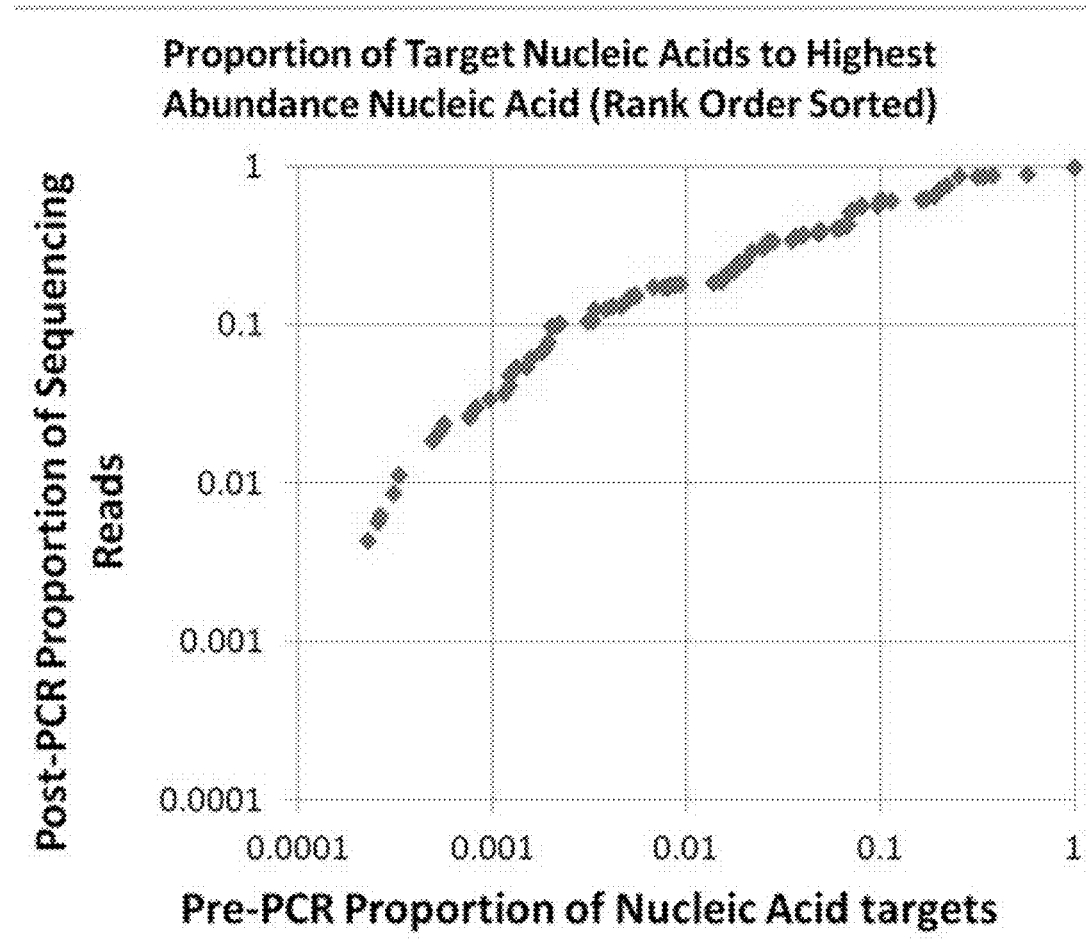
FIG. 7: Graph showing convergence and increased uniformity of 97 gene targets from FIG. 5. Plotted on the X-axis is the data from FIG. 5 in proportion to highest abundance template. On the Y-axis is the actual proportion of sequencing reads that gene-target is in proportion to highest sequence template.

The convergence and increased uniformity of 97 gene targets from FIG. 5 is shown in FIG. 7. Plotted on the X-axis is the data from FIG. 5 in proportion to highest abundance template. On the Y-axis is the actual proportion of sequencing reads that gene-target is in proportion to highest sequence template. Note that measurement and accuracy is not compressed (FIGS. 4-6), yet 75% of gene targets are within 10-fold sequencing read abundance to each other. That is, the sequencing depth decreased from approximately 1000-fold, down to 10-fold. This represents a 100-fold decrease in direct sequencing cost.

Figure 8:
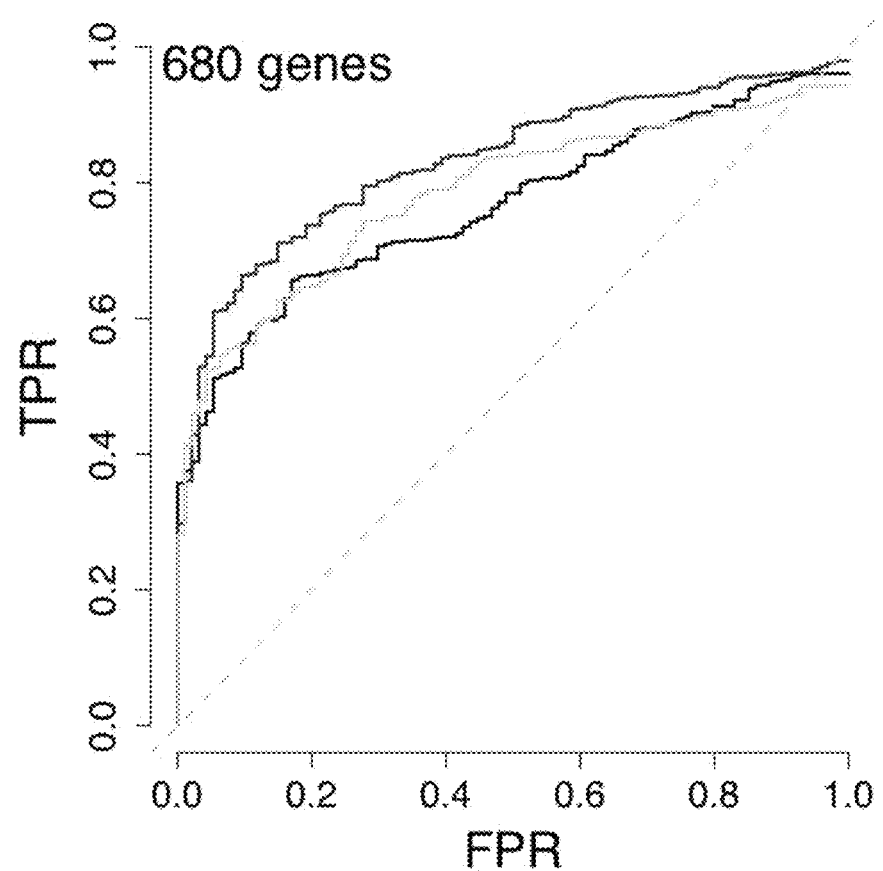
FIG. 8: Graph showing ROC curve to detect >3 fold change for RNA-Sequencing using Illumina platform from Bullard et al. BMC Bioinformatics 2010, 11:94.

The ROC curve to detect >3 fold change for RNA-Sequencing using Illumina platform from Bullard et al. BMC Bioinformatics 2010, 11:94 is shown in FIG. 8. Compared to FIG. 4B, this ROC curve represents an ~75% accuracy of RNA-seq to detect a >3 fold change. Whereas standardized qNGS described herein has a greater than 97% accuracy (FIG. 4B). It is to be noted that the standardized qNGS method utilized a 10-fold sequencing depth in order to accurately detect a 3 fold change over a 1000-fold proportion difference between native targets. In contrast, traditional RNA-sequencing would require 100-fold more reads to arrive at a similar accuracy. In one example, 5 million sequencing reads were utilized to accurately quantify 97 genes using the standardized qNGS method. In comparison, traditional RNA-sequencing would have required well over 500 million reads for accurate quantification.

Example 2

Quantitative Sequencing Following PCR-Driven Library Preparation with Internal Standard Mixtures has Improved Analytical Performance and Lower Cost Non-systematic biases introduced during preparation of next-generation sequencing (NGS) libraries as the primary source of technical variation have prevented application of NGS to measuring nucleic acid abundance in the clinical setting.

The costs of current qPCR clinical diagnostics are fixed to the cost of the chemistry (usually fluorescent) they use, and linearly associated with the number of nucleic acid targets they are interrogating. Further, each assay target requires a separate reaction vessel and multiple controls, which can become prohibitively expensive. These cumulative costs prevent the emergence of more complex clinical diagnostics based on measurement of multiple nucleic acid targets. More cost effective alternatives for multiplexed nucleic acid target abundance measurement are not as flexible in bringing new assay targets online cost-effectively without disrupting existing gene panels, or are not amenable to standardization and inter-site reproducibility of quantitative data. While NGS is amenable to cost-effective highly multiplexed quantitative analysis of multiple patient samples and nucleic acid targets there is a need for an efficient way to enable comparison of quantitative NGS results between sites, and to avoid the need for deep sequencing to accurately measure nucleic acid abundance.

In this example; a PCR-based NGS library preparation protocol that incorporated competitive internal amplification control (IAC) mixtures (i.e. internal standards) controlled for the majority of bias introduced during NGS library preparation, enabling clinical laboratories to offer cost effective moderately complex diagnostic panels from quantitative NGS data.

Reference material RNA titration pools used in the FDA-sponsored Sequencing Quality Control (SEQC) project were obtained (Samples A, B, C and D). Because the SEQC project RNA Samples C and D represent a known cross titration between SEQC project RNA Samples A and B, it is possible to compare SEQC expression value to measured and expected values for expression to determine accuracy of the method. Using Multiplex-PCR with primers and competitive IAC for 150-gene targets NGS libraries were prepared from: 1) gDNA to test general analytical performance, and 2) cDNA from reverse transcribed SEQC reference material to determine accuracy.

Results:

Using gDNA mixed with serially titrated competitive IAC mixtures as input, a linear dynamic range over $10^6$ orders of magnitude was observed, with an average $R^2$=0.995 (0.993-0.997; 95% CI). The correlation coefficient of expected versus observed for Sample C was $R^2$=0.96, and Sample D was $R^2$=0.94, with an ROC curve-determined accuracy to detect a 3-fold change of 97% (95-99%; 95% CI). Inter-site correlation coefficient of measurements based on only 400,000 sequencing reads was $R^2$=0.92 across a linear dynamic range of ~$10^5$ orders of abundance between native targets.

The method described herein overcomes key sources of non-systematic bias introduced during NGS library preparation. This enables reproducible inter-laboratory and inter-platform quantitative NGS results, and a clear path to regulatory approval for clinical diagnostic applications.

The method described herein (an NGS with Internal Amplification Controls (IAC)) provides intra-site and inter-site reproducibility of quantitative next-generation sequencing (NGS) data. The method described herein also reduces need for deep sequencing, and hence direct sequencing cost, by converging the number of reads required to adequately sequence both rare and high abundance nucleic acid targets.

Figure 9:
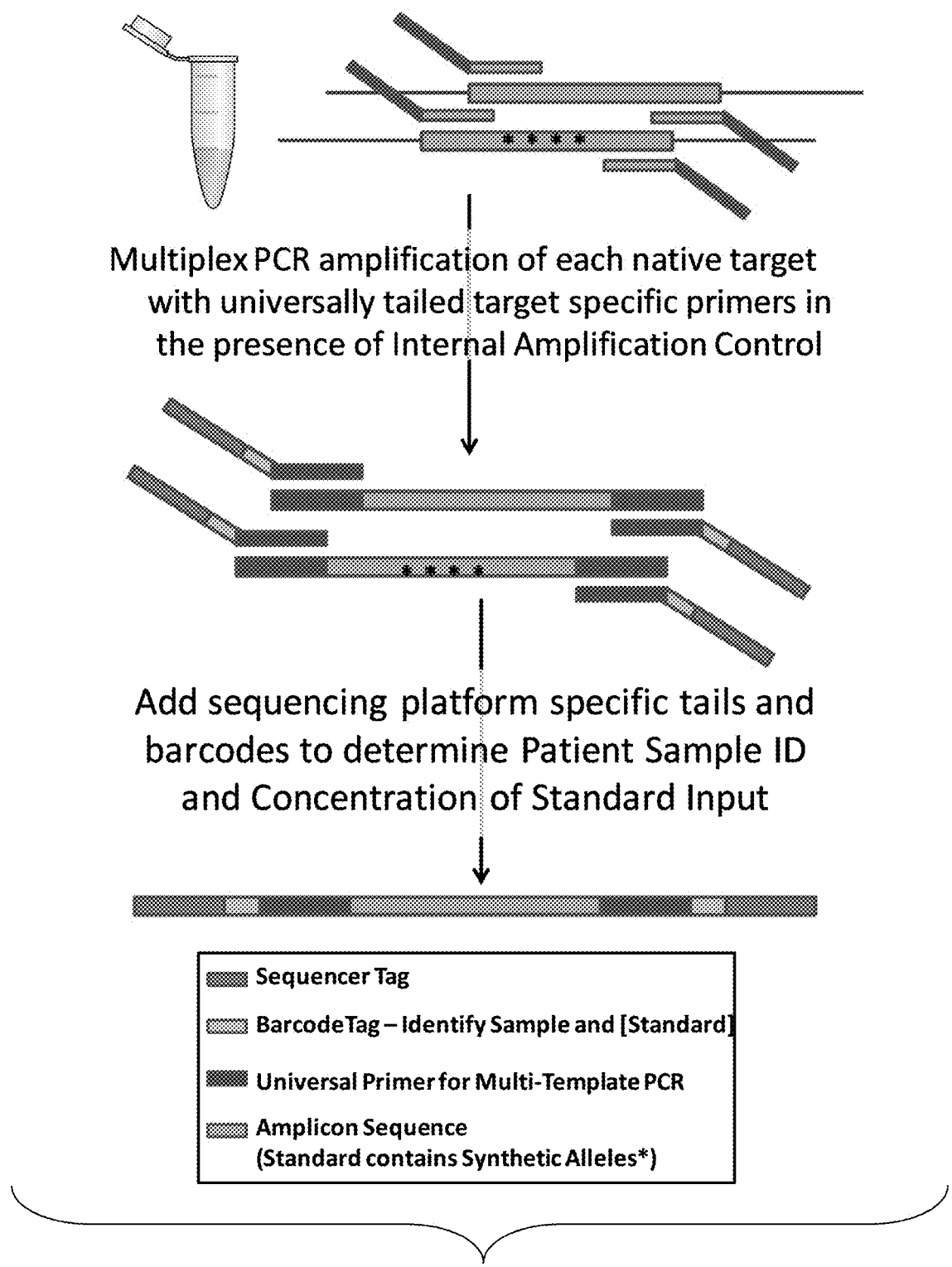
FIG. 9: Provides a schematic illustration of a PCR Master mix with a mixture of internal Amplification Controls (IAC).

FIG. 9 provides a schematic illustration of a PCR Master mix with a mixture of internal Amplification Controls (IAC). The IAC serves as a inter-library inter-site reference. The IAC is stable for a lengthy period of time (e.g., for years). The mixture of IACs control for PCR bias, and are present at a known concentration. The mixture of target specific primers includes hundreds of targets per reactions. The target specific primers contain a universal tail.

FIGS. 10A-10B are graphs showing the titration of a mixture of Internal Amplification Controls against gDNA and SEQC cDNA. The plot is in the format of a Dose-Response Curve for inhibition of an Enzymatic System. Taq polymerase is the enzyme. Inhibitor is the concentration of competitive Internal Amplification Controls (IAC). The dose-response is measured as the proportion of sequencing reads observed for the native genomic DNA (gDNA) or native complementary DNA (cDNA) target versus the sum of native and IAC sequencing reads. gDNA Plot represents 119 of 150 designed gene targets (~80% assay design success rate). The average correlation coefficient for fitting a three parameter fixed slope Hill Equation to each of the 119 assays was $R^2$=0.995 (0.993-0.997; 95% CI).

The average IC50 (Inhibitory Concentration 50%) was $10^{4.98}$ with number of gDNA copies input being $10^5$. Thus, titration of a mixture of internal amplification controls provides a true, not relative, accuracy of measuring copies of complex mixture of nucleic acids.

Figure 10:
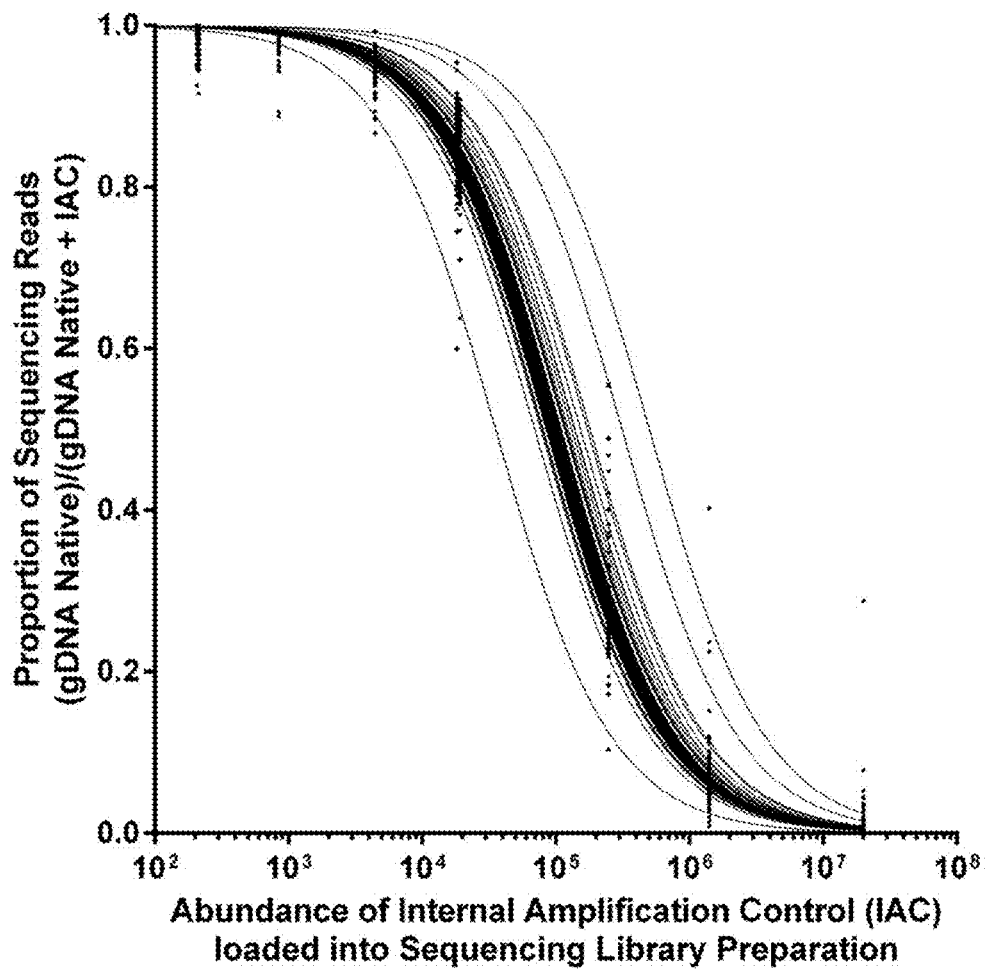
FIGS. 10-11: Graphs showing the titration of a mixture of Internal Amplification Controls against gDNA and SEQC cDNA.
Figure 11:
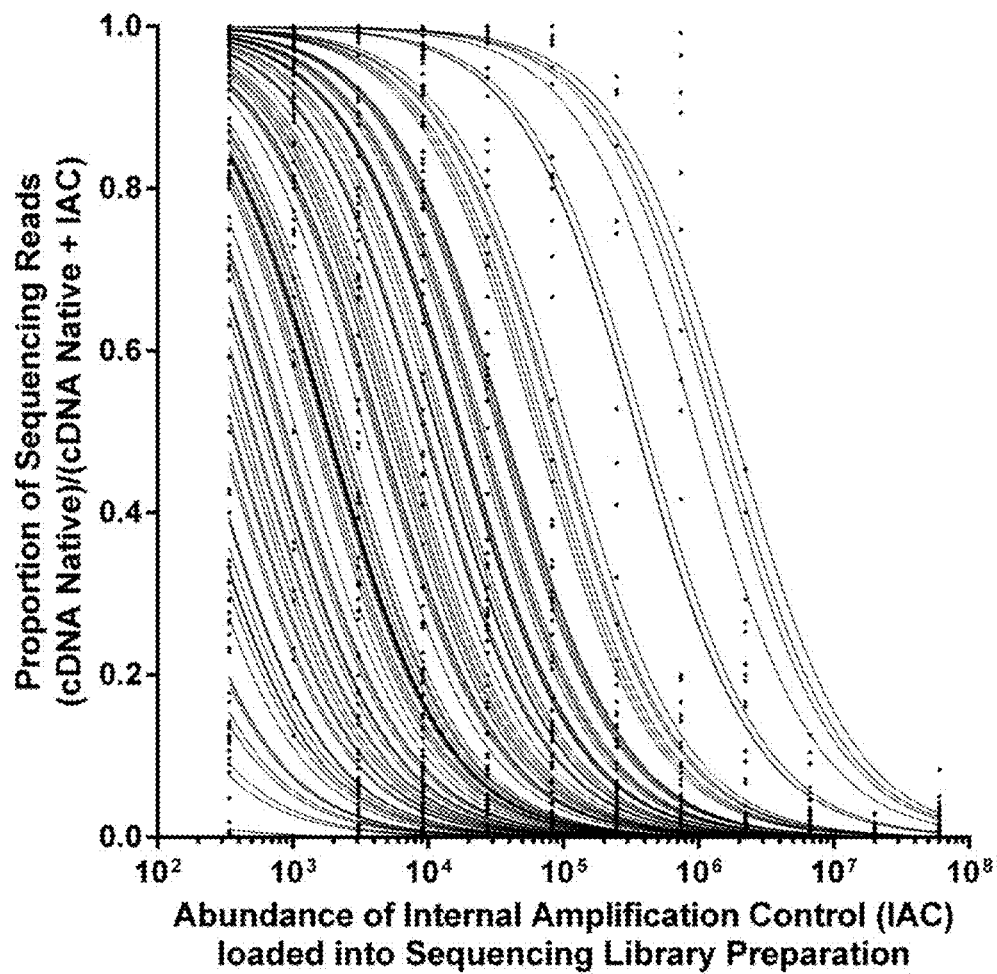
Figure 12:
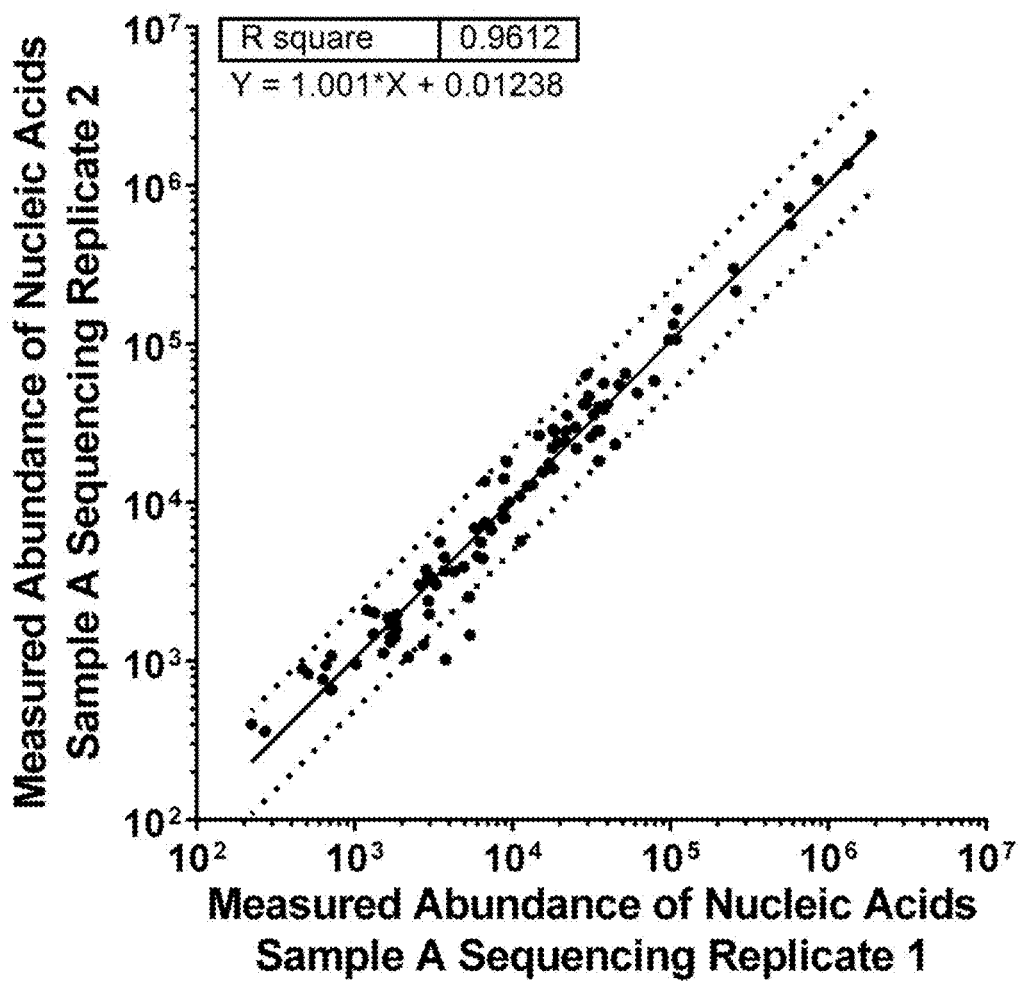
FIG. 12: Graph showing the same Library Preparation Replicate Sequencing (Intra-Site), where X-axis=1.8 million sequencing reads and Y-axis=3.0 million sequencing reads.

In FIGS. 10-11 (Result 1), the cDNA Plot represents 110 of 119 working gene target assays. Nine (9) assays had insufficient read depth of at least 1 sequencing read for both the native target as well as internal amplification control. The average IC50 (Inhibitory Concentration 50%) was determined for each nucleic acid target in SEQC Samples A, B, C and D under a variety of conditions and used in subsequent examples, Comparison of results were performed for:

FIG. 12 (Result 2) showing the same Library Preparation Replicate Sequencing (Intra-Site), where X-axis=1.8 million sequencing reads and Y-axis=3.0 million sequencing reads.

Figure 13:
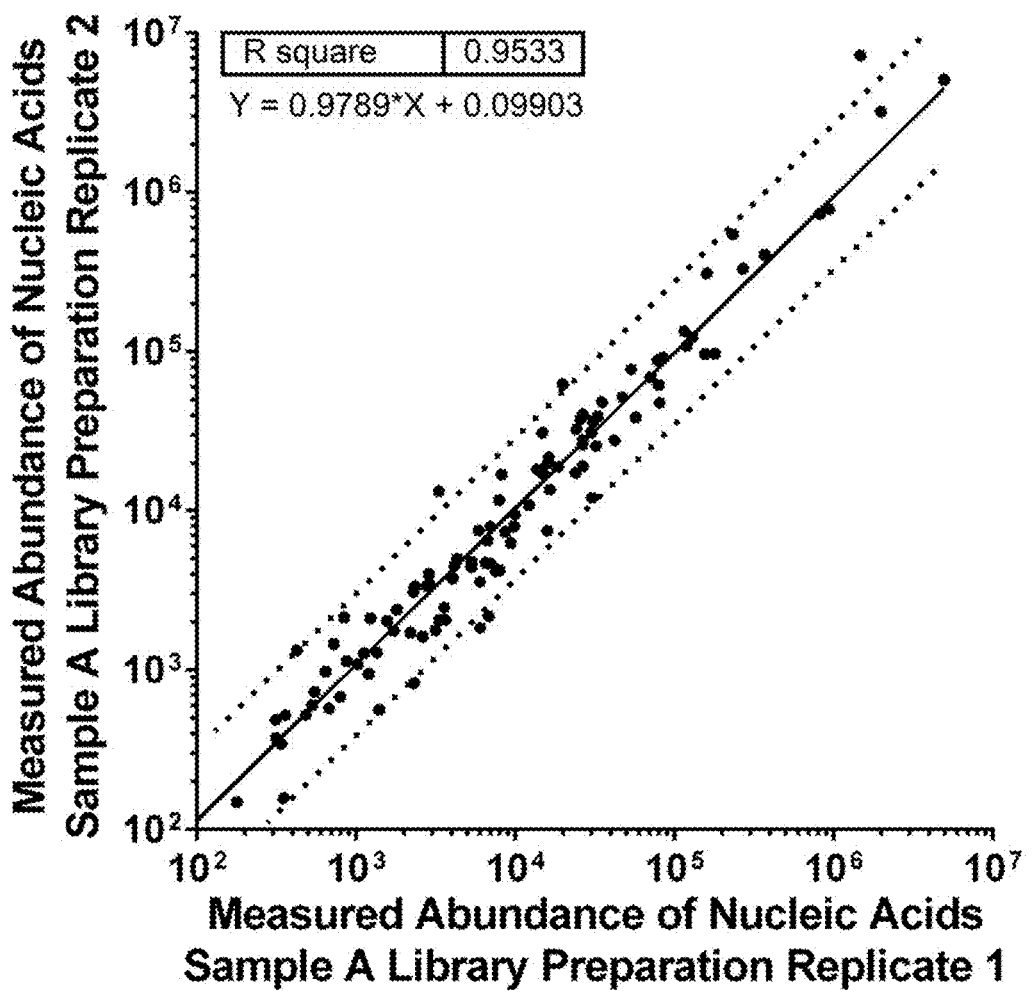
FIG. 13: Graph showing the separate Library Preparation Sequenced (Intra-Site), where X-axis=2.6 million sequencing reads and Y-axis=4.8 million sequencing reads.

FIG. 13 (Result 3) showing the separate Library Preparation Sequenced (Intra-Site), where X-axis=2.6 million sequencing reads and Y-axis=4.8 million sequencing reads.

Figure 14A:
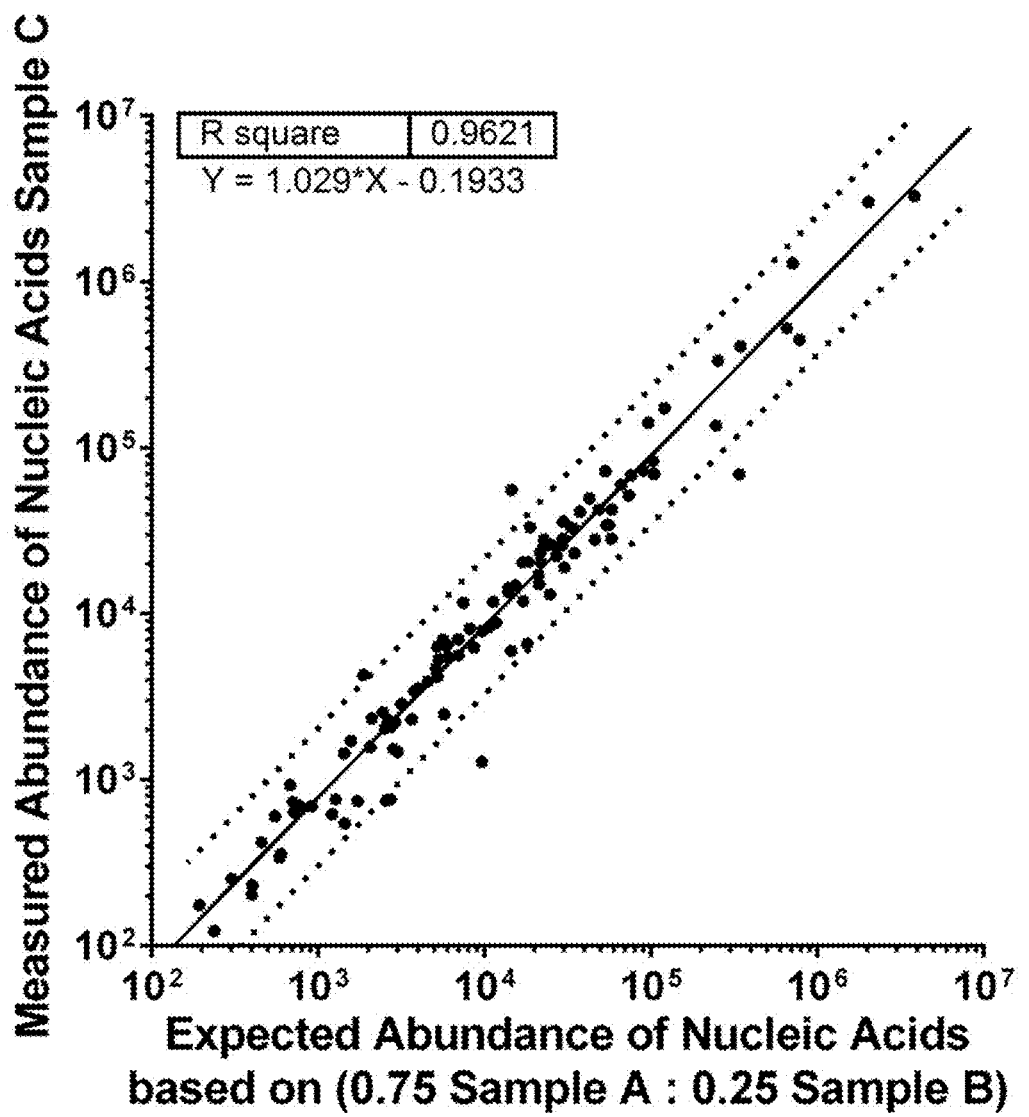
FIGS. 14A-14B: Graphs showing predicting measurement of Sample C and D based on measurements of Samples A and B (intra-site); where X-axis=15.2 million sequencing reads and Y-axis=4.9 million sequencing reads.
Figure 14B:
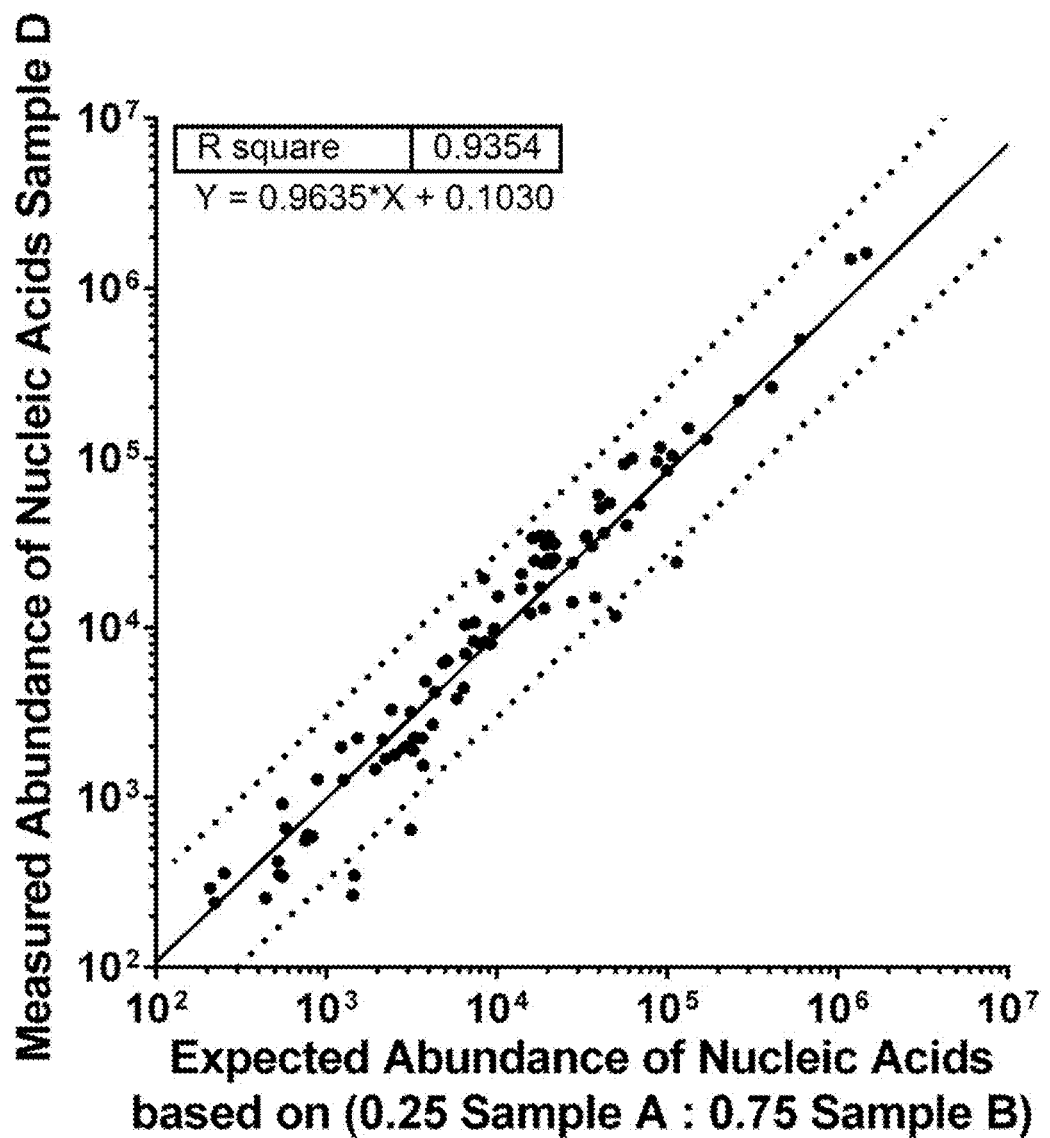

FIGS. 14A-14B (Result 4) showing predicting measurement of Sample C and D based on measurements of Samples A and B (intra-site); where X-axis=15.2 million sequencing reads and Y-axis=4.9 million sequencing reads.

Figure 15:
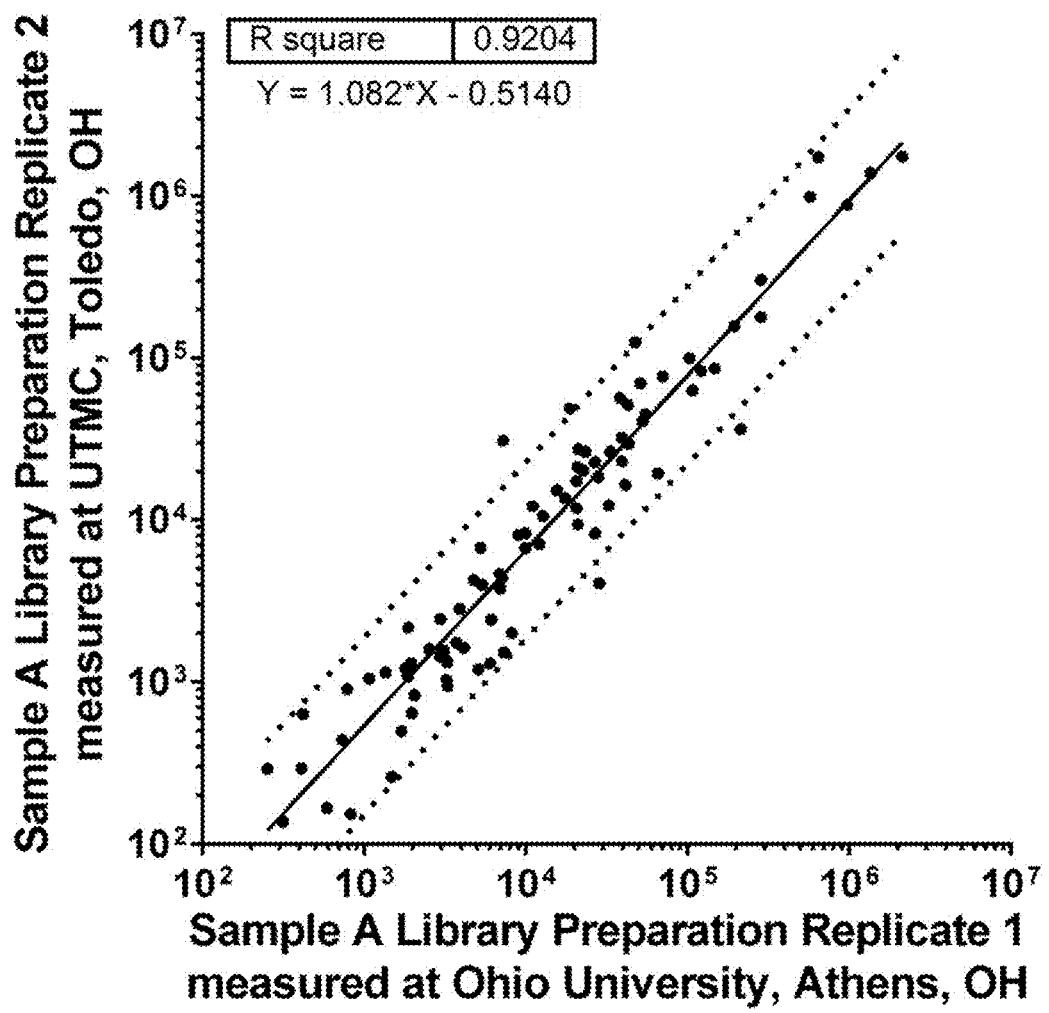
FIG. 15: Graph showing inter-laboratory comparison of measurements (inter-site), that is Separate Library Preparations Sequenced at Different Sites (Inter-Site) where X-axis=2.6 million sequencing reads and Y-axis=0.4 million sequencing reads.

FIG. 15 (Result 5) showing inter-laboratory comparison of measurements (inter-site), that is Separate Library Preparations Sequenced at Different Sites (Inter-Site) where X-axis=2.6 million sequencing reads and Y-axis=0.4 million sequencing reads.

Figures 4B, 16A, 16B:
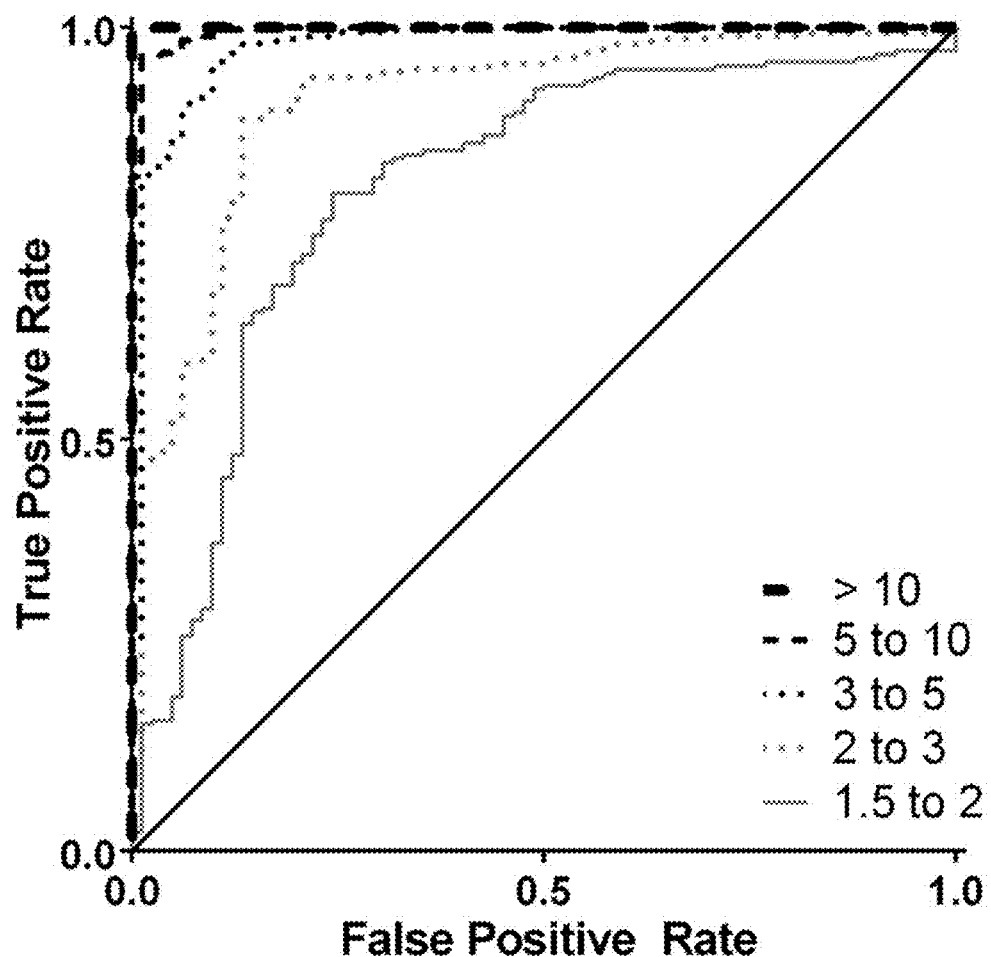
FIGS. 16A-16B: Graphs showing Receiver Curve to accurately detect fold changes based on FIG. 13 (Results 4), showing Receiver Curve to Call Differential Expression Based on FIG. 14—Results 4.

FIGS. 16A-16B (Result 6) showing Receiver Curve to accurately detect fold changes based on FIG. 13 (Results 4), showing Receiver Curve to Call Differential Expression Based on FIG. 14—Results 4.

Figure 17A:
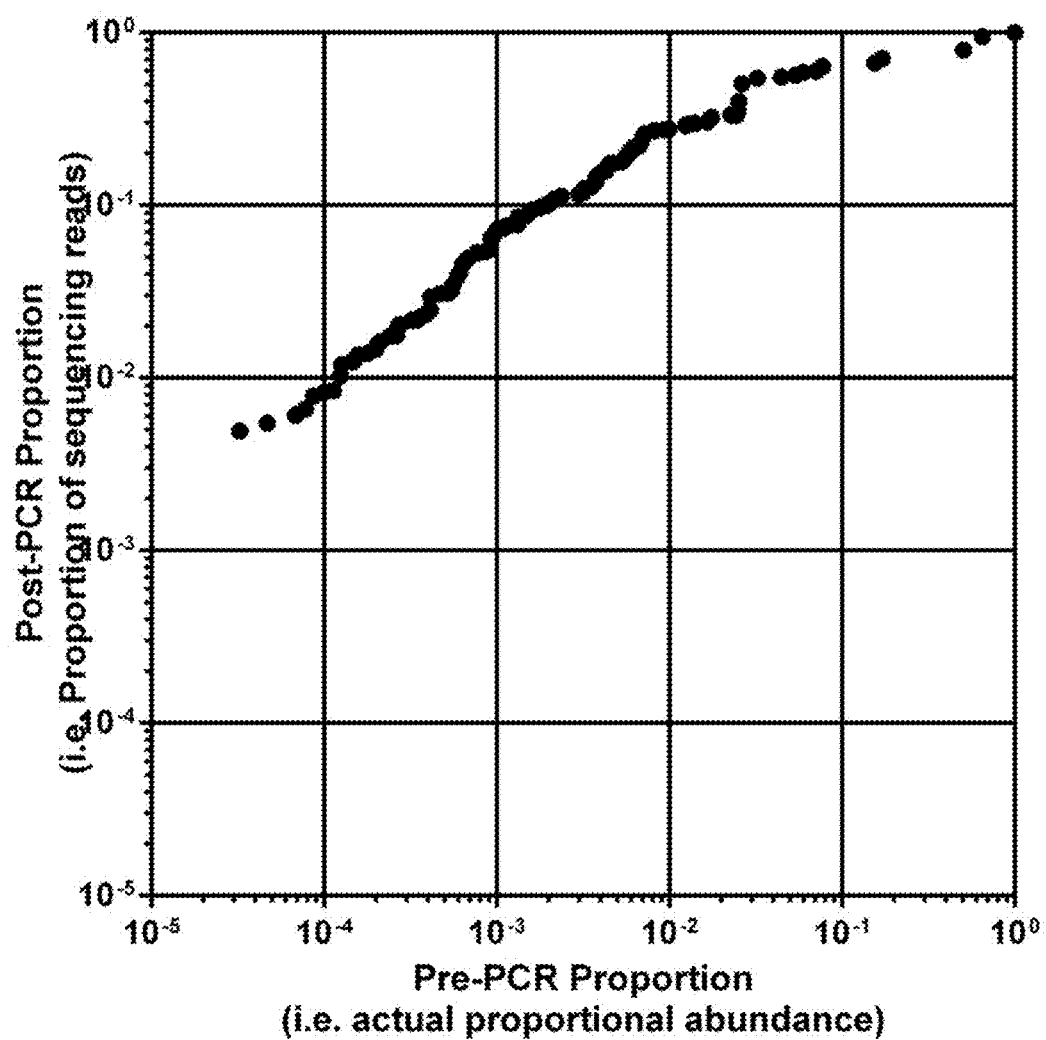
FIG. 17A-17B: Graph showing PCR-Driven Library Preparation Converges Native Target Concentrations Reducing Required Read Depth.
Figure 17B:
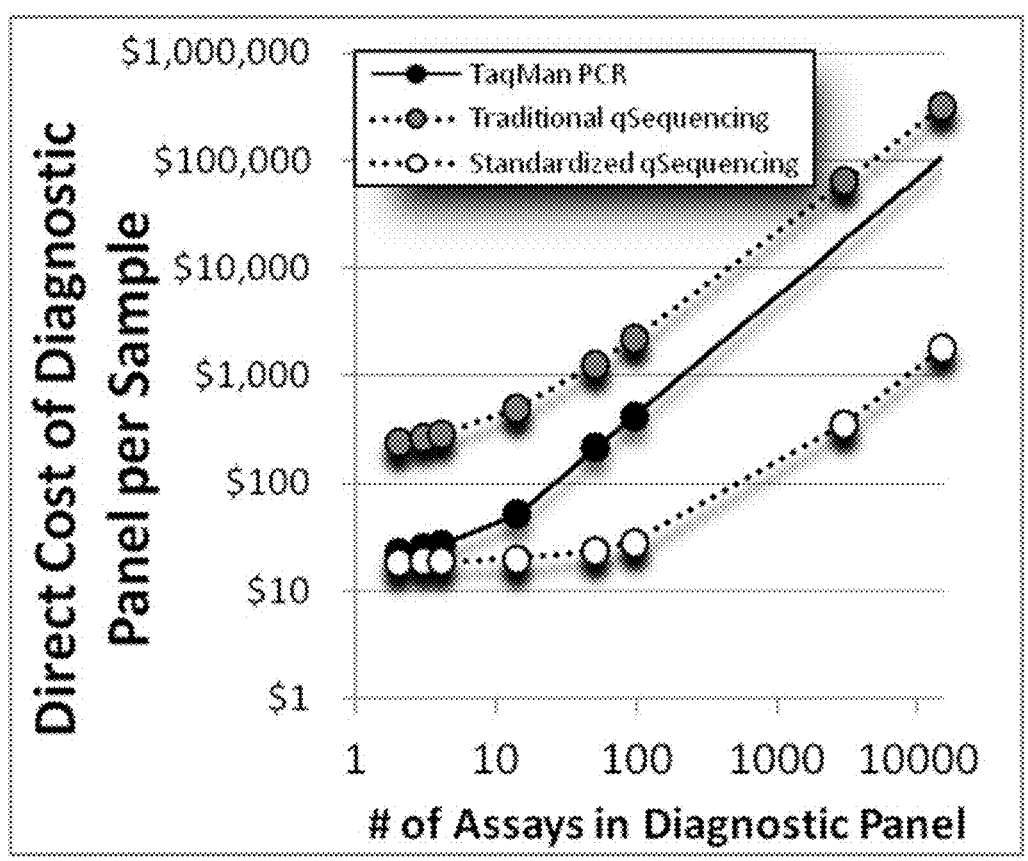

FIG. 17 (Result 7) showing PCR-Driven Library Preparation Converges Native Target Concentrations Reducing Required Read Depth. The convergence of Native Template Amplicon Concentrations during PCR driven library preparation reduces number of sequencing reads to adequately sequence all targets. The Internal Amplification Controls provide the necessary reference point at the beginning of PCR driven sequencing library preparation to accurately measure each nucleic acid target despite convergence of template concentration (See FIGS. 12-16—Results 2-6). In this example, direct sequencing depth is reduced by 1000-fold, and all targets are within 100-fold of each other.

It is also to be understood that it is within the contemplated scope of the present disclosure that the methods described herein include the use of moderate complexity clinical panels based on PCR-driven NGS library preparation with Internal Amplification Controls. Non-limiting examples include panels for: Lung Cancer Risk Test (15 gene); Lung Cancer Diagnostic Test (4 gene); Lung Cancer Chemo-Resist Test (20 gene), and BCR-ABL Fusion Transcript test (2 genes).

Example 3

STAndardized RNA SEQuencing (STARSEQ)

STAndardized RNA SEQuencing (STARSEQ) was assessed using two separate reference materials: 1) genomic DNA (gDNA) derived from the blood of a phenotypically normal individual (de-identified sample 723) at the University of Toledo Medical Center (UTMC) according to a protocol approved by the UTMC institutional review board, and 2) four reference RNA samples (A, B, C and D) provided by the FDA sponsored Sequencing Quality Control (SEQC) project (previously MAQC consortium). Sample A consists of Universal Human Reference RNA obtained from Stratagene. Sample B consists of Human Brain Reference RNA obtained from Ambion. For the SEQC project, samples A and B were then combined with Ambion External RNA Controls Consortium (ERCC) Spike-In Control RNA Mixes 1 and 2, respectively, so as to achieve a final concentration of 2% in samples A and B based on Total RNA concentration.

Each spike-in mix of ERCC RNA controls contains the same controls spanning a dynamic range greater than $10^6$, but in different formulations. Within each formulation mix are 4 subgroups that exhibit known fold differences in abundance between mix 1 and 2; 0.5×, 0.67×, 1.0× and 4.0×-fold difference. Samples A and B were then combined in 3:1 and 1:3 proportional mixtures to create samples C and D, respectively. The gDNA "reference" material represents a sample where the majority of endogenous targets are in a very close 1:1 proportion to each other. Whereas, samples A-D represent a complex mixture of synthetic (ERCC controls) and endogenous RNA targets in known proportions that can be used as ground truth benchmarks for assessing a method's analytical performance characteristics across a greater than $10^6$ fold dynamic range of abundances.

Reverse Transcription of RNA Reference Materials

Ten micrograms each of samples A-D reference RNA materials at a concentration of 1 µg/µL were obtained from the FDA sponsored SEQC project (fda.gov/ScienceResearch/BioinformaticsTools/Microarray Quality Control Project). For each sample two 2 µg aliquots of RNA were reverse transcribed. Each reverse transcription reaction took place in a 90 µL volume using manufacturer's protocol for Superscript III reverse transcription (Life Technologies) and oligo(dT) priming After reverse transcription, the two 90 µL cDNA products for each sample were combined into a single 180 µL volume (reverse transcription 1; RT1). For sample A, an additional set of two 2 µg aliquots of RNA were reverse transcribed using a separate master mix (reverse transcription 2; RT2).

STARSEQ Assay Target Selection

The MicroArray Quality Control (MAQC) consortium previously selected a list of 1,297 genes to evaluate performance of multiple qPCR and microarray platforms). From this list, 150 endogenous targets were selected to develop STARSEQ assays. These 150 assays were chosen, in part, because the gene targets they represent are expressed over a greater than $10^6$ dynamic range. These reagents were used to measure absolute as well as relative proportion of each gene target in gDNA and reverse transcribed reference RNA samples A-D. In addition, 28 of 92 External RNA Control Consortium (ERCC) targets were also selected to develop STARSEQ assays.

STARSEQ Primer Design and Synthesis

Forward and reverse PCR primers were designed to corresponding 101-bp amplicon regions for each of 150 uniquely transcribed genes in the human genome and 28 ERCC targets. Each forward and reverse primer set was designed with a uniform 68° C. melting temperature using Primer3 software (Untergasser et al, NAR, 2012). In order to minimize off-target priming, primer pair specificity was verified using GenomeTester 1.3 to identify any additional amplicons less than 1000 bp in size. Each primer also contains a universal tail sequence not present in the human genome, which can be used for multi-template PCR addition of barcode and platform specific sequencing adapters. The forward universal tails are identical in sequence adapters used for arrayed primer extension (APEX-2), while the reverse tail sequence is the same as the forward with the exception of the last four 3' bases, enabling directionality during sequencing. Target specific primers with universal tails for the 150 endogenous targets and 28 ERCC targets were synthesized by Integrated DNA Technologies (IDT) and Life technologies, respectively. A primer pool for endogenous or ERCC targets was created by combining synthesized primers in equimolar ratio, and diluting to a final working concentration of 50 nM for each primer in dilute Tris-EDTA buffer.

STARSEQ Competitive Internal Standard Mixture Design and Synthesis

Figure 18A:
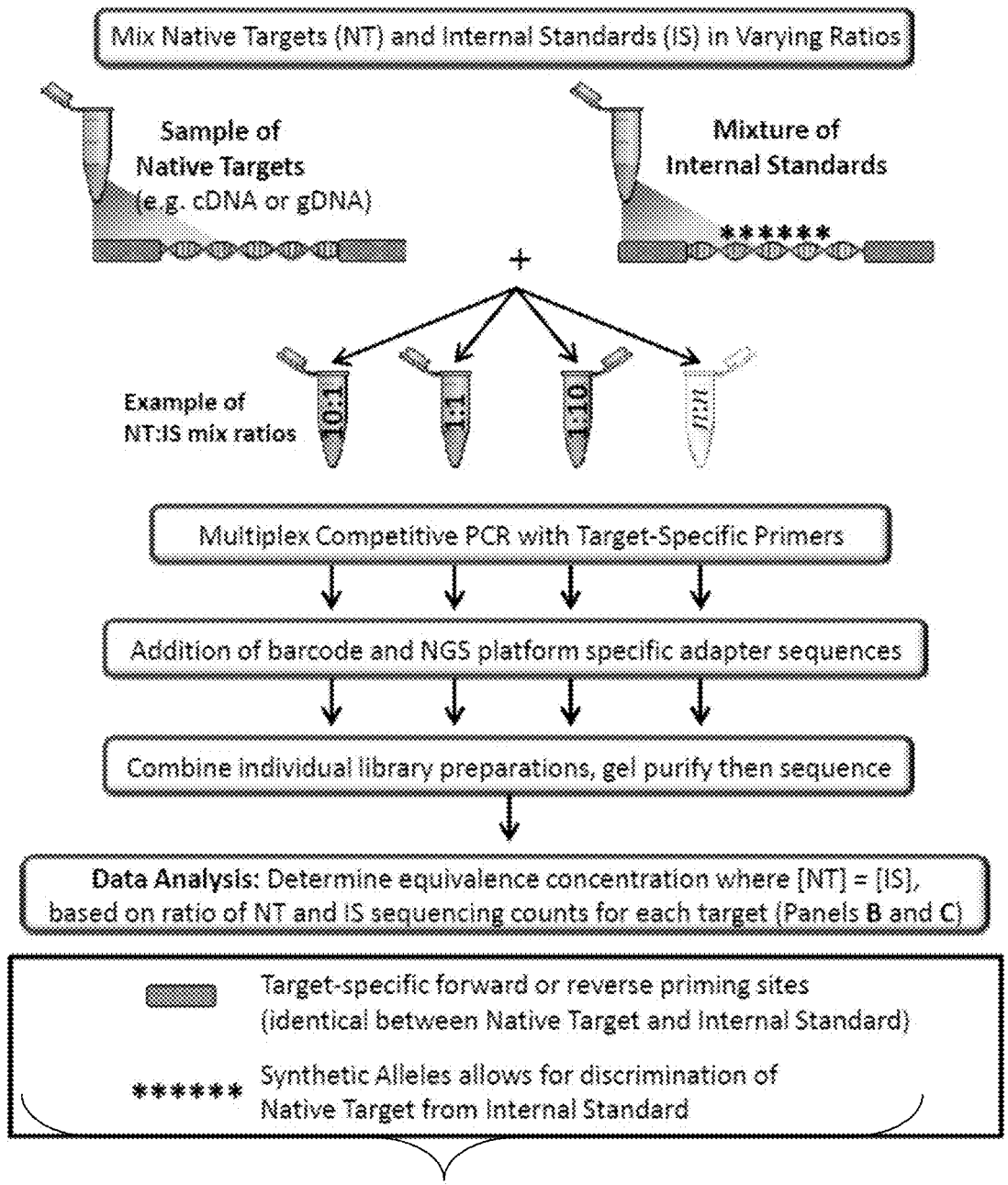
FIGS. 18A-18B: Standardized RNA Sequencing (STAR-SEQ) Workflow and Data Analysis
Figure 18B:
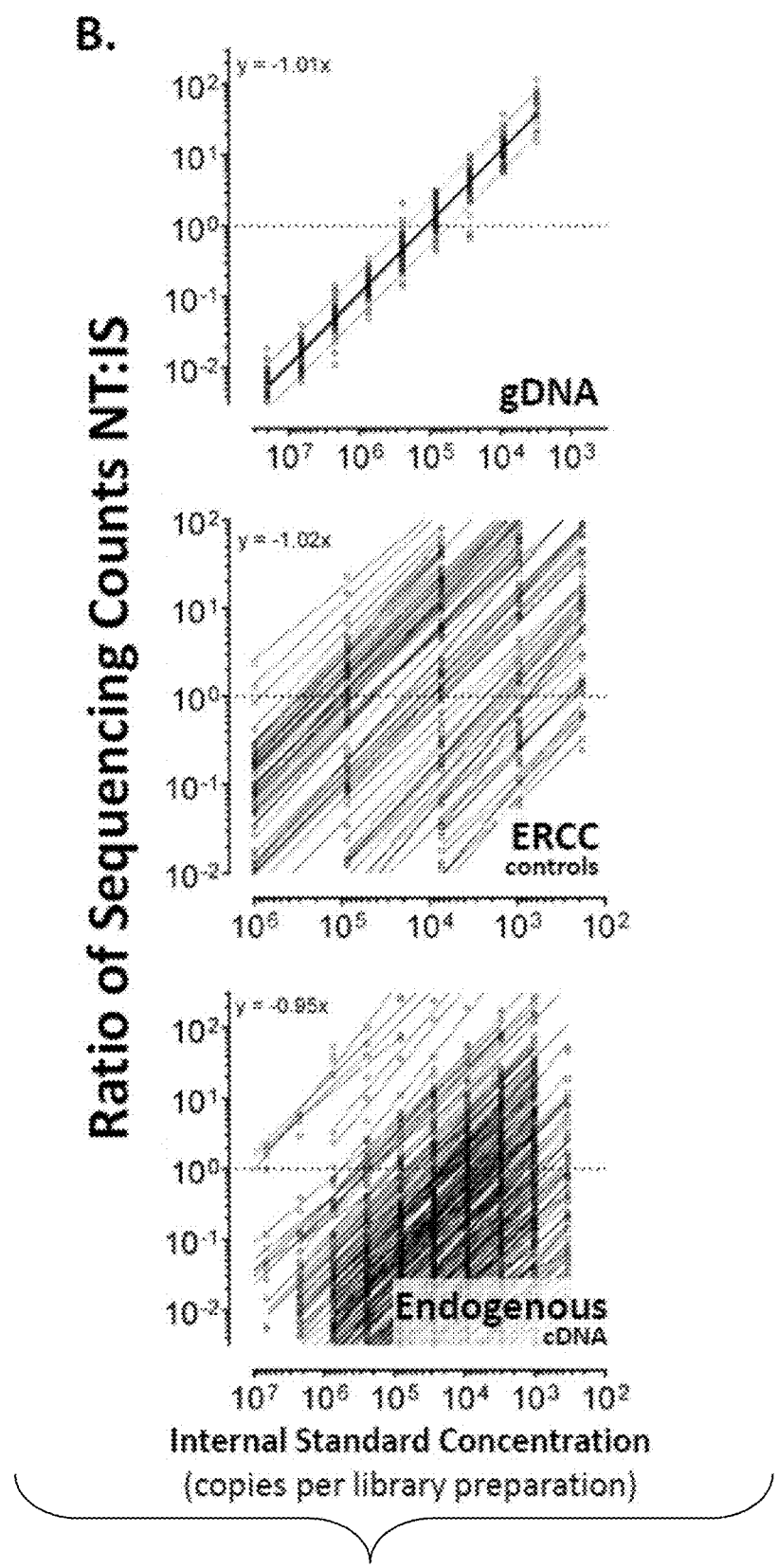

Each 101-bp competitive internal standard (IS) was designed to retain identical target specific priming sites to their respective native nucleic acid target (FIGS. 18A-18B). Internal to these identical priming sites are six nucleotide changes, so as to be able to differentiate a competitive IS from its corresponding native target during post-sequencing data analysis. The 150 competitive IS corresponding to the endogenous targets were synthesized by Integrated DNA Technologies (IDT), and the 28 competitive IS corresponding to ERCC targets were synthesized by Life Technologies.

For the 150 competitive IS templates corresponding to endogenous targets, concentration was measured by optical density at IDT, and subsequently combined in a 1:1 stochiometric molar ratio based on these measurements. Concentration of each IS was determined empirically by cross-titrating the mixture relative to a fixed gDNA input of 100,000 copies (ID 723). In gDNA from a phenotypically healthy individual, it is now believed that the majority of loci would be in a 1:1 proportion to each other, providing a reasonable and cost-effective reference material to determine the actual concentration for each competitive IS template.

For the 28 competitive IS templates corresponding to ERCC targets, no such reference material exists for normalization. Thus, each standard was separately amplified with forward and reverse primers (without universal sequences), column purified (QIAquick PCR purification kit), visualized and quantified for only a single peak at 101-bases on an Agilent 2100 Bioanalyzer using DNA Chips with DNA 1000 Kit reagents according to manufacturer's protocol (Agilent Technologies Deutschland GmbH, Waldbronn, Germany). Quantified standards were then combined in a 1:1 stochiometric molar ratio, to create a stock concentrated mixture of internal standards (IS). Both the endogenous and ERCC target mixtures of competitive IS were then serially diluted to working concentrations and used in all subsequent experiments as a reference mixture for quantifying absolute copies of each transcript in samples A-D (FIGS. 18A-18B).

Multiplex Competitive PCR with Universally Tailed Target Specific Primers

For each multiplex competitive polymerase chain reaction (PCR), a 10 µL reaction volume was prepared containing: 1 µL of native templates, 1 µL of competitive IS mixture at varying input concentrations, 1 µL of corresponding primer-mix, 1 µL of 2 mM dNTPs, 1 µL of 10× Idaho Technology reaction buffer with 30 mM $MgCl_2$, 0.1 µL of Promega GoTaq Hot Start Taq polymerase (5u/µL) and 4.9 µL of RNAse free water (FIG. 18A). Genomic DNA was spiked into 10 separate multiplex-PCR reactions containing serially diluted mixture of competitive IS mixture representing 150 endogenous targets. These 10 dilutions represent a series of 3-fold dilutions of IS mixture ranging in abundance from $2 \times 10^6$-$10^3$ copies loaded. Sample A-D cDNA for RT1 was spiked into 5 separate multiplex-PCR reactions containing serially diluted mixture of competitive IS mixture representing 28 ERCC targets. These 5 dilutions represent a series of dilutions of IS mixture; $10^6$, $10^5$, $10^4$, $10^3$ and 300 copies loaded. Reverse transcribed RNA for samples A (RT1 and RT2), B, C and D were spiked into 12 separate multiplex-PCR reactions containing serially diluted mixture of competitive IS mixture representing 150 endogenous targets.

These 12 dilutions represent a series of 3-fold dilutions of IS mixture ranging in abundance from $6 \times 10^7$-$3.4 \times 10^2$ copies loaded. A total of 17 μL of each cDNA sample was consumed during multiplex competitive PCR, corresponding to ~377 ng of RNA for each sample.

Standardized RNA Sequencing (STARSEQ) Workflow and Data Analysis

FIG. 18A NT=Native Target (e.g. cDNA, gDNA, etc.); IS=Internal Standard, a ssDNA or dsDNA molecule that a) is homologous to a specific native target at the primer sequences and therefore competes for amplification with the native target, but b) contains one or more base substitutions internal to the primer sites and therefore is distinguishable from the native target. The IS template for each gene is in a fixed relationship relative to the IS for the other genes in an internal standard mixture.

FIG. 18B shows the proportional relationship among native targets in the original sample is preserved during amplification and sequencing because a) the competition between each NT and its respective IS preserves the original concentration for each NT, and b) the IS are in a fixed relationship relative to each other. Determining the abundance of native target in the original sample is obtained by multiplying the ratio of sequencing counts for NT and IS (NT:IS) by the concentration of internal standard (IS) loaded into the amplicon library preparation (i.e., equivalence point determination). Native targets for which values could not be measured across at least three dilution points are not shown. FIG. 18B—upper panel: shows linearity of cross titrating competitive Internal Standard Mixture with constant amount of genomic DNA (gDNA) for 123 targets. Dotted lines represent 95% prediction interval for NT:IS ratio values. FIG. 18B—middle panel: shows the linearity of cross titrating competitive Internal Standard Mixture with constant amount of 26 ERCC native targets from samples A, B, C and D. Each ERCC target is at a different concentration spanning a greater than $10^6$ dynamic range in abundance. FIG. 18B—bottom panel shows the linearity of cross titrating competitive Internal Standard Mixture with constant amount of endogenous cDNA native targets from samples A, B, C and D (same targets as assessed in gDNA; upper panel).

Touchdown PCR with Multiplex Competitive PCR

Increasing level of multiplex PCR requires a commensurate decrease in the concentration of primers used. Decreasing primer concentration has two predominant effects in multiplex PCR: 1) reduces formation of primer-dimer products, and 2) plateaus amplicon product formation early preventing dNTPs from becoming a limited reagent (less primer method). This latter effect is important as it enables all target templates to reach plateau phase, and in the presence of competitive IS drastically reduces oversampling/sequencing of high abundance targets without signal compression (FIGS. 19A-19C, FIGS. 20A-20B).

STARSEQ Reduces Oversampling without Signal Compression

FIG. 19A depicts two native targets (NT) within a hypothetical cDNA sample. One native target is in high abundance, $10^8$ copies ("Abundant" NT), while another is in low abundance, $10^2$ copies ("Rare" NT), representing a one-million fold difference in abundance between targets. This hypothetical cDNA sample is combined with a mixture of internal standards (IS) with a fixed relationship of concentrations at $10^5$ copies.

FIG. 19B depicts the multiplex competitive PCR library preparation for FIG. 19A. The PCR amplification plots for both the "Abundant" and "Rare" NT are separated for purposes of clarity, but occur in the same reaction. During multiplex competitive PCR, each native target competes equally with its respective competitive internal standard for dNTPs, polymerase and a limiting concentration of primers. Because the starting concentration of each target's primer-pair is the same, each competitive reaction will plateau around the same end-point concentration (~$10^9$ copies).

In FIG. 19C, the equal competition between each NT and respective IS preserves the proportional relationship between Native Targets in the original sample, allowing for measurement of native target abundance without signal compression. Yet, a $10^6$ fold range of templates is reduced to $10^3$ after multiplex competitive PCR library preparation resulting in a 1,000 fold reduction in oversampling of the high abundance target.

Mixing a sample of native targets in multiple ratios with IS mixture (FIG. 18A) results in a greater degree of uniformity in template concentration than what is obtainable with only one internal standard spike-in (FIG. 19A).

STARSEQ Reduces Required Sequencing Reads Up to 10,000-Fold

Figures 20A, 20B:
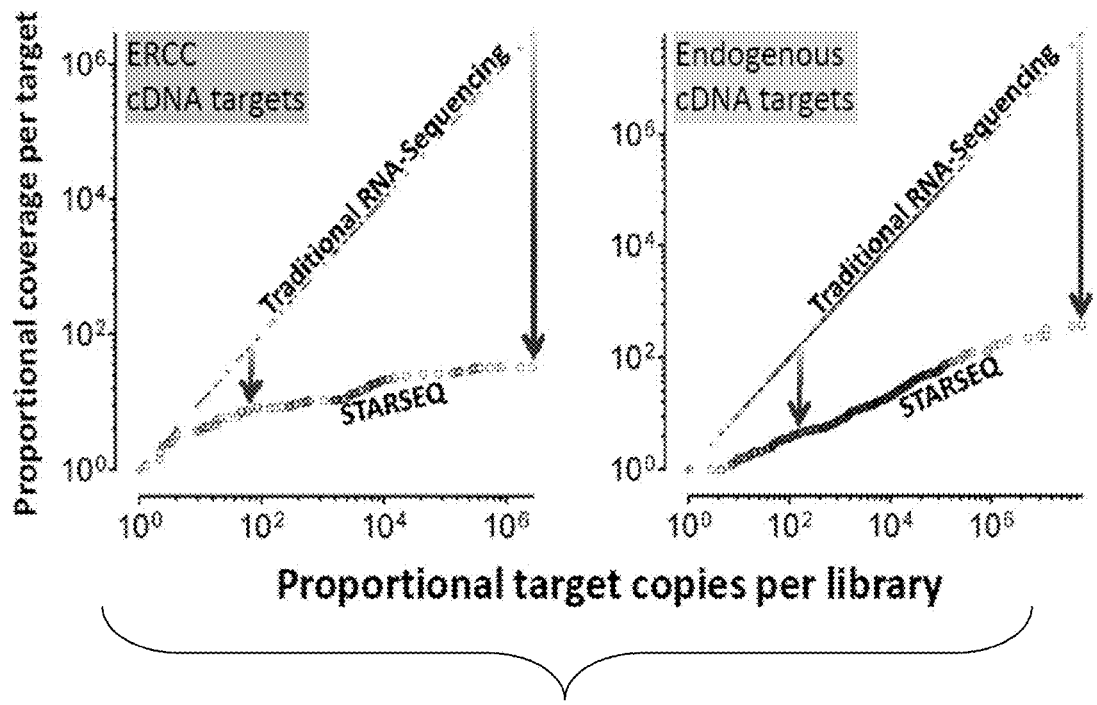
FIGS. 20A-20B: STARSEQ reduces required sequencing reads up to 10,000-fold.

FIG. 20A shows the actual proportional sequencing data for ERCC (n=104) and endogenous (n=400) cDNA targets. X-axis represents the proportional abundance of each target in a library preparation normalized to the lowest abundance target (set to $10^0$). Y-axis is in units of proportional sequencing reads (coverage) required to sequence the lowest abundance target at least once.

FIG. 20B is a tabular summary of FIG. 20A where the number of sequencing reads represents the sum of all sequencing reads to observe all targets at least once. Required number of traditional RNA-sequencing reads are calculated based on an assumed 1:1 relationship between target copies present in the library, and sequencing coverage required. Fold reduction in required sequencing reads by STARSEQ is the quotient of traditional RNA-sequencing and STARSEQ sequencing reads.

However, there is a limit to which one can dilute primers and still successfully amplify targets of interest. This limit can be pushed lower through several approaches: 1) increase primer melting temperature, and 2) increase the time during which annealing occurs to allow for eventual primer binding. Both of these solutions can exacerbate off-target priming. This apparent obstacle can is now shown herein to be able to be remedied by use of a modified touchdown PCR protocol. In this protocol, high annealing temperatures are incorporated during initial cycles of PCR to increase stringency of primer binding reducing off-target priming. In subsequent cycles annealing temperature is gradually lowered resulting in increased yield once sufficient specific product has formed during earlier high stringency cycles. Using this framework, the following protocol was developed: Each multiplex competitive reaction mixture was cycled in an air thermocycler (RapidCycler (Idaho Technology, Inc. Idaho Falls, Id.) under modified touchdown PCR conditions with low primer concentration: 95° C./3 min (Taq activation); 5 cycles of 94° C./30 s (denaturation), 72° C./4 min (annealing), and 72° C./15 sec (extension); repeat 5 cycles with annealing temperature decreased 1° C. to 71° C.; iterate 1° C. decrease and 5 cycles until annealing temperature is 64° C. (total of 45 cycles).

In particular embodiments, Hot Start Taq polymerase is used, as off-target priming and enzymatic activity is sufficiently high during reaction preparation that only primer-dimer product will otherwise be seen.

Performance of STARSEQ with ERCC Reference Materials

Figure 21A:
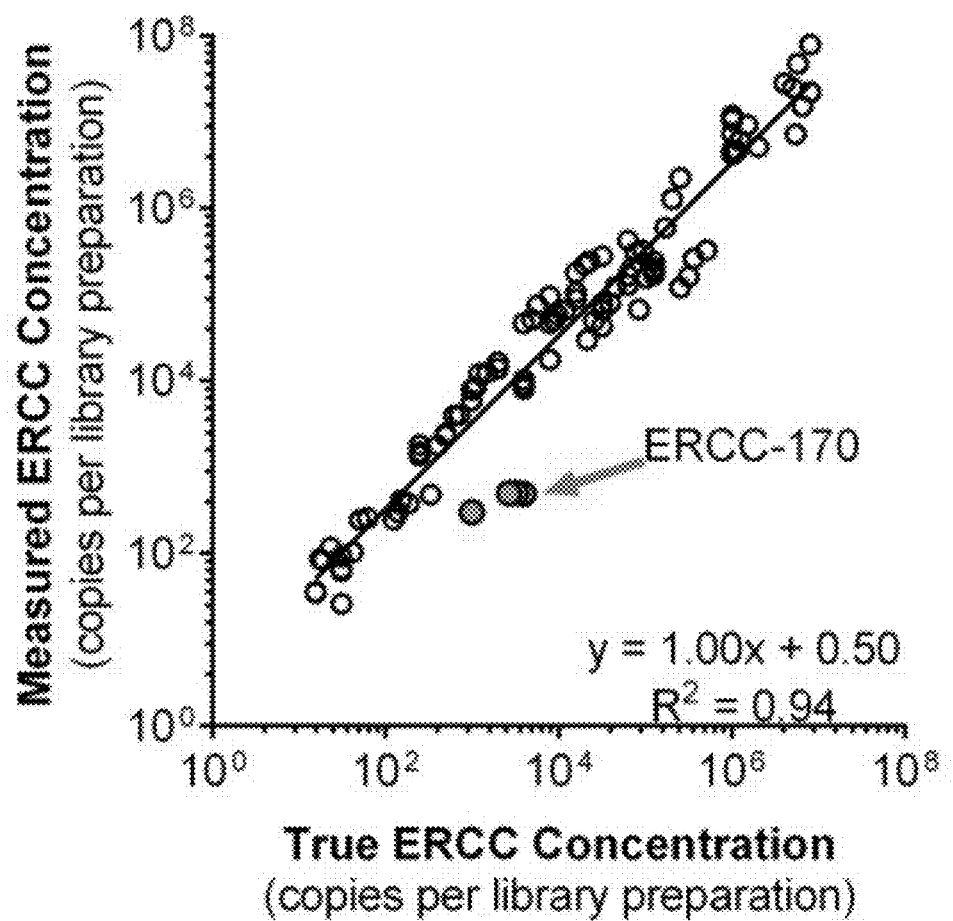
FIGS. 21A-21E: Performance of STARSEQ with ERCC Reference Materials.

FIG. 21A shows the measured signal abundance of ERCC targets in samples A, B, C and D. Points represent the median of ERCC measurements from those library preparations with at least 15 sequencing reads for both the NT and IS. X-axis units are derived from Ambion product literature for the known concentration of ERCC spike-in controls, SEQC project material preparation protocols, and an assumed 100% reverse transcription yield for each target.

Figure 21B:
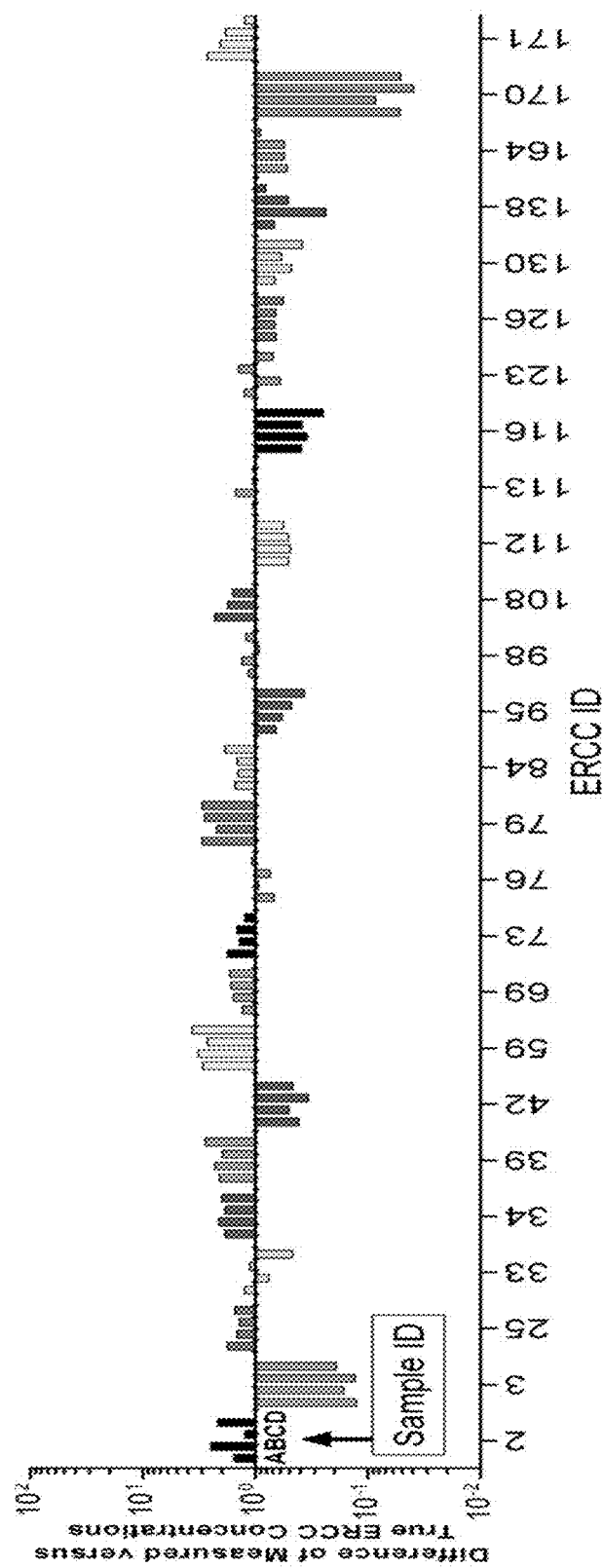

FIG. 21B shows difference plots of data in FIG. 21A ordered numerically by ERCC ID. Each ERCC target depicted was measured at least once in all four samples A-D. For purposes of clarity, ERCC-170 is highlighted orange in FIG. 21A and FIG. 21B.

Figure 21C:
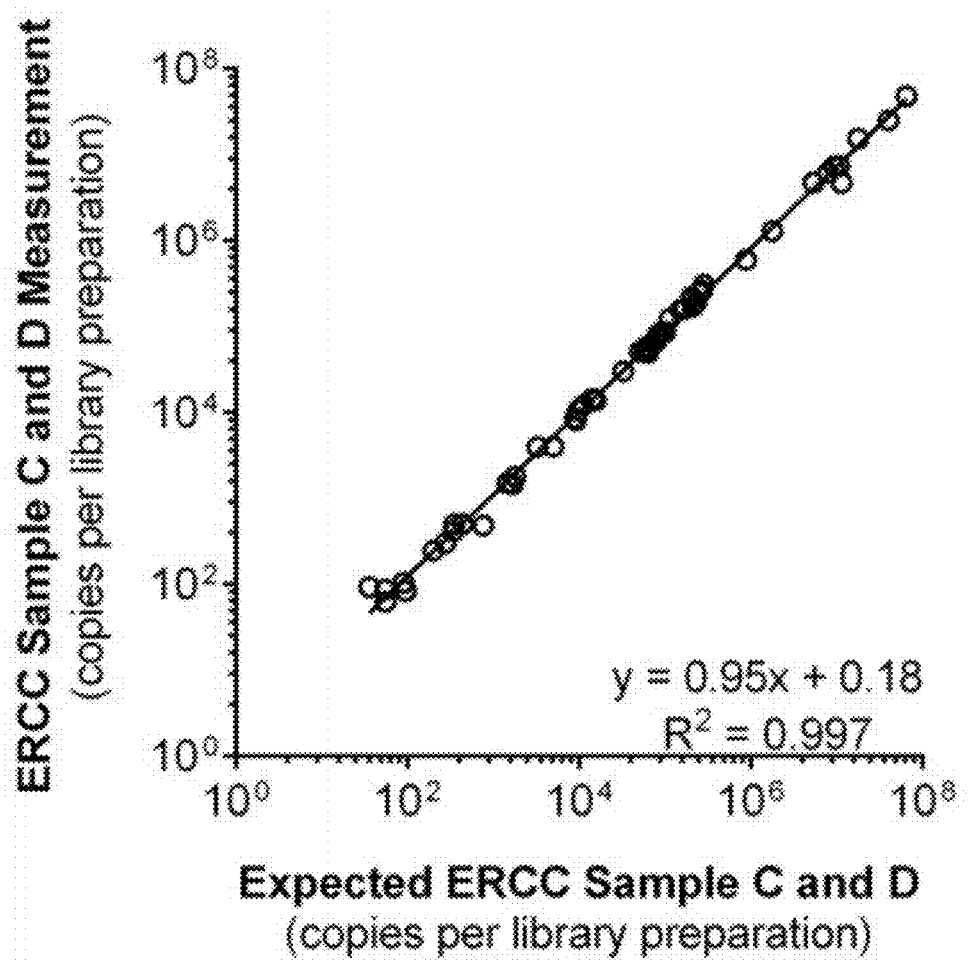

In FIG. 21C, samples C and D represent a 3:1 and 1:3 mixture, respectively, of Total RNA from samples A and B. These ratios were used to calculate expected measurements for samples C and D (x-axis) from measurements of A and B, and plotted against actual measurements of samples C and D (y-axis) (n=52).

Figure 21D:
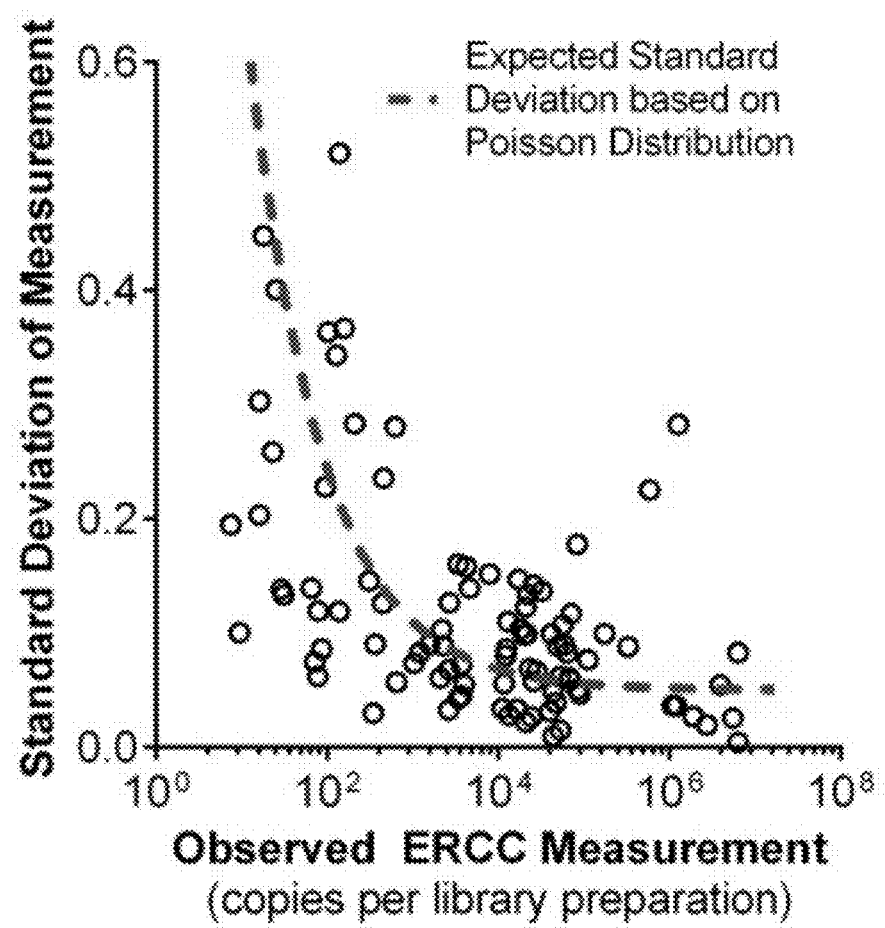

In FIG. 21D, points represent standard deviation in measurements of ERCC targets in SEQC A, B, C and D, for those assays with at least two IS dilution points that had at least 15 sequencing reads for both the NT and IS. The red line depicts the expected standard deviation based on a Poisson sampling distribution plus a baseline 0.08 technical replicate standard deviation.

Figure 21E:
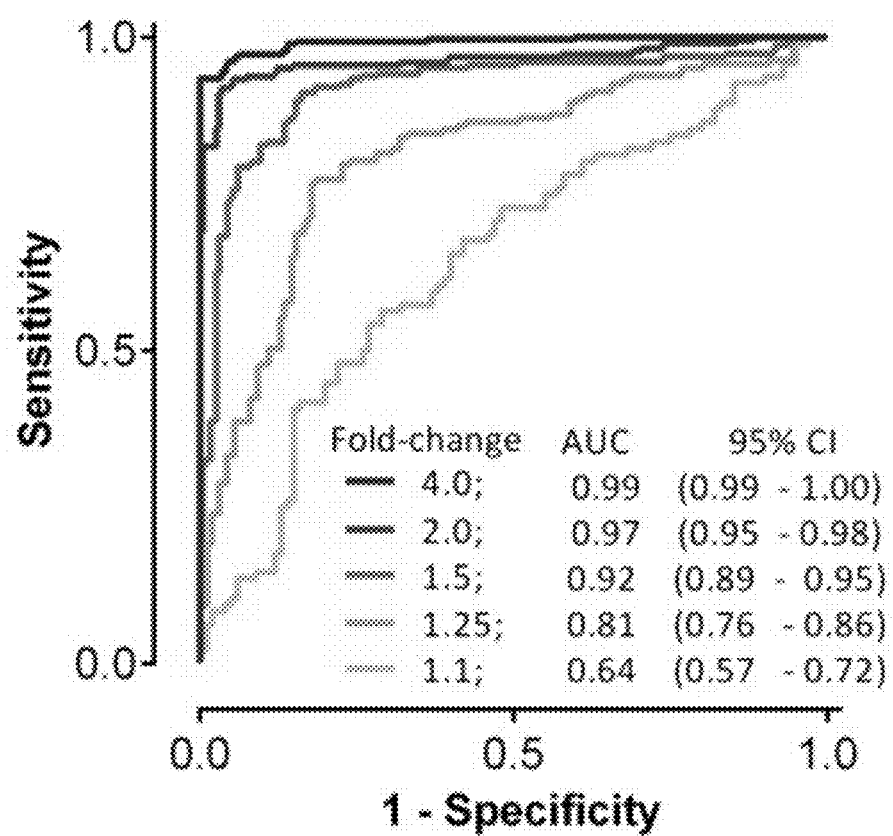

FIG. 21E shows ROC curves to detect fold change with corresponding area under the curve (AUC) with 95% confidence intervals. ROC curves are derived from the comparison of differential ratio subpools of ERCC targets in samples: A vs B, A vs C, A vs D, B vs C, B vs D and C vs D. Results for 1.1-fold change represent a range of differential ratio subpools [1.05-1.174] (controls n=100, tests n=96); 1.25 [1.175-1.374] (controls n=163, tests n=163); 1.5 [1.375-1.74] (controls n=229, tests n=227); 2.0 [1.75-2.49] (controls n=229, tests n=223); >4.0 [2.5-10.0] (controls n=286, tests n=290).

Performance of STARSEQ with Endogenous cDNA Targets

Figure 22A:
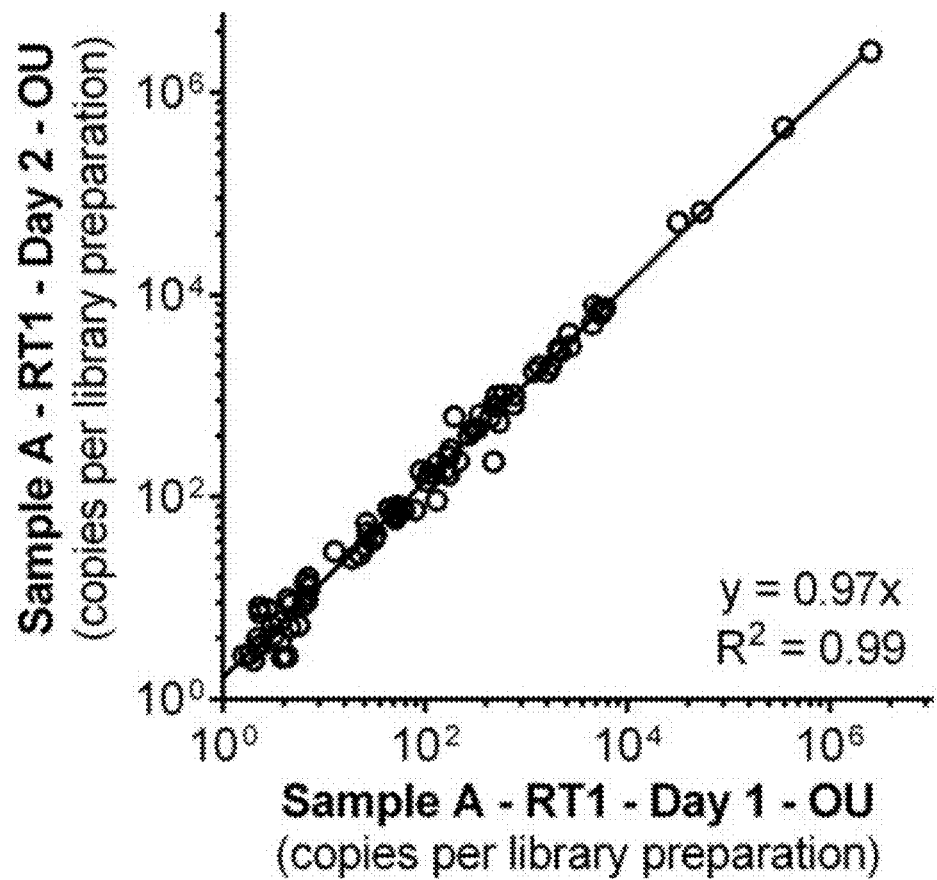
FIGS. 22A-22F: Performance of STARSEQ with endogenous cDNA targets.
Figure 22B:
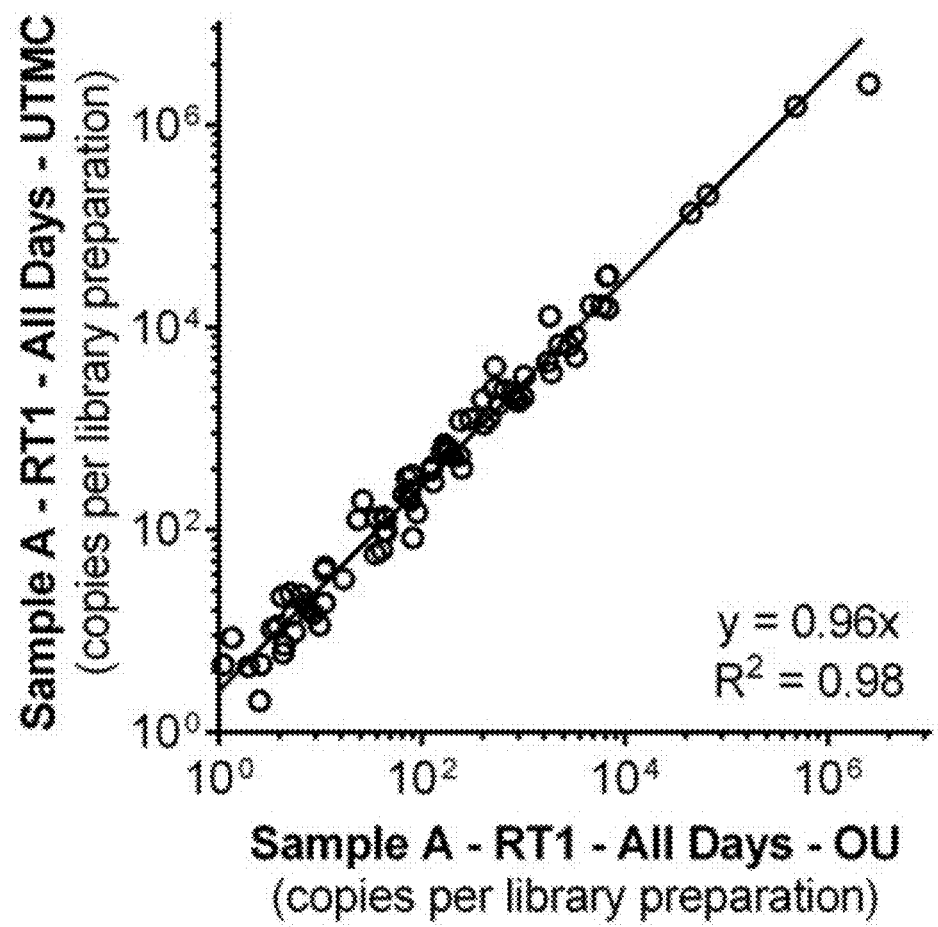
Figure 22C:
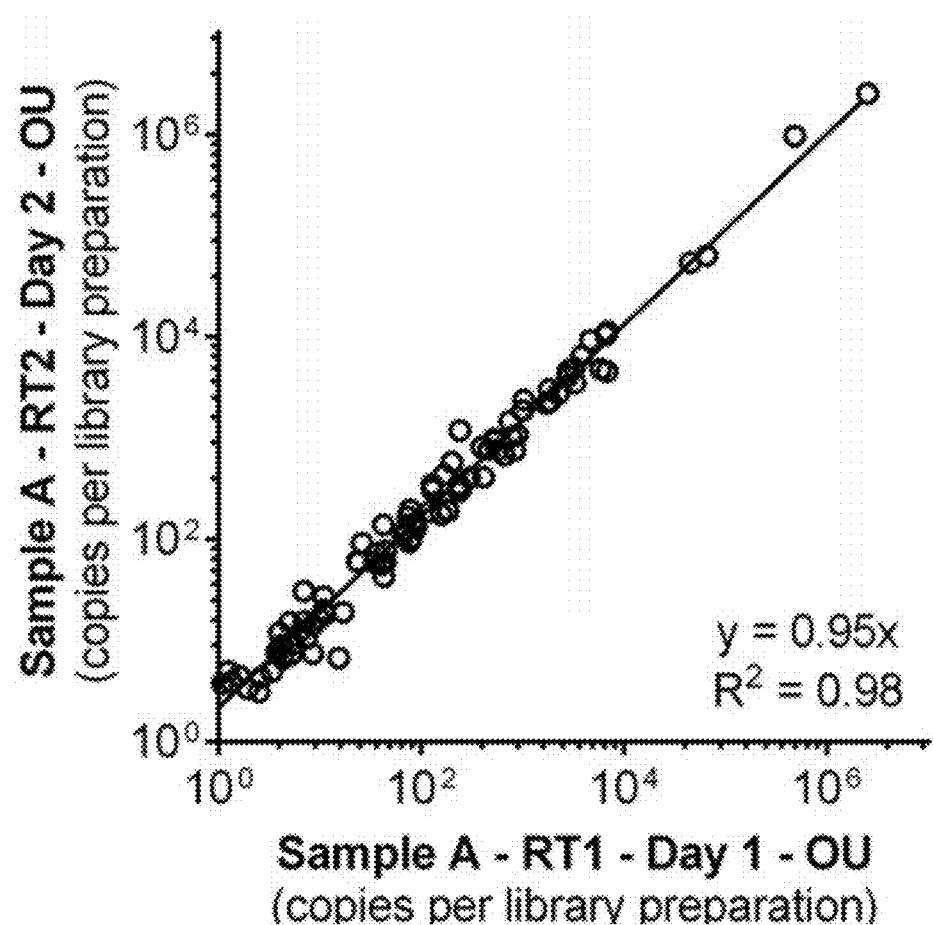
Figure 22D:
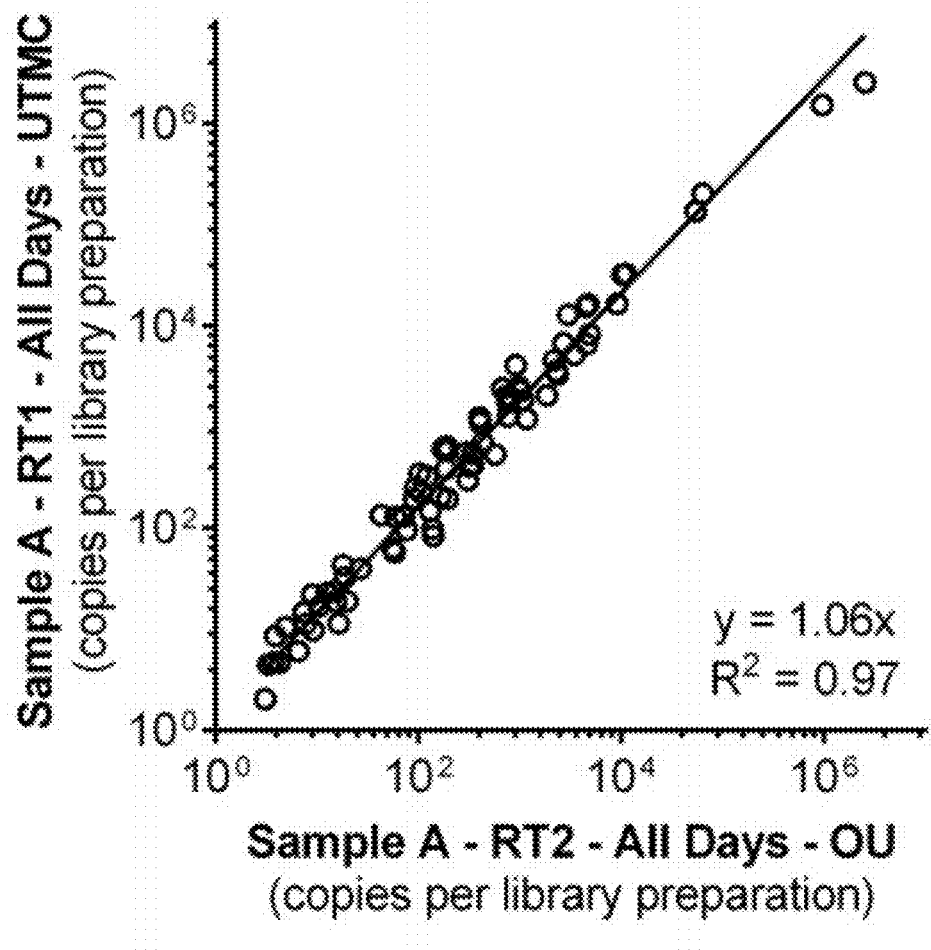
Figure 22E:
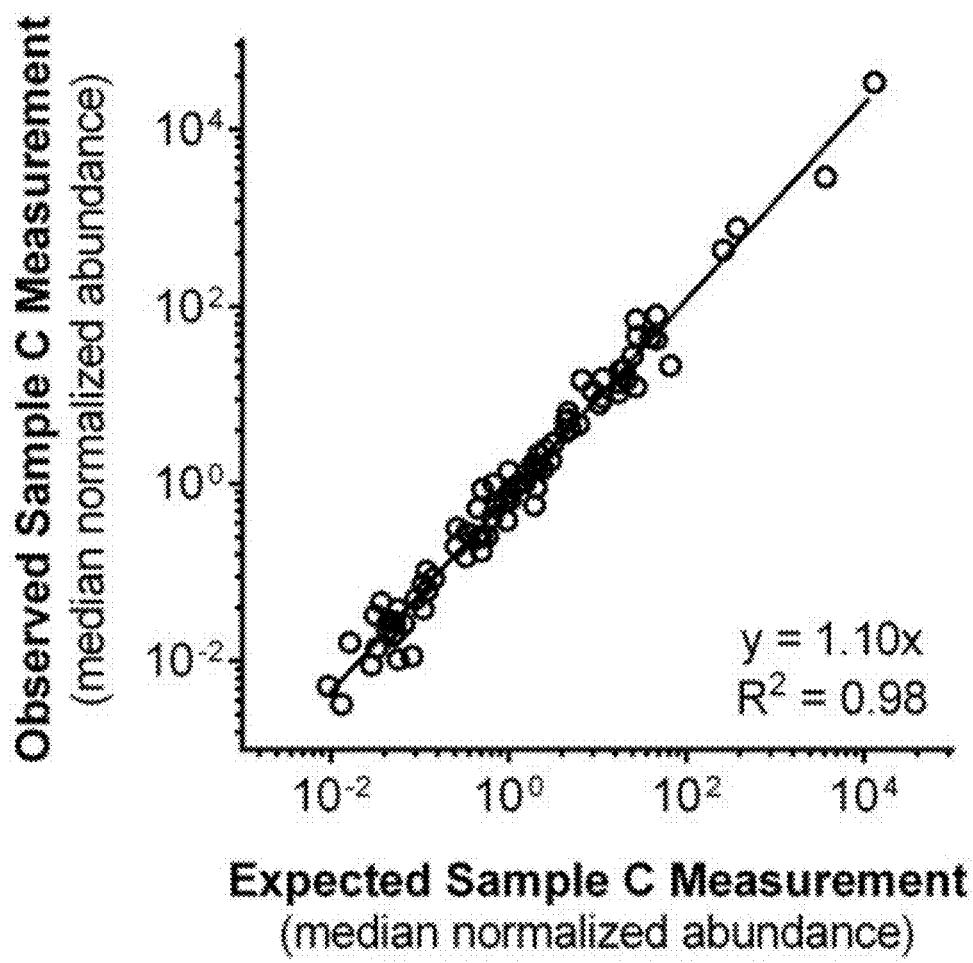
Figure 22F:
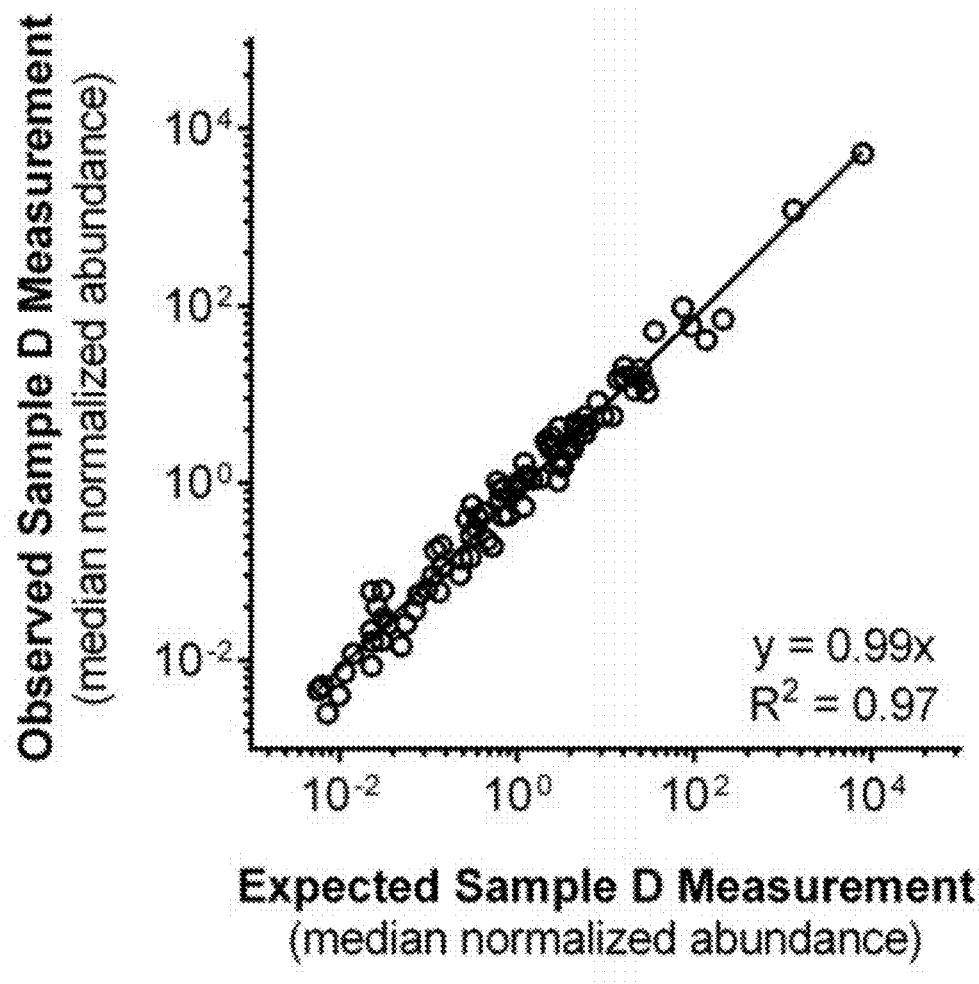
Figure 23A:
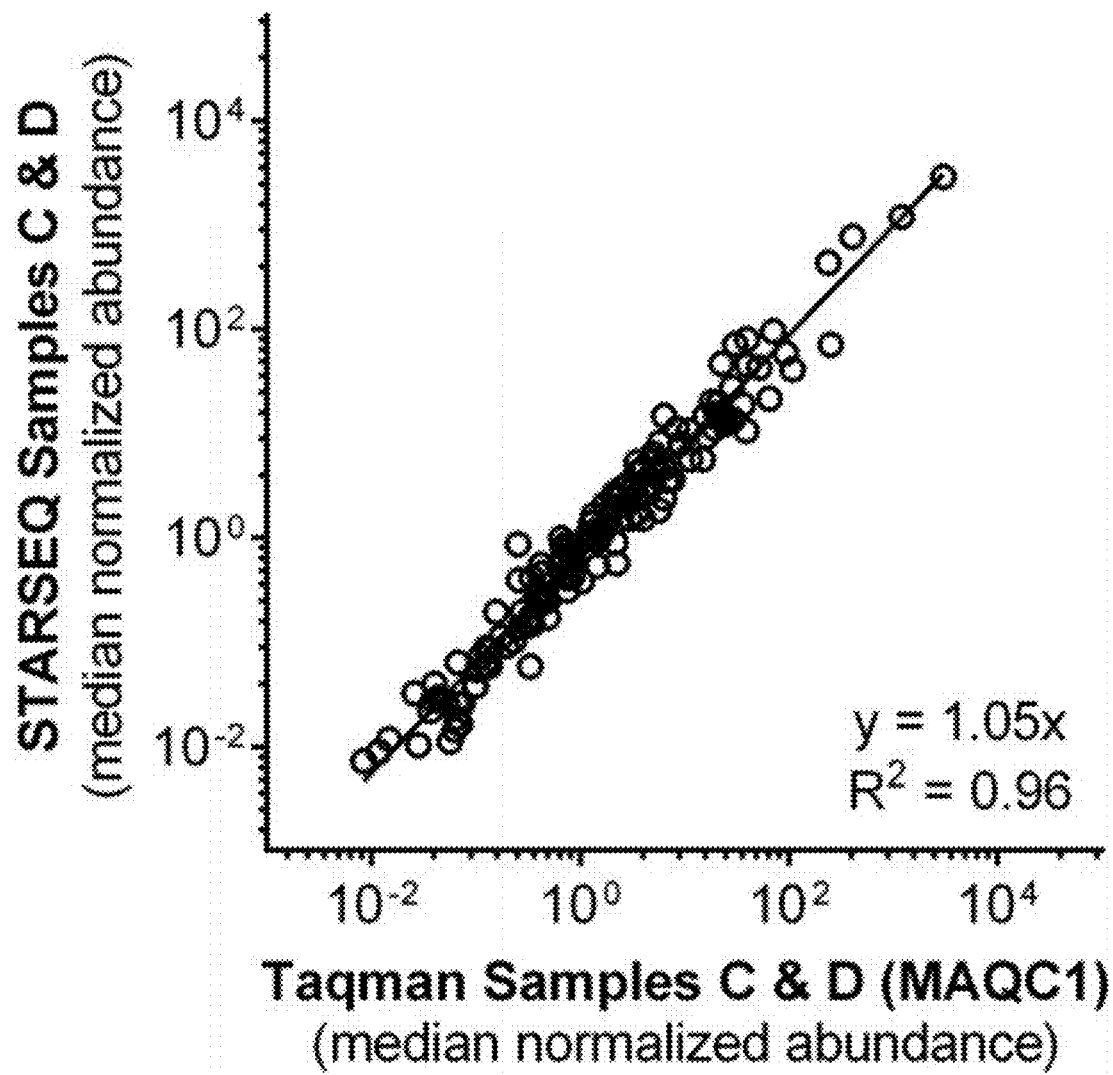
FIGS. 23A-23B: Cross-platform comparison of STARSEQ with TaqMan qPCR and Illumina RNA-Sequencing.
Figure 23B:
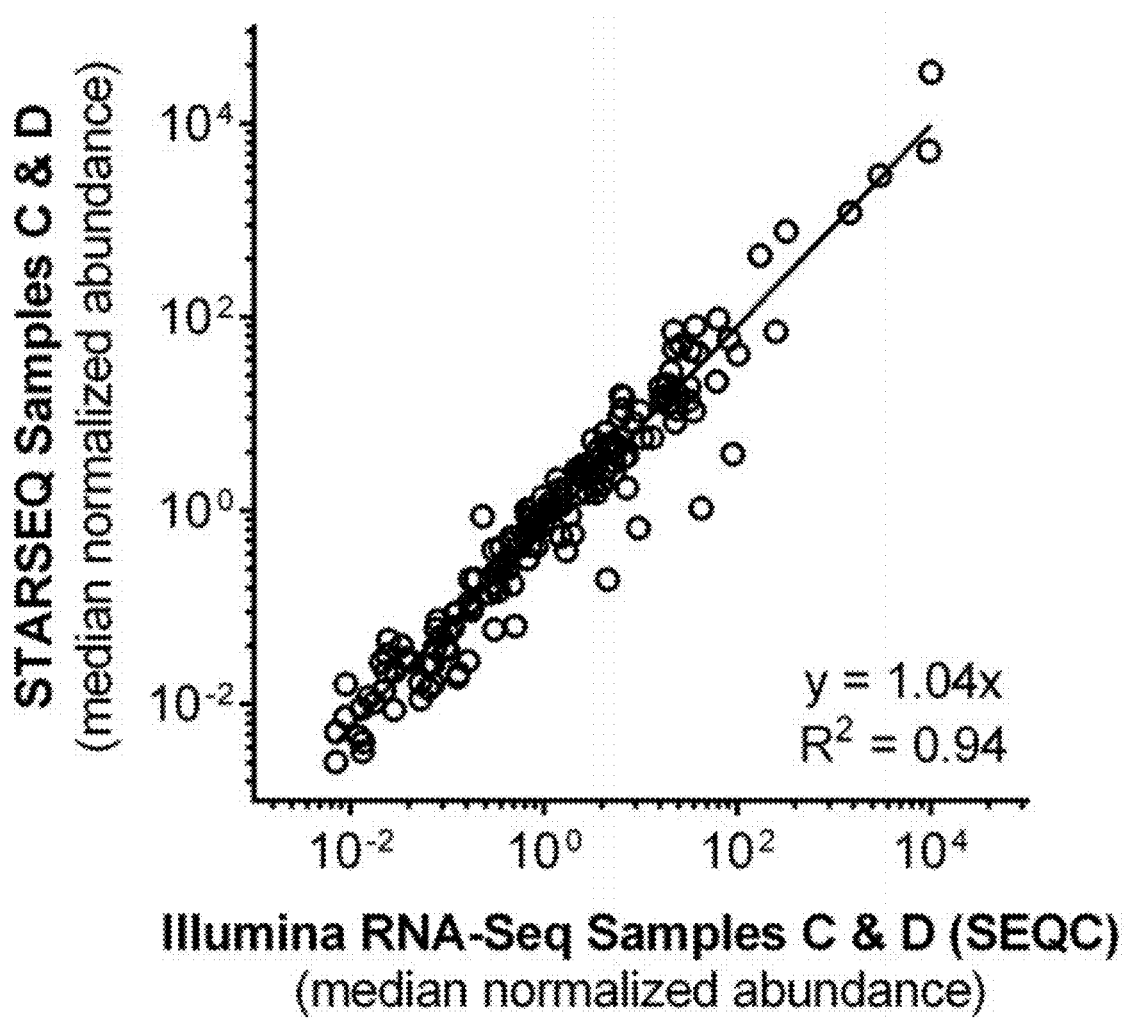

Absolute signal abundance of cDNA targets in sample A in units of copies per library preparation were measured on separate days, different sites (OU=Ohio University; UTMC=University of Toledo Medical Center), and between different reverse transcription preparations (RT1 and RT2). Points represent the median of ERCC measurements from those library preparations with at least 15 sequencing reads for both the NT and IS. FIG. 22A shows the inter-day effect (n=88). FIG. 22B shows the inter-day and Inter-site effect (n=81). FIG. 22C shows the inter-day and Inter-library effect (n=92). FIG. 22D shows the inter-day, Inter-site and Inter-library effect (n=80). FIGS. 22E-22F show that samples C and D represent a 3:1 and 1:3 mixture, respectively, of Total RNA from samples A and B. These ratios were used to calculate expected measurements for samples C and D (x-axis) from measurements of A and B, and plotted against actual measurements of samples C (n=86) and D (n=90) (y-axis).

Cross-Platform Comparison of STARSEQ with TaqMan qPCR and Illumina RNA-Sequencing.

Figure 24:
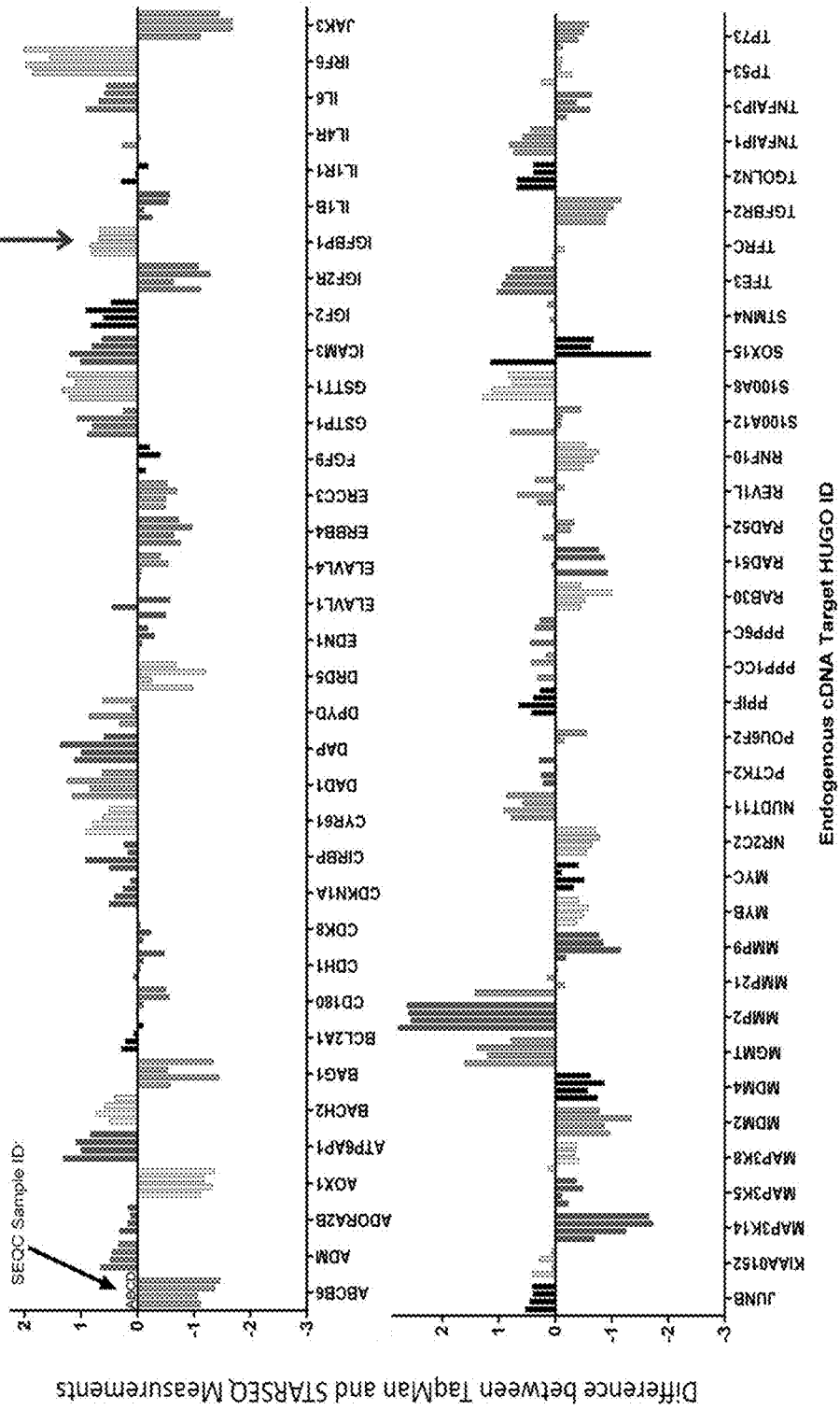
FIG. 24: Difference plots between TaqMan and STARSEQ measurements.
Figure 25:
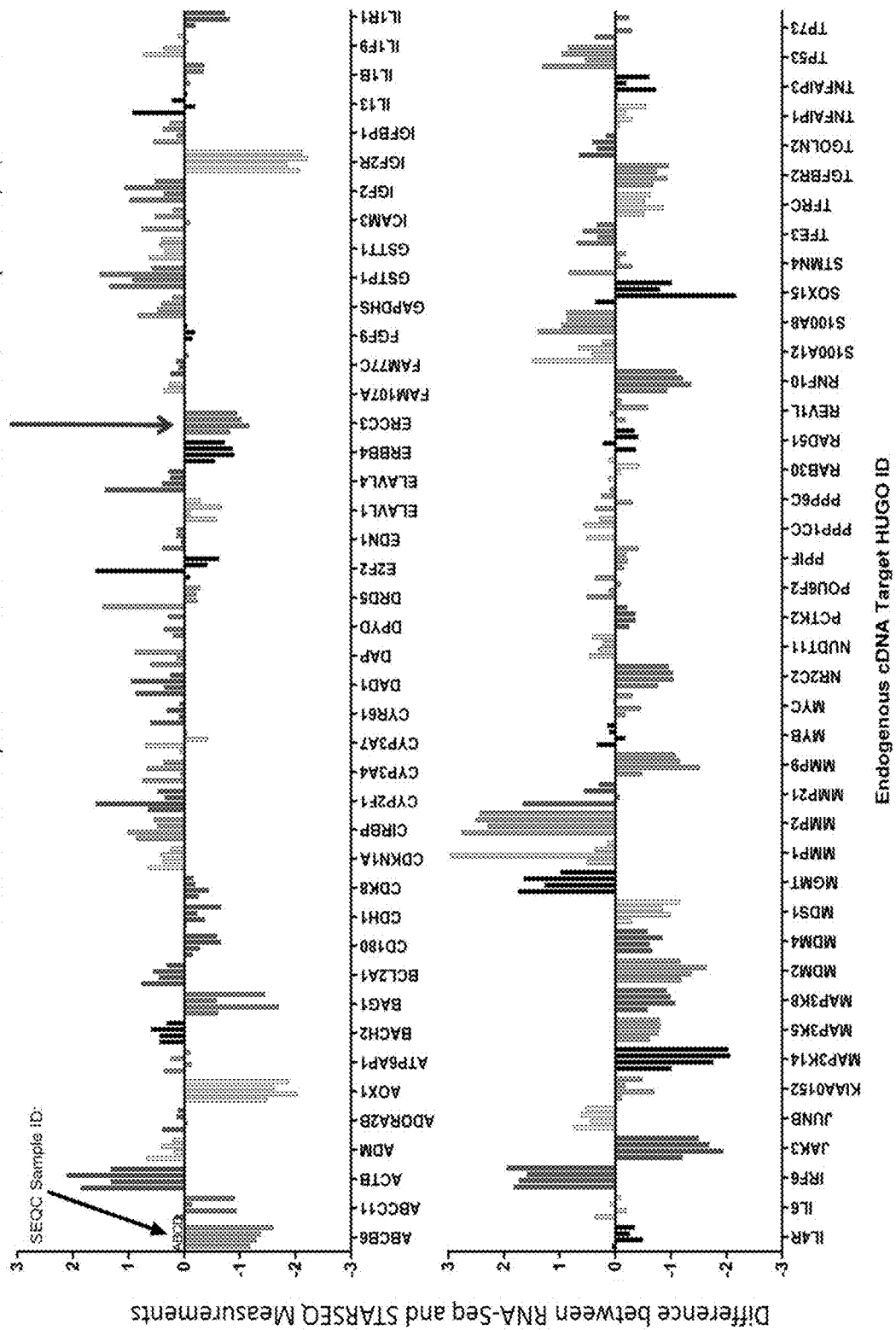
FIG. 25: Difference plots between Illumina RNA-Sequencing and STARSEQ measurements.

The average of differences for measurements of samples A and B between STARSEQ and TaqMan qPCR (FIG. 24 showing difference plots between TaqMan and STARSEQ measurements) or Illumina RNA-sequencing (FIG. 25 showing difference plots between Illumina RNA-Sequencing and STARSEQ measurements) was determined for each endogenous target. This difference was subtracted from TaqMan qPCR or Illumina RNA-sequencing measurements for samples C and D and plotted (x-axis) against STARSEQ measurements of C and D (y-axis).

STARSEQ measurements represent the median measurement from library preparations that had at least 15 sequencing reads for both the NT and IS. FIG. 26A shows a comparison of TaqMan qPCR with STARSEQ (n=292). FIG. 26B shows a comparison of Illumina RNA-Sequencing with STARSEQ (n=340).

Assay Performance

Assay measurement performance as assessed in SEQC samples A, B, C and D for ERCC as well as endogenous cDNA targets, as shown in FIG. 26. Endogenous targets were also assessed against gDNA control (see FIG. 18B).

True negative measurements occur when sufficient number of competitive internal standard was sequenced (sequenced at least 15 times), but insufficient native template was observed across all spike-in concentrations of internal standard. An upper limit of expression for these assays can still be calculated as [1/(IS sequencing counts)]×concentration IS loaded into the library preparation with the lowest IS concentration present. These measurements represent true negative measurements and the lower limit of accurate quantification can be determined from these data.

Failed assays are measurements where "sequencing depth was too low" for both the NT and IS. These represent true assay failures (neither native nor internal standard was sequenced at least 15 times). In this way, competitive IS mixtures can control for false negative reporting.

Addition of Barcodes and Sequencing Adaptors

A set of fusion primers were designed with their 3'-end complementary to the universal APEX-2 sequence tails added during multiplex competitive PCR. These fusion primers are tailed with a four nucleotide index/barcode sequence and 5' to that, a forward or reverse ion torrent amplicon sequencing adapter (FIG. 26). Both forward and reverse sequencing primers were intentionally barcoded to dual index each sample and reduce likelihood of false-indexing a sequence read; both barcodes must match. For each barcoding reaction, a 10 µL reaction volume was prepared containing: 1 µL of multiplex competitive PCR product, 1 µL of 1 µM forward and reverse barcoding primer, 1 µL of 2 mM dNTPs, 1 µL of 10× Idaho Technology reaction buffer with 30 mM MgCl$_2$, 0.1 µL of Promega GoTaq Hot Start Taq polymerase (5u/µL) and 4.9 µL of RNAse free water. Each barcoding reaction was cycled in an air thermocycler (RapidCycler (Idaho Technology, Inc. Idaho Falls, Id.) under the following conditions: 95° C./3 µM (Taq activation); 15 cycles of 94° C./5 s (denaturation), 58° C./10 sec (annealing), and 72° C./15 sec (extension). Reaction vessels are immediately removed and kept at 4° C. during all subsequent steps. The goal during this step is to prevent heterodimerization of barcoded product. Depending on the type of heterodimerization, post-sequencing alignment errors can arise from false sequencing base calls with resultant decrease in measurement precision and accuracy. Newly barcoded multiplex competitive PCR sequencing libraries are then individually quantified on an Agilent 2100 Bioanalyzer using DNA Chips with DNA 1000 Kit reagents according to manufacturer's protocol (Agilent Technologies Deutschland GmbH, Waldbronn, Germany). Uniquely barcoded sequencing libraries are then mixed in a known stoichiometric ratio so as to optimize the percentage of sequencing reads that each library will eventually receive; in most cases 1:1 is used.

STARSEQ "True Negative" Versus Taqman and RNA-Sequencing

26 STARSEQ measurements had sufficient data to report back a less than measurement. Of the 26 measurements, TaqMan reported not detected (ND) for 14, and RNA-Seq reported ND for 1 (see FIG. 27). Because STARSEQ could detect IS, but not accurately quantify NT present, these represent False Negative detections for TaqMan and RNA-Seq. Less than measurements were calculated as [1/(IS sequencing counts)]×concentration IS loaded into the library preparation.

Standard Deviation of ERCC Measurements.

FIG. 28 shows the SD of differences is calculated from data presented in FIG. 21. Intra-assay Intra-sample SD is calculated from the median of intra-assay SD within each sample A-D. Intra-assay Inter-sample SD is calculated from the median of intra-assay SD across samples A-D. Inter-assay Inter-sample SD is calculated from the median of inter-assay SD of residuals across samples A-D. Since the SD is reported in $Log_{10}$ values, it is roughly equivalent to reporting of the coefficient of variation (CV).

Product Purification and Sequencing

In certain embodiments, it is necessary during the purification of barcoded sequencing libraries that a system does not use strong denaturants or chaotropic salts, such as guanidine hydrochloride or thiocyanate. These agents result in downstream template heterodimerization, false sequencing base calls and post-sequencing alignment errors. For this reason, each mixture of barcoded sequencing libraries were purified using Life Technologies E-Gel SizeSelect 2% Agarose gels, which does not report the use of denaturants or chaotropic salts, and can be run in a refrigerated room to prevent heat denaturation during electrophoretic separation. Purified sequencing libraries were then quantified using the KAPA Library Quantification Kit for Ion Torrent Sequencing Platforms (Kapa Biosystems). Based on this quantification, libraries were diluted appropriately and prepared for Ion Torrent PGM Sequencing service according to manufacturer's recommendations at the University of Toledo Medical Center (UTMC), Toledo, Ohio and Ohio University (OU), Athens, Ohio.

FASTQ File Processing

Raw sequencing data from an NGS service were provided back in FASTQ format. Sequencing reads were extracted and each sequencing read was parsed into 3 separate FASTQ files: 1) forward (query-barcodefastq) and 2) reverse barcode (query-revbarcodefastq) regions, as well as 3) central portion of the amplicon (query-subjectfastq) corresponding to the region internal to target specific priming sites where six nucleotide substitutions should exist between NT and matching competitive IS.

BFAST of Sequences Against Subject Database

Each of the three FASTQ files were aligned with known reference FASTA databases corresponding to whether it was a barcode (barcode.fa) or amplicon region (subject.fa) using the BLAT-like fast, accurate search tool (BFAST, version 0.7.0a), with file output in sequence alignment/map (SAM) format. BFAST match against the index databases and SAM file output was performed for the trimmed FASTQ files containing 1) forward barcode, 2) reverse barcode and 3) captured amplicon subject sequences.

Binning of Sequence Counts

Each of the three SAM files from 1) forward and 2) reverse barcode, and 3) amplicon region were then merged into a practical extraction and reporting language (PERL) hash table using the sequence read ID as a key for matching (http://www.perl.org/). Based on barcode and amplicon alignment, each sequencing read was binned into an array corresponding to the IS input concentration for a given sample preparation, and whether it was called as an NT or IS by BFAST alignment. If the forward and reverse barcode alignment calls did not match, the sequence read was not binned. The resulting hash table of binned sequencing reads is output in comma delimited format and processed as outlined in the Statistical Methods section.

Measuring Relative Abundance

At least 14 sequencing reads were required for each of the NT and IS. Correct fold-dilution was determined based on change in NT:IS ratio across multiple assay targets and across multiple serially diluted internal standard spike-ins. The dilution of internal standard was then multiplied by NT:IS ratio. Each assay had multiple measurements per assay because of multiple dilutions of internal standard. If the STDEV of these measurements is less than 10-fold in variance, the median of these measurements was accepted. Correct measurements were based on predetermined assay systematic bias of internal standard concentrations. The population of these measurements was normalized to a population median.

STARSEQ Measurement Inclusion/Exclusion Criteria

Each native target (gDNA or cDNA) was measured relative to its respective internal standard within a cross-titrated concentration of the ISM (FIG. 18). An empirical threshold of at least 15 sequencing reads each for native target (NT) and respective competitive internal standard (IS) was the optimal inclusion/exclusion criterion to consider a NT:IS ratio valid (power>80%; type 1 error rate<0.05; to detect 2-fold NT:IS ratio change) (FIG. 18). For those assays with more than one measurement that met criteria above, a coefficient of variation (CV) of >1000% between measurements triggered exclusion for that assay measurement in that particular sample.

Statistical Methods: Estimate of Native Target Concentration

For each gene target and technical replicate with input concentration of each IS mixture indexed with the subscript i, an estimate of the concentration of the native target ($NC_i$) was calculated based on the observed/binned sequence counts of both the native target ($NT_i$) and internal standard ($IS_i$), as well as the known starting concentration (in units of template copies per library preparation) of the internal standard ($SC_i$):

$$\log_{10} NC_i = \log_{10}\frac{NT_i}{IS_i} + \log_{10} SC_i$$

The empirically determined optimal method and QC parameter for estimating the summarization quantity was, 1) the median ($NC_{median}$) of $NC_i$ technical replicate measures that have, 2) at least 15 sequencing counts for both $NT_i$ as well as $IS_i$, and 3) coefficient of variation (CV) across $NC_i$ of less than 1.00 on a base 10 logarithm scale. This was selected so as to have sufficient sampling of a given target to enable the detection of a 2-fold change in abundance between targets with a type 1 error rate of less than 0.05, and a type 2 error rate less than 0.20.

Example 4

Non-Limiting Examples of Applications

In some embodiments, a method for obtaining a numerical index that indicates a biological state comprises providing 2 samples corresponding to each of a first biological state and a second biological state; measuring and/or enumerating an amount of each of 2 nucleic acids in each of the 2 samples; providing the amounts as numerical values that are directly comparable between a number of samples; mathematically computing the numerical values corresponding to each of the first and second biological states; and determining a mathematical computation that discriminates the two biological states. First and second biological states as used herein correspond to two biological states of to be compared, such as two phenotypic states to be distinguished. Non-limiting examples include, e.g., non-disease (normal) tissue vs. disease tissue; a culture showing a therapeutic drug response vs. a culture showing less of the therapeutic drug response; a subject showing an adverse drug response vs. a subject showing a less adverse response; a treated group of subjects vs. a non-treated group of subjects, etc.

A "biological state" as used herein can refer to a phenotypic state, for e.g., a clinically relevant phenotype or other metabolic condition of interest. Biological states can include, e.g., a disease phenotype, a predisposition to a disease state or a non-disease state; a therapeutic drug response or predisposition to such a response, an adverse drug response (e.g. drug toxicity) or a predisposition to such a response, a resistance to a drug, or a predisposition to showing such a resistance, etc. In preferred embodiments, the numerical index obtained can act as a biomarker, e.g., by correlating with a phenotype of interest. In some embodiments, the drug may be and anti-tumor drug. In certain embodiments, the use of the method described herein can provide personalized medicine.

In certain embodiments, the biological state corresponds to a normal expression level of a gene. Where the biological state does not correspond to normal levels, for example falling outside of a desired range, a non-normal, e.g., disease condition may be indicated.

A numerical index that discriminates a particular biological state, e.g., a disease or metabolic condition, can be used as a biomarker for the given condition and/or conditions related thereto. For example, in some embodiments, the biological state indicated can be at least one of an angiogenesis-related condition, an antioxidant-related condition, an apoptosis-related condition, a cardiovascular-related condition, a cell cycle-related condition, a cell structure-related condition, a cytokine-related condition, a defense response-related condition, a development-related condition, a diabetes-related condition, a differentiation-related condition, a DNA replication and/or repair-related condition, an endothelial cell-related condition, a hormone receptor-related condition, a folate receptor-related condition, an inflammation-related condition, an intermediary metabolism-related condition, a membrane transport-related condition, a neurotransmission-related condition, a cancer-related condition, an oxidative metabolism-related condition, a protein maturation-related condition, a signal transduction-related condition, a stress response-related condition, a tissue structure-related condition, a transcription factor-related condition, a transport-related condition, and a xenobiotic metabolism-related condition. In other specific embodiments, antioxidant and xenobiotic metabolism enzyme genes can be evaluated in human cells; micro-vascular endothelial cell gene expression; membrane transport genes expression; immune resistance; transcription control of hormone receptor expression; and gene expression patterns with drug resistance in carcinomas and tumors.

In some embodiments, one or more of the nucleic acids to be measured are associated with one of the biological states to a greater degree than the other(s). For example, in some embodiments, one or more of the nucleic acids to be evaluated is associated with a first biological state and not with a second biological state.

A nucleic acid may be said to be "associated with" a particular biological state where the nucleic acid is either positively or negatively associated with the biological state. For example, a nucleic acid may be said to be "positively associated" with a first biological state where the nucleic acid occurs in higher amounts in a first biological state compared to a second biological state. As an illustration, genes highly expressed in cancer cells compared to non-cancer cells can be said to be positively associated with cancer. On the other hand, a nucleic acid present in lower amounts in a first biological state compared to a second biological state can be said to be negatively associated with the first biological state.

The nucleic acid to be measured and/or enumerated may correspond to a gene associated with a particular phenotype. The sequence of the nucleic acid may correspond to the transcribed, expressed, and/or regulatory regions of the gene (e.g., a regulatory region of a transcription factor, e.g., a transcription factor for co-regulation).

In some embodiments, expressed amounts of more than 2 genes are measured and used in to provide a numerical index indicative of a biological state. For example, in some cases, expression patterns of multiple genes are used to characterize a given phenotypic state, e.g., a clinically relevant phenotype. In some embodiments, expressed amounts of at least about 5 genes, at least about 10 genes, at least about 20 genes, at least about 50 genes, or at least about 70 genes may be measured and used to provide a numerical index indicative of a biological state. In some embodiments of the instant invention, expressed amounts of less than about 90 genes, less than about 100 genes, less than about 120 genes, less than about 150 genes, or less than about 200 genes may be measured and used to provide a numerical index indicative of a biological state.

Determining which mathematic computation to use to provide a numerical index indicative of a biological state may be achieved by any methods known in the arts, e.g., in the mathematical, statistical, and/or computational arts. In some embodiments, determining the mathematical computation involves a use of software. For example, in some embodiments, a machine learning software can be used.

Mathematically computing numerical values can refer to using any equation, operation, formula and/or rule for interacting numerical values, e.g., a sum, difference, product, quotient, log power and/or other mathematical computation. In some embodiments, a numerical index is calculated by dividing a numerator by a denominator, where the numerator corresponds to an amount of one nucleic acid and the denominator corresponds to an amount the another nucleic acid. In certain embodiments, the numerator corresponds to a gene positively associated with a given biological state and the denominator corresponds to a gene negatively associated with the biological state. In some embodiments, more than one gene positively associated with the biological state being evaluated and more than one gene negatively associated with the biological state being evaluated can be used. For example, in some embodiments, a numerical index can be derived comprising numerical values for the positively associated genes in the numerator and numerical values for an equivalent number of the negatively associated genes in the denominator. In such balanced numerical indices, the reference nucleic acid numerical values cancel out. In some embodiments, balanced numerical values can neutralize effects of variation in the expression of the gene(s) providing the reference nucleic acid(s). In some embodiments, a numerical index is calculated by a series of one or more mathematical functions.

In some embodiments, more than 2 biological states can be compared, e.g., distinguished. For example, in some embodiments, samples may be provided from a range of biological states, e.g., corresponding to different stages of disease progression, e.g., different stages of cancer. Cells in different stages of cancer, for example, include a non-cancerous cell vs. a non-metastasizing cancerous cell vs. a metastasizing cell from a given patient at various times over the disease course. Cancer cells of various types of cancer may be used, including, for example, a bladder cancer, a bone cancer, a brain tumor, a breast cancer, a colon cancer, an endocrine system cancer, a gastrointestinal cancer, a gynecological cancer, a head and neck cancer, a leukemia, a lung cancer, a lymphoma, a metastases, a myeloma, neoplastic tissue, a pediatric cancer, a penile cancer, a prostate cancer, a sarcoma, a skin cancer, a testicular cancer, a thyroid cancer, and a urinary tract cancer. In preferred embodiments, biomarkers can be developed to predict which chemotherapeutic agent can work best for a given type of cancer, e.g., in a particular patient.

A non-cancerous cell may include a cell of hematoma and/or scar tissue, as well as morphologically normal parenchyma from non-cancer patients, e.g., non-cancer patients related or not related to a cancer patient. Non-cancerous cells may also include morphologically normal parenchyma from cancer patients, e.g., from a site close to the site of the cancer in the same tissue and/or same organ; from a site further away from the site of the cancer, e.g., in a different tissue and/or organ in the same organ-system, or from a site still further away e.g., in a different organ and/or a different organ-system.

Numerical indices obtained can be provided as a database. Numerical indices and/or databases thereof can find use in diagnoses, e.g. in the development and application of clinical tests.

Diagnostic Applications

In some embodiments, a method of identifying a biological state is provided. In some embodiments, the method comprises measuring and/or enumerating an amount of each of 2 nucleic acids in a sample, providing the amounts as numerical values; and using the numerical values to provide a numerical index, whereby the numerical index indicates the biological state.

A numerical index that indicates a biological state can be determined as described above in accordance with various embodiments. The sample may be obtained from a specimen, e.g., a specimen collected from a subject to be treated. The subject may be in a clinical setting, including, e.g., a hospital, office of a health care provider, clinic, and/or other health care and/or research facility. Amounts of nucleic acid(s) of interests in the sample can then be measured and/or enumerated.

In certain embodiments, where a given number of genes are to be evaluated, expression data for that given number of genes can be obtained simultaneously. By comparing the expression pattern of certain genes to those in a database, a chemotherapeutic agent that a tumor with that gene expression pattern would most likely respond to can be determined.

In some embodiments, the methods can be used to quantify exogenous normal gene in the presence of mutated endogenous gene. Using primers that span the deleted region, one can selectively amplify and quantitate expression from a transfected normal gene and/or a constitutive abnormal gene.

In some embodiments, methods described herein can be used to determine normal expression levels, e.g., providing numerical values corresponding to normal gene transcript expression levels. Such embodiments may be used to indicate a normal biological state, at least with respect to expression of the evaluated gene.

Normal expression levels can refer to the expression level of a transcript under conditions not normally associated with a disease, trauma, and/or other cellular insult. In some embodiments, normal expression levels may be provided as a number, or preferably as a range of numerical values corresponding to a range of normal expression of a particular gene, e.g., within +/−a percentage for experimental error. Comparison of a numerical value obtained for a given nucleic acid in a sample, e.g., a nucleic acid corresponding to a particular gene, can be compared to established-normal numerical values, e.g., by comparison to data in a database provided herein. As numerical values can indicate numbers of molecules of the nucleic acid in the sample, this comparison can indicate whether the gene is being expressed within normal levels or not.

In some embodiments, the method can be used for identifying a biological state comprising assessing an amount a nucleic acid in a first sample, and providing said amount as a numerical value wherein said numerical value is directly comparable between a number of other samples. In some embodiments, the numerical value is potentially directly comparable to an unlimited number of other samples. Samples may be evaluated at different times, e.g., on different days; in the same or different experiments in the same laboratory; and/or in different experiments in different laboratories.

Therapeutics

Some embodiments provide a method of improving drug development. For example, use of a standardized mixture of internal standards, a database of numerical values and/or a database of numerical indices may be used to improve drug development.

In some embodiments, modulation of gene expression is measured and/or enumerated at one or more of these stages, e.g., to determine effect a candidate drug. For example, a candidate drug (e.g., identified at a given stage) can be administered to a biological entity. The biological entity can be any entity capable of harboring a nucleic acid, as described above, and can be selected appropriately based on the stage of drug development. For example, at the lead identification stage, the biological entity may be an in vitro culture. At the stage of a clinical trial, the biological entity can be a human patient.

The effect of the candidate drug on gene expression may then be evaluated, e.g., using various embodiments of the instant invention. For example, a nucleic acid sample may be collected from the biological entity and amounts of nucleic acids of interest can be measured and/or enumerated. For example, amounts can be provided as numerical value and/or numerical indices. An amount then may be compared to another amount of that nucleic acid at a different stage of drug development; and/or to a numerical values and/or indices in a database. This comparison can provide information for altering the drug development process in one or more ways.

Altering a step of drug development may refer to making one or more changes in the process of developing a drug, preferably so as to reduce the time and/or expense for drug development. For example, altering may comprise stratifying a clinical trial. Stratification of a clinical trial can refer to, e.g., segmenting a patient population within a clinical trial and/or determining whether or not a particular individual may enter into the clinical trial and/or continue to a subsequent phase of the clinical trial. For example, patients may be segmented based on one or more features of their genetic makeup determined using various embodiments of the instant invention. For example, consider a numerical value obtained at a pre-clinical stage, e.g., from an in vitro culture that is found to correspond to a lack of a response to a candidate drug. At the clinical trial stage, subjects showing the same or similar numerical value can be exempted from participation in the trial. The drug development process has accordingly be altered, saving time, and costs.

Kits

The internal amplification control (IAC)/competitive internal standards (IS) described herein may be assembled and provided in the form of kits. In some embodiments, the kit provides the IAC and reagents necessary to perform a PCR, including Multiplex-PCR and next-generation sequencing (NGS). The IAC may be provided in a single, concentrated form where the concentration is known, or serially diluted in solution to at least one of several known working concentrations.

The kits may include IS of 150 identified endogenous targets, as described herein, or IS of 28 ERCC targets, as described herein, or both. These IS may be provided in solution allowing the IS to remain stable for up to several years.

The kits may also provide primers designed specifically to amplify the IS of 150 endogenous targets, the IS of 28 ERCC targets, and their corresponding native targets. The kits may also provide one or more containers filled with one or more necessary PCR reagents, including but not limited to dNTPs, reaction buffer, Taq polymerase, and RNAse-free water. Optionally associated with such container(s) is a notice in the form prescribed by a governmental agency regulating the manufacture, use or sale of IAC and associated reagents, which notice reflects approval by the agency of manufacture, use or sale for research use.

The kits may include appropriate instructions for preparing, executing, and analyzing PCR, including Multiplex-PCR and NGS, using the IS included in the kit. The instructions may be in any suitable format, including, but not limited to, printed matter, videotape, computer readable disk, or optical disc.

All publications, including patents and non-patent literature, referred to in this specification are expressly incorporated by reference herein. Citation of the any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

What is claimed is:

1. A method of controlling for non-systematic errors by reducing oversampling of overrepresented native nucleic acid targets and stochastic sampling error associated with deep sequencing, the method comprising:
   i) preparing a mixture comprising a known number of internal amplification control (IAC) nucleic acid molecules corresponding to each native nucleic acid target; and
   ii) mixing the IAC mixture of step i) with a native nucleic acid target-containing sample;
   wherein each native nucleic acid target is similar to its respective IAC, with the exception of one or more changes to the nucleic acid sequence that are identifiable with sequencing, and wherein such changes can include one or more of deletions, additions, or alteration to the ordering or composition of nucleotides used;
   iii) sequencing the mixture of step ii);
   iv) assessing the ratio of sequencing events between the native nucleic acid target and its respective IAC, along with the known number of IAC nucleic acid molecules input into the sample; and
   v) quantifiably determining the original amount of each native nucleic acid target in the original sample.

2. The method of claim 1, wherein the known number in step i) comprises one or more of: concentration and amount.

3. The method of claim 1, further comprising:
   conducting multiplexed analyses of multiple native nucleic acid targets across multiple samples, experiments and/or platforms.

4. The method of claim 1, wherein the assessing step iv) comprises determining an amount of a first native nucleic acid target in a first sample, by:
   a) providing a standardized mixture of the known number of IAC nucleic acid molecules wherein the IAC nucleic acid molecules include a first competitive template for a first native nucleic acid and a second competitive template for a second native nucleic acid in said first sample, wherein said first and second competitive templates are at known concentrations relative to each other;
   b) combining said first sample with said standardized mixture;
   c) co-amplifying said first native nucleic acid and said first competitive template for said first native nucleic acid to produce a first amplified product thereof;
   d) diluting said first amplified product of step c);
   e) further co-amplifying said diluted first amplified product of step d) to produce a second amplified product thereof; and
   f) co-amplifying said second native nucleic acid and said second competitive template for said second native nucleic acid to produce an amplified product thereof.

5. The method of claim 4, further comprising the steps of:
   g) combining the amplified products of the co-amplification steps c), e) and f); and,
   h) amplifying the combined products of step g) in a second round of amplification using primer pairs that recognize each native nucleic acid target and competitive IAC product from a first round of amplification; wherein the primer pairs also have a gene-specific barcode sequence and a universal sequence to facilitate sequencing.

6. The method of claim 1, wherein the assessing step iv) comprises determining an amount of a first native nucleic acid target in a first sample, by:
   a) providing a series of serially-diluted standardized mixtures comprising a first competitive template internal amplification control (IAC) for a first native nucleic acid target and a second competitive template IAC for a second native nucleic acid target present in a number of samples that include said first native nucleic acid target, wherein said first and second competitive IAC templates are at known concentrations relative to each other;
   b) combining one of said samples comprising said first native nucleic acid target with a first one of said serially-diluted standardized mixtures;
   c) co-amplifying said first native nucleic acid target and said first competitive IAC template for said first native nucleic acid target to produce a first amplified product;
   d) obtaining a first relationship, said first relationship comparing said first amplified product of said first native nucleic acid target to said first amplified product of said competitive IAC template for said first native nucleic acid target;
   e) determining whether said first relationship is within about 1:10 to about 10:1; if not, repeating said combining step b), co-amplifying step c), obtaining step d) and determining step e) with a second one of said serially-diluted standardized mixtures;
   f) either simultaneously with step b) or after step b), co-amplifying said second native nucleic acid target and said second competitive IAC template for said second native nucleic acid target to produce a second amplified product;
   g) obtaining a second relationship, said second relationship comparing said second amplified product of said second native nucleic acid target to said second amplified product of said competitive IAC template for said second native nucleic acid target; and
   h) comparing said first and said second relationships.

7. The method of claim 6, wherein said method controls for at least two sources of variation selected from cDNA loading, intra-nucleic acid amplification efficiency, inter-nucleic acid amplification efficiency, inter-specimen amplification efficiency, inter-sample amplification efficiency, and intra-sample amplification efficiency.

8. The method of claim 7, further comprising using said second native nucleic acid target as a first reference nucleic acid to control for variations in cDNA loading.

9. The method of claim 6, wherein said series of serially-diluted standardized mixtures further comprises sufficient amounts of said competitive IAC for assessing said first native nucleic acid target in at least or about $10^6$ samples.

10. The method of claim 6, wherein said method is computer implemented; and, wherein said computer implementation comprises instructing a robotic handler to select said first one of said serially-diluted standardized mixtures for combining; and, optionally, wherein said computer implementation comprises instructing said robotic handler to select said second one of said serially-diluted standardized mixtures based on said first relationship.

11. The method of claim 1, wherein said method is computer implemented.

* * * * *